(12) United States Patent
Webber et al.

(10) Patent No.: US 6,914,158 B2
(45) Date of Patent: Jul. 5, 2005

(54) AMIDINO COMPOUNDS USEFUL AS NITRIC OXIDE SYNTHASE INHIBITORS

(75) Inventors: Ronald Keith Webber, Charles, MO (US); Richard C. Durley, Chesterfield, MO (US); Alok K. Awasthi, Skokie, IL (US); Arija A. Bergmanis, Des Plaines, IL (US); Kam F. Fok, St. Louis, MO (US); Scott S. Ganser, Chicago, IL (US); Timothy J. Hagen, Gurne, IL (US); E. Ann Hallinan, Evanston, IL (US); Donald W. Hansen, Jr., Skokie, IL (US); Brian S. Hickory, Wildwood, MO (US); Pamela T. Manning, Labadie, MO (US); Michael Mao, Chesterfield, MO (US); Alan E. Moormann, Weldon Springs, MO (US); Barnett S. Pitzele, Skokie, IL (US); Michelle A. Promo, Chesterfield, MO (US); Richard R. Schartman, Evanston, IL (US); Jeffrey A. Scholten, Chesterfield, MO (US); Jeffrey S. Snyder, Manchester, MO (US); Mihaly V. Toth, St. Louis, MO (US); Mahima Trivedi, Glenview, IL (US); Sofya Tsymbalov, Skokie, IL (US); Foe Siong Tjoeng, Ballwin, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 10/815,375

(22) Filed: Apr. 1, 2004

(65) Prior Publication Data

US 2004/0186178 A1 Sep. 23, 2004

Related U.S. Application Data

(62) Division of application No. 10/321,969, filed on Dec. 17, 2002, now abandoned, which is a division of application No. 09/816,575, filed on Mar. 23, 2001, now Pat. No. 6,586,474.
(60) Provisional application No. 60/191,923, filed on Mar. 24, 2000.

(51) Int. Cl.$^7$ ............................................. C07C 323/00
(52) U.S. Cl. ...................................................... 562/557
(58) Field of Search ........................................ 562/557

(56) References Cited

U.S. PATENT DOCUMENTS

| | | | |
|---|---|---|---|
| 5,132,453 A | 7/1992 | Griffith | ...................... 562/560 |
| 5,684,008 A | 11/1997 | Hallinan et al. | ............. 514/256 |
| 5,830,917 A | 11/1998 | Moore et al. | ................ 514/634 |
| 5,854,251 A | 12/1998 | Hallinan et al. | ............. 514/256 |
| 5,863,931 A | 1/1999 | Beams et al. | ................ 514/357 |
| 5,919,787 A | 7/1999 | Hallinan et al. | ............. 514/256 |
| 5,945,408 A | 8/1999 | Webber et al. | ................. 514/63 |
| 5,981,511 A | 11/1999 | Gapud et al. | .................. 514/63 |

FOREIGN PATENT DOCUMENTS

| | | | |
|---|---|---|---|
| EP | 0446699 | 5/2000 | ............ C07K/5/06 |
| EP | 0521471 | 10/2000 | ......... C07D/239/42 |
| WO | WO 93/13055 | 7/1993 | ......... C07C/257/14 |
| WO | WO 94/12165 | 6/1994 | ......... A61K/31/155 |
| WO | WO 94/14780 | 7/1994 | ......... C07D/239/48 |
| WO | WO 95/11014 | 4/1995 | .......... A61K/31/00 |
| WO | WO 95/11231 | 4/1995 | ......... C07D/207/22 |
| WO | WO 95/25717 | 9/1995 | ......... C07C/257/14 |
| WO | WO 96/15120 | 5/1996 | ......... C07D/257/06 |
| WO | WO 96/33175 | 10/1996 | ......... C07D/223/12 |
| WO | WO 96/35677 | 11/1996 | ......... C07D/223/12 |
| WO | WO 97/06802 | 2/1997 | ......... A61K/31/495 |
| WO | WO 99/46240 | 9/1999 | ......... C07C/257/14 |
| WO | WO 99/62875 | 12/1999 | ......... A61K/31/155 |

OTHER PUBLICATIONS

Jeanguenat et al; Stereoselective Chain Elongatyion at C–3 of Cysteine through 2,3–Dihydrothiazoles, Without Recemization. Preparation of 2–Amino–5–hydroxy–3–mercapto alkanoic Acid Derivatives J. Chem Soc. Perkin Trans.; 1; 2291–2298; 1991.

Pattenden et al; Enantioselective Synthesis of 2–Alkyl Substituted Cysteines; Tetrahedron; 49; 2131–2138; 1993.

Bredt et al; Isolation of Nitric Oxide Synthetase, a Calmodulin–Requiring Enzyme; Proc Natl Acad Sci USA; 87; 682–685; 1990.

Moore et al; 2–Iminopiperidine and Other 2–Iminoazaheterocycles as Potent Inhibitors of Human Nitric Oxide Synthase Isoforms; J. Med. Chem; 39; 669–672; 1996.

Misko et al; A Fluorometric Assay for the Measurement of Nitrite in Biological Samples; Analytical Biochemistry; 214; 11–16; 1993.

*Primary Examiner*—Paul A. Zucker
(74) *Attorney, Agent, or Firm*—Philip B. Polster, II; James M. Warner

(57) ABSTRACT

The present invention relates to amidino compounds and salts and prodrugs thereof. In another embodiment the present invention also provides a use of the present compounds in therapy, particular as nitric oxide synthase inhibitors. In a further embodiment, the present invention provides methods of making the amidino compounds.

14 Claims, No Drawings

AMIDINO COMPOUNDS USEFUL AS NITRIC OXIDE SYNTHASE INHIBITORS

CROSS REFERENCE TO RELATED APPLICATIONS

This application is a division of U.S. Ser. No. 10/321,969, filed Dec. 17, 2002, now abandoned which is a division of U.S. Ser. No. 09/816,575, filed Mar. 23, 2001, U.S. Pat. No. 6,586,474, which claims the benefit of priority of U.S. Provisional Patent Application No. 60/191,923 filed Mar. 24, 2000, herein incorporated by reference.

BACKGROUND OF THE INVENTION

1. Field of the Invention

The present invention relates to amidino compounds and their use in therapy, in particular their use as nitric oxide synthase inhibitors.

2. Related Art

It has been known since the early 1980's that the vascular relaxation caused by acetylcholine is dependent on the vascular endothelium. The endothelium-derived relaxing factor (EDRF), now known to be nitric oxide (NO) is generated in the vascular endothelium by nitric oxide synthase (NOS). The activity of NO as a vasodilator has been known for well over 100 years. In addition, NO is the active species deriving from amylnitrite, glyceryltrinitrate and other nitrovasodilators. The identification of EDRF as NO has coincided with the discovery of a biochemical pathway by which NO is synthesized from the amino acid L-arginine by the enzyme NO synthase.

Nitric oxide is an endogenous stimulator of the soluble guanylate cyclase. In addition to endothelium-dependent relaxation, NO is involved in a number of biological actions including cytotoxicity of phagocytic cells and cell-to-cell communication in the central nervous system.

There are at least three types of NO synthase as follows:

(i) a constitutive, $Ca^{++}$/calmodulin dependent enzyme, located in the endothelium, that releases NO in response to receptor or physical stimulation.

(ii) a constitutive, $Ca^{++}$/calmodulin dependent enzyme, located in the brain, that releases NO in response to receptor or physical stimulation.

(iii) a $Ca^{++}$ independent enzyme which is induced after activation of vascular smooth muscle, macrophages, endothelial cells, and a number of other cells by endotoxin and cytokines. Once expressed this inducible nitric oxide synthase (hereinafter "iNOS") generates NO continuously for long periods.

The NO released by each of the two constitutive enzymes acts as a transduction mechanism underlying several physiological responses. The NO produced by the inducible enzyme is a cytotoxic molecule for tumor cells and invading microorganisms. It also appears that adverse effects of excess NO production, in particular pathological vasodilation and tissue damage, may result largely from the NO synthesized by iNOS.

There is a growing body of evidence that NO may be involved in the degeneration of cartilage which takes place as a result of certain conditions such as arthritis and it is also known that NO synthesis is increased in rheumatoid arthritis and in osteoarthritis.

Some of the NO synthase inhibitors proposed for therapeutic use are non-selective; they inhibit both the constitutive and the inducible NO synthases. Use of such a non-selective NO synthase inhibitor requires that great care be taken in order to avoid the potentially serious consequences of over-inhibition of the constitutive NO-synthase including hypertension and possible thrombosis and tissue damage. In particular, in the case of the therapeutic use of L-NMMA for the treatment of toxic shock it has been recommended that the patient must be subject to continuous blood pressure monitoring throughout the treatment. Thus, while non-selective NO synthase inhibitors have therapeutic utility provided that appropriate precautions are taken, NO synthase inhibitors which are selective in the sense that they inhibit the inducible NO synthase to a considerably greater extent than the constitutive isoforms of NO synthase would be of even greater therapeutic benefit and easier to use (S. Moncada and E. Higgs, FASEB J., 9, 1319–1330, 1995).

The following individual publications disclose compounds that inhibit nitric oxide synthesis and preferentially inhibit the inducible isoform of nitric oxide synthase:
PCT Patent Application No. WO 96/35677.
PCT Patent Application No. WO 96/33175.
PCT Patent Application No. WO 96/15120.
PCT Patent Application No. WO 95/11014.
PCT Patent Application No. WO 95/11231.
PCT Patent Application No. WO 99/46240.
PCT Patent Application No. WO 95/24382.
PCT Patent Application No. WO 94/12165.
PCT Patent Application No. WO 94/14780.
PCT Patent Application No. WO 93/13055.
PCT Patent Application No. WO 99/62875.
European Patent No. EP0446699A1.
U.S. Pat. No. 5,132,453.
U.S. Pat. No. 5,684,008.
U.S. Pat. No. 5,830,917.
U.S. Pat. No. 5,854,251.
U.S. Pat. No. 5,863,931.
U.S. Pat. No. 5,919,787.
U.S. Pat. No. 5,945,408.
U.S. Pat. No. 5,981,511.

PCT Patent Application No. WO 95/25717 discloses certain amidino derivatives as being useful in inhibiting inducible nitric oxide synthase.

PCT Patent Application No. WO 99/62875 discloses further amidino compounds as being useful in inhibiting inducible nitric oxide synthase.

SUMMARY OF THE INVENTION

Compounds have now been found which have the advantage of being very efficacious as iNOS inhibitors in the human cartilage explant assay, a model for osteoarthritis. At the same time the compounds of the present invention are surprisingly unable to penetrate certain non-target organs in test systems, especially in comparison to the compounds of WO 95/25717. This surprising differentiation in expected access between the target organ (cartilage) and other organs is an unexpected advantage for the compounds of the present invention.

In a broad aspect, the present invention is directed to novel compounds, pharmaceutical compositions and methods of using said compounds and compositions for inhibiting or modulating nitric oxide synthesis in a subject in need of such inhibition or modulation by administering a compound which preferentially inhibits or modulates the inducible isoform of nitric oxide synthase over the constitutive isoforms of nitric oxide synthase. It is also another object of the present invention to lower nitric oxide levels in a subject in need of such lowering. The present compounds possess useful nitric oxide synthase inhibiting activity, and are expected to be useful in the treatment or prophylaxis of a disease or condition in which the synthesis or over-synthesis of nitric oxide forms a contributory part.

In one embodiment, the present invention provides a compound or a salt thereof, the compound having a structure corresponding to Formula 1:

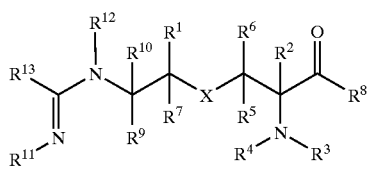

wherein:

X is selected from the group consisting of —S—, —S(O)—, and —S(O)$_2$—;

$R^2$ is selected from the group consisting of $C_1$–$C_6$ alkyl, $C_2$–$C_6$ alkenyl, $C_2$–$C_6$ alkynyl, $C_1$–$C_5$ alkoxy-$C_1$ alkyl, and $C_1$–$C_5$ alkylthio-$C_1$ alkyl;

with respect to $R^3$ and $R^8$:

$R^8$ is selected from the group consisting of —$OR^{14}$ and —$N(R^{15})(R^{16})$; and $R^3$ is selected from the group consisting of —H, —OH, —C(O)—$R^{17}$, —C(O)—O—$R^{18}$, and —C(O)—S—$R^{19}$; or $R^8$ is —$N(R^{20})$—, and $R^3$ is —C(O)—, wherein $R^8$ and $R^3$ together with the atoms to which they are attached form a ring; or $R^8$ is —O—, and $R^3$ is —$C(R^{21})(R^{22})$—, wherein $R^8$ and $R^3$ together with the atoms to which they are attached form a ring;

if $R^3$ is —$C(R^{21})(R^{22})$—, then $R^{23}$ is —C(O)—O—$R^{23}$; otherwise $R^4$ is —H;

$R^1$, $R^5$, $R^6$, and $R^7$ independently are selected from the group consisting of —H, halogen, $C_1$–$C_6$ alkyl, $C_2$–$C_6$ alkenyl, $C_2$–$C_6$ alkynyl, and $C_1$–$C_5$ alkoxy-$C_1$ alkyl;

$R^9$ and $R^{10}$ independently are selected from the group consisting of —H, $C_1$–$C_6$ alkyl, $C_2$–$C_6$ alkenyl, $C_2$–$C_6$ alkynyl, and $C_1$–$C_5$ alkoxy-$C_1$ alkyl;

with respect to $R^{11}$ and $R^{12}$:

$R^{11}$ is selected from the group consisting of —H, —OH, —C(O)—O—$R^{24}$, and —C(O)—S—$R^{25}$; and $R^{12}$ is selected from the group consisting of —H, —OH, —C(O)—O—$R^{26}$, and —C(O)—S—$R^{27}$; or $R^{11}$ is —O—, and $R^{12}$ is —C(O)—, wherein $R^{11}$ and $R^{12}$ together with the atoms to which they are attached form a ring; or $R^{11}$ is —C(O)—, and $R^{12}$ is —O—, wherein $R^{11}$ and $R^{12}$ together with the atoms to which they are attached form a ring; and $R^{13}$ is $C_1$ alkyl;

$R^{14}$ is selected from the group consisting of —H and $C_1$–$C_6$ alkyl; wherein when $R^{14}$ is $C_1$–$C_6$ alkyl, $R^{14}$ is optionally substituted by one or more moieties selected from the group consisting of cycloalkyl, heterocyclyl, aryl, and heteroaryl;

with respect to $R^{15}$ and $R^{16}$:

$R^{15}$ is selected from the group consisting of —H, alkyl, and alkoxy; and $R^{16}$ is selected from the group consisting of —H, —OH, alkyl, alkoxy, —C(O)—$R^{27a}$, —C(O)—O—$R^{28}$, and —C(O)—S—$R^{29}$; wherein when $R^{15}$ and $R^{16}$ independently are alkyl or alkoxy, $R^{15}$ and $R^{16}$ independently are optionally substituted with one or more moieties selected from the group consisting of cycloalkyl, heterocyclyl, aryl, and heteroaryl; or $R^{15}$ is —H; and $R^{16}$ is selected from the group consisting of cycloalkyl, heterocyclyl, aryl, and heteroaryl;

$R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{27a}$, $R^{28}$, and $R^{29}$ independently are selected from the group consisting of —H and alkyl, which is optionally substituted by one or more moieties selected from the group consisting of cycloalkyl, heterocyclyl, aryl, and heteroaryl; and when any of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{27a}$, $R^{28}$, and $R^{29}$ independently is a moiety selected from the group consisting of alkyl, alkenyl, alkynyl, alkoxy, alkylthio, cycloalkyl, heterocyclyl, aryl, and heteroaryl, then the moiety is optionally substituted by one or more substituent selected from the group consisting of —OH, alkoxy, and halogen.

Another embodiment provides a method for the treatment or prevention of an inflammation-related disorder wherein the method comprises treating a subject in need thereof with an inflammation-related disorder treating or preventing amount of a compound of the present invention.

In yet another embodiment the present invention provides a method for the preparation of a compound of Formula 1, wherein the method comprises treating a diamine compound having a structure corresponding to Formula 22:

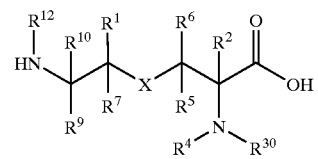

or a salt thereof, with an alkyl acetimidate having a structure corresponding to Formula 23:

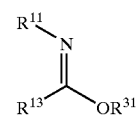

wherein $R^{31}$ is $C_1$–$C_6$ alkyl. The treating can, if desired, be performed in the presence of an acid or a base, preferably in the presence of a base.

In a further embodiment of the present invention provides a method for the preparation of a diamine compound having a structure corresponding to Formula 22:

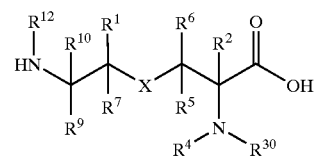

or a salt thereof, wherein $R^{30}$ is selected from the group consisting of —H, —OH, —C(O)—$R^{17}$, —C(O)—O—$R^{18}$, and —C(O)—S—$R^{19}$, and the other substituents are as defined above, wherein the method comprises treating a protected diamine compound having the structure corresponding to Formula 24:

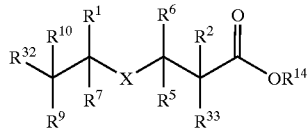

or a salt thereof, wherein $R^{33}$ is selected from the group consisting of —H and a protected amino group; and $R^{32}$ is a protected amino group; and $R^{14}$ is selected from the group consisting of —H and $C_1$–$C_6$ alkyl; wherein when $R^{14}$ is $C_1$–$C_6$ alkyl, $R^{14}$ is optionally substituted by one or more moieties selected from the group consisting of cycloalkyl, heterocyclyl, aryl, and heteroaryl; wherein the treating is performed with a deprotecting reagent, thereby producing the diamine compound.

DETAILED DESCRIPTION OF THE INVENTION

Compounds of Formula 1 will be useful for treating, among other things, inflammation in a subject, or for treating other nitric oxide synthase-mediated disorders, such as, as an analgesic in the treatment of pain and headaches, or as an antipyretic for the treatment of fever. For example, compounds of the present invention will be useful to treat arthritis, including but not limited to rheumatoid arthritis, spondyloarthropathies, gouty arthritis, osteoarthritis, systemic lupus erythematosus, juvenile arthritis, acute rheumatic arthritis, enteropathic arthritis, neuropathic arthritis, psoriatic arthritis, and pyogenic arthritis. Conditions in which the compounds of the present invention will provide an advantage in inhibiting NO production from L-arginine include arthritic conditions.

Compounds of the invention will be further useful in the treatment of asthma, bronchitis, menstrual cramps (e.g., dysmenorrhea), premature labor, tendinitis, bursitis, skin-related conditions such as psoriasis, eczema, burns, sunburn, dermatitis, pancreatitis, hepatitis, and from post-operative inflammation including from ophthalmic surgery such as cataract surgery and refractive surgery. Compounds of the invention also would be useful to treat gastrointestinal conditions such as inflammatory bowel disease, Crohn's disease, gastritis, irritable bowel syndrome and ulcerative colitis. Compounds of the invention would be useful for the prevention or treatment of cancer, such as colorectal cancer, and cancer of the breast, lung, prostate, bladder, cervix and skin. Compounds of the invention would be useful in treating inflammation and tissue damage in such diseases as vascular diseases, migraine headaches, periarteritis nodosa, thyroiditis, aplastic anemia, Hodgkin's disease, sclerodoma, rheumatic fever, type I diabetes, neuromuscular junction disease including myasthenia gravis, white matter disease including multiple sclerosis, sarcoidosis, nephrotic syndrome, Behcet's syndrome, polymyositis, gingivitis, nephritis, hypersensitivity, swelling occurring after injury, myocardial ischemia, and the like. The compounds would also be useful in the treatment of ophthalmic diseases, such as glaucoma, retinitis, retinopathies, uveitis, ocular photophobia, and of inflammation and pain associated with acute injury to the eye tissue. Of particular interest among the uses of the present inventive compounds is the treatment of glaucoma, especially where symptoms of glaucoma are caused by the production of nitric oxide, such as in nitric oxide-mediated nerve damage. The compounds would also be useful in the treatment of pulmonary inflammation, such as that associated with viral infections and cystic fibrosis. The compounds would also be useful for the treatment of certain central nervous system disorders, such as cortical dementias including Alzheimer's disease, and central nervous system damage resulting from stroke, ischemia and trauma. The compounds of the invention are useful as anti-inflammatory agents, such as for the treatment of arthritis, with the additional benefit of having significantly less harmful side effects. These compounds would also be useful in the treatment of allergic rhinitis, respiratory distress syndrome, endotoxin shock syndrome, and atherosclerosis. The compounds would also be useful in the treatment of pain, but not limited to postoperative pain, dental pain, muscular pain, and pain resulting from cancer. The compounds would be useful for the prevention of dementias, such as Alzheimer's disease.

Besides being useful for human treatment, these compounds are also useful for veterinary treatment of companion animals, exotic animals and farm animals, including mammals, rodents, and the like. More preferred animals include horses, dogs, and cats.

The present compounds may also be used in co-therapies, partially or completely, in place of other conventional anti-inflammatory therapies, such as together with steroids, NSAIDs, COX-2 selective inhibitors, 5-lipoxygenase inhibitors, $LTB_4$ antagonists and LTA4 hydrolase inhibitors.

Other conditions in which the compounds of the present invention will provide an advantage in inhibiting NO inhibition include cardiovascular ischemia, diabetes (type I or type II), congestive heart failure, myocarditis, atherosclerosis, migraine, glaucoma, aortic aneurysm, reflux esophagitis, diarrhea, irritable bowel syndrome, cystic fibrosis, emphysema, asthma, bronchiectasis, hyperalgesia (allodynia), cerebral ischemia (both focal ischemia, thrombotic stroke and global ischemia (for example, secondary to cardiac arrest), multiple sclerosis and other central nervous system disorders mediated by NO, for example Parkinson's disease. Further neurodegenerative disorders in which NO inhibition may be useful include nerve degeneration or nerve necrosis in disorders such as hypoxia, hypoglycemia, epilepsy, and in cases of central nervous system (CNS) trauma (such as spinal cord and head injury), hyperbaric oxygen convulsions and toxicity, dementia e.g. pre-senile dementia, and AIDS-related dementia, cachexia, Sydenham's chorea, Huntington's disease, Amyotrophic Lateral Sclerosis, Korsakoff's disease, imbecility relating to a cerebral vessel disorder, sleeping disorders, schizophrenia, depression, depression or other symptoms associated with Premenstrual Syndrome (PMS), anxiety and septic shock.

The compounds of the present invention will also be useful in the treatment of pain including somatogenic (either nociceptive or neuropathic), both acute and chronic. A nitric oxide inhibitor could be used in any situation including neuropathic pain that a common NSAID or opioid analgesic would traditionally be administered.

Still other disorders or conditions which will be advantageously treated by the compounds of the present invention include treatment of prevention of opiate tolerance in patients needing protracted opiate analgesics, and benzodiazepine tolerance in patients taking benzodiazepines, and other addictive behavior, for example, nicotine addiction, alcoholism, and eating disorders. The compounds and methods of the present invention will also be useful in the treatment or prevention of drug withdrawal symptoms, for example treatment or prevention of symptoms of withdrawal from opiate, alcohol, or tobacco addiction. The present inventive compounds may also be useful to prevent tissue damage when therapeutically combined with antibacterial or antiviral agents.

The compounds of the present invention will also be useful in inhibiting NO production from L-arginine including systemic hypotension associated with septic and/or toxic hemorrhagic shock induced by a wide variety of agents; therapy with cytokines such as TNF, IL-1 and IL-2; and as an adjuvant to short term immunosuppression in transplant therapy.

The present invention is further directed to the use of the compounds of the present invention for the treatment and prevention of neoplasias. The neoplasias that will be treatable or preventable by the compounds and methods of the present invention include brain cancer, bone cancer, a leukemia, a lymphoma, epithelial cell-derived neoplasia (epithelial carcinoma) such as basal cell carcinoma, adenocarcinoma, gastrointestinal cancer such as lip cancer, mouth cancer, esophogeal cancer, small bowel cancer and stomach cancer, colon cancer, liver cancer, bladder cancer, pancreas cancer, ovary cancer, cervical cancer, lung cancer, breast cancer and skin cancer, such as squamous cell and basal cell cancers, prostate cancer, renal cell carcinoma, and other known cancers that effect epithelial cells throughout the body. Preferably, the neoplasia is selected from gastrointestinal cancer, liver cancer, bladder cancer, pancreas cancer, ovary cancer, prostate cancer, cervical cancer, lung cancer, breast cancer and skin cancer, such as squamous cell and basal cell cancers. The present compounds and methods can also be used to treat the fibrosis which occurs with radiation therapy. The present compounds and methods can be used to treat subjects having adenomatous polyps, including those with familial adenomatous polyposis (FAP). Additionally, the present compounds and methods can be used to prevent polyps from forming in patients at risk of FAP.

Conjunctive treatment of a compound of the present invention with another antineoplastic agent will produce a synergistic effect or alternatively reduce the toxic side effects associated with chemotherapy by reducing the therapeutic dose of the side effect-causing agent needed for therapeutic efficacy or by directly reducing symptoms of toxic side effects caused by the side effect-causing agent. A compound of the present invention will further be useful as an adjunct to radiation therapy to reduce side effects or enhance efficacy. In the present invention, another agent which can be combined therapeutically with a compound of the present invention includes any therapeutic agent which is capable of inhibiting the enzyme cyclooxygenase-2 ("COX-2"). Preferably such COX-2 inhibiting agents inhibit COX-2 selectively relative to the enzyme cyclooxygenase-1 ("COX-1"). Such a COX-2 inhibitor is known as a "COX-2 selective inhibitor". More preferably, a compound of the present invention can be therapeutically combined with a COX-2 selective inhibitor wherein the COX-2 selective inhibitor selectively inhibits COX-2 at a ratio of at least 10:1 relative to inhibition of COX-1, more preferably at least 30:1, and still more preferably at least 50:1 in an in vitro test. COX-2 selective inhibitors useful in therapeutic combination with the compounds of the present invention include celecoxib, valdecoxib, deracoxib, etoricoxib, rofecoxib, ABT-963 (2-(3,4-difluorophenyl)-4-(3-hydroxy-3-methyl-1-butoxy)-5-[4-(methylsulfonyl)phenyl-3(2H)-pyridazinone; described in PCT Patent Application No. WO 00/24719), or meloxicam. A compound of the present invention can also be advantageously used in therapeutic combination with a prodrug of a COX-2 selective inhibitor, for example parecoxib.

Another chemotherapeutic agent which will be useful in combination with a compound of the present invention can be selected, for example, from the following non-comprehensive and non-limiting list:

Alpha-difluoromethylornithine (DFMO), 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, uricytin, Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin, trimelamol, Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-A1b, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 zorubicin, alpha-carotene, alpha-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluron, benzotript, Ipsen-Beaufour BIM-23015, bisantrene, Bristo-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemex CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-SN, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, uroguanylin, combretastatin, dolastatin, idarubicin, epirubicin, estramustine, cyclophosphamide, 9-amino-2-(S)-camptothecin, topotecan, irinotecan (Camptosar), exemestane, decapeptyl (tryptorelin), or an omega-3 fatty acid.

Examples of radioprotective agents which may be used in a combination therapy with the compounds of this invention include AD-5, adchnon, amifostine analogues, detox, dimesna, 1-102, MM-159, N-acylated-dehydroalanines, TGF-Genentech, tiprotimod, amifostine, WR-151327, FUT-187, ketoprofen transdermal, nabumetone, superoxide dismutase (Chiron) and superoxide dismutase Enzon.

The compounds of the present invention will also be useful in treatment or prevention of angiogenesis-related disorders or conditions, for example, tumor growth, metastasis, macular degeneration, and atherosclerosis.

In a further embodiment, the present invention also provides therapeutic combinations for the treatment or prevention of ophthalmic disorders or conditions such as glaucoma. For example the present inventive compounds advantageously will be used in therapeutic combination with a drug which reduces the intraocular pressure of patients afflicted with glaucoma. Such intraocular pressure-reducing drugs include without limitation latanoprost, travoprost, bimatoprost, or unoprostol. The therapeutic combination of a compound of the present invention plus an intraocular pressure-reducing drug will be useful because each is believed to achieve its effects by affecting a different mechanism.

In another combination of the present invention, the present inventive compounds can be used in therapeutic combination with an antihyperlipidemic or cholesterol-lowering drug such as a benzothiepine or a benzothiazepine antihyperlipidemic drug. Examples of benzothiepine antihyperlipidemic drugs useful in the present inventive therapeutic combination can be found in U.S. Pat. No. 5,994,391, herein incorporated by reference. Some benzothiazepine antihyperlipidemic drugs are described in WO 93/16055. Alternatively, the antihyperlipidemic or cholesterol-lowering drug useful in combination with a compound of the present invention can be an HMG Co-A reductase inhibitor. Examples of HMG Co-A reductase inhibitors useful in the present therapeutic combination include, individually, benfluorex, fluvastatin, lovastatin, provastatin, simvastatin, atorvastatin, cerivastatin, bervastatin, ZD-9720 (described in PCT Patent Application No. WO 97/06802), ZD-4522 (CAS No. 147098-20-2 for the calcium salt; CAS No. 147098-18-8 for the sodium salt; described in European Patent No. EP 521471), BMS 180431 (CAS No. 129829-03-4), or NK-104 (CAS No. 141750-63-2). The therapeutic combination of a compound of the present invention plus an antihyperlipidemic or cholesterol-lowering drug will be useful, for example, in reducing the risk of formation of atherosclerotic lesions in blood vessels. For example, atherosclerotic lesions often initiate at inflamed sites in blood vessels. It is established that antihyperlipidemic or cholesterol-lowering drug reduce risk of formation of atherosclerotic lesions by lowering lipid levels in blood. Without limiting the invention to a single mechanism of action, it is believed that one way the compounds of the present combination will work in concert to provide improved control of atherosclerotic lesions by, for example, reducing inflammation of the blood vessels in concert with lowering blood lipid levels.

In another embodiment of the invention, the present compounds can be used in combination with other compounds or therapies for the treatment of central nervous conditions or disorders such as migraine. For example, the present compounds can be used in therapeutic combination with caffeine, a 5-HT-1B/1D agonist (for example, a triptan such as sumatriptan, naratriptan, zolmitriptan, rizatriptan, almotriptan, or frovatriptan), a dopamine D4 antagonist (e.g., sonepiprazole), aspirin, acetaminophen, ibuprofen, indomethacin, naproxen sodium, isometheptene, dichloralphenazone, butalbital, an ergot alkaloid (e.g., ergotamine, dihydroergotamine, bromocriptine, ergonovine, or methyl ergonovine), a tricyclic antidepressant (e.g., amitriptyline or nortriptyline), a serotonergic antagonist (e.g., methysergide or cyproheptadine), a beta-andrenergic antagonist (e.g., propranolol, timolol, atenolol, nadolol, or metprolol), or a monoamine oxidase inhbitor (e.g., phenelzine or isocarboxazid).

A further embodiment provides a therapeutic combination of a compound of the present invention with an opioid compound. Opioid compounds useful in this combination include without limitation morphine, methadone, hydromorphone, oxymorphone, levorphanol, levallorphan, codeine, dihydrocodeine, dihydrohydroxycodeinone, pentazocine, hydrocodone, oxycodone, nalmefene, etorphine, levorphanol, fentanyl, sufentanil, DAMGO, butorphanol, buprenorphine, naloxone, naltrexone, CTOP, diprenorphine, beta-funaltrexamine, naloxonazine, nalorphine, pentazocine, nalbuphine, naloxone benzoylhydrazone, bremazocine, ethylketocyclazocine, U50,488, U69,593, spiradoline, nor-binaltorphimine, naltrindole, DPDPE, [D-la$^2$, glu$^4$]deltorphin, DSLET, met-enkephalin, leu-enkaphalin, beta-endorphin, dynorphin A, dynorphin B, and alpha-neoendorphin. An advantage to the combination of the present invention with an opioid compound is that the present inventive compounds will allow a reduction in the dose of the opioid compound, thereby reducing the risk or severity of opioid side effects, such as opioid addiction.

The term "alkyl", alone or in combination, means an acyclic alkyl radical, linear or branched, preferably containing from 1 to about 10 carbon atoms and more preferably containing from 1 to about 6 carbon atoms. "Alkyl" also encompasses cyclic alkyl radicals containing from 3 to about 7 carbon atoms, preferably from 3 to 5 carbon atoms. Said alkyl radicals can be optionally substituted with groups as defined below. Examples of such radicals include methyl, ethyl, chloroethyl, hydroxyethyl, n-propyl, isopropyl, n-butyl, cyanobutyl, isobutyl, sec-butyl, tert-butyl, pentyl, aminopentyl, iso-amyl, hexyl, octyl and the like.

The term "alkenyl" refers to an unsaturated, acyclic hydrocarbon radical, linear or branched, in so much as it contains at least one double bond. Such radicals containing from 2 to about 6 carbon atoms, preferably from 2 to about 4 carbon atoms, more preferably from 2 to about 3 carbon atoms. Said alkenyl radicals may be optionally substituted with groups as defined below. Examples of suitable alkenyl radicals include propenyl, 2-chloropropylenyl, buten-1-yl, isobutenyl, penten-1-yl, 2-methylbuten-1-yl, 3-methylbuten-1-yl, hexen-1-yl, 3-hydroxyhexen-1-yl, hepten-1-yl, and octen-1-yl, and the like.

The term "alkynyl" refers to an unsaturated, acyclic hydrocarbon radical, linear or branched, in so much as it contains one or more triple bonds, such radicals containing 2 to about 6 carbon atoms, preferably from 2 to about 4 carbon atoms, more preferably from 2 to about 3 carbon atoms. Said alkynyl radicals may be optionally substituted with groups as defined below. Examples of suitable alkynyl radicals include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, hexyn-3-yl, 3,3-dimethylbutyn-1-yl radicals and the like.

The term "alkoxy" embrace linear or branched oxy-containing radicals each having alkyl portions of 1 to about 6 carbon atoms, preferably 1 to about 3 carbon atoms, such as a methoxy radical. The term "alkoxyalkyl" also embraces alkyl radicals having one or more alkoxy radicals attached to the alkyl radical, that is, to form monoalkoxyalkyl and dialkoxyalkyl radicals. Examples of such radicals include methoxy, ethoxy, propoxy, butoxy and tert-butoxy alkyls. The "alkoxy" radicals may be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylthio" embraces radicals containing a linear or branched alkyl radical, of 1 to about 6 carbon atoms, attached to a divalent sulfur atom. An example of "lower alkylthio" is methylthio ($CH_3$—S—).

The term "alkylthioalkyl" embraces alkylthio radicals, attached to an alkyl group. Examples of such radicals include methylthiomethyl.

The term "halo" means halogens such as fluorine, chlorine, bromine or iodine atoms.

The term "heterocyclyl" means a saturated or unsaturated mono- or multi-ring carbocycle wherein one or more carbon atoms is replaced by N, S, P, or O. This includes, for example, the following structures:

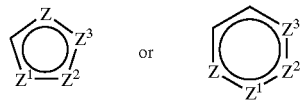

wherein Z, $Z^1$, $Z^2$ or $Z^3$ is C, S, P, O, or N, with the proviso that one of Z, $Z^1$, $Z^2$ or $Z^3$ is other than carbon, but is not O or S when attached to another Z atom by a double bond or when attached to another O or S atom. Furthermore, the optional substituents are understood to be attached to Z, $Z^1$, $Z^2$ or $Z^3$ only when each is C. The term "heterocyclyl" also includes fully saturated ring structures such as piperazinyl, dioxanyl, tetrahydrofuranyl, oxiranyl, aziridinyl, morpholinyl, pyrrolidinyl, piperidinyl, thiazolidinyl, and others. The term "heterocyclyl" also includes partially unsaturated ring structures such as dihydrofuranyl, pyrazolinyl, imidazolinyl, pyrrolinyl, chromanyl, dihydrothiophenyl, and others.

The term "heteroaryl" means a fully unsaturated heterocycle.

In either "heterocycle" or "heteroaryl," the point of attachment to the molecule of interest can be at the heteroatom or elsewhere within the ring.

The term "cycloalkyl" means a mono- or multi-ringed carbocycle wherein each ring contains three to about seven carbon atoms, preferably three to about five carbon atoms. Examples include radicals such as cyclopropyl, cyclobutyl, cyclopentyl, cyclohexyl, cycloalkenyl, and cycloheptyl. The term "cycloalkyl" additionally encompasses spiro systems wherein the cycloalkyl ring has a carbon ring atom in common with the seven-membered heterocyclic ring of the benzothiepine.

The term "oxo" means a doubly bonded oxygen.

The term "alkoxy" means a radical comprising an alkyl radical that is bonded to an oxygen atom, such as a methoxy radical. More preferred alkoxy radicals are "lower alkoxy" radicals having one to about ten carbon atoms. Still more preferred alkoxy radicals have one to about six carbon atoms. Examples of such radicals include methoxy, ethoxy, propoxy, isopropoxy, butoxy and tert-butoxy.

The term "aryl" means a fully unsaturated mono- or multi-ring carbocycle, including, but not limited to, substituted or unsubstituted phenyl, naphthyl, or anthracenyl.

The term "Combination therapy" means the administration of two or more therapeutic agents to treat a therapeutic condition or disorder described in the present disclosure, for example atherosclerosis, pain, inflammation, migraine, neoplasia, angiogenisis-related condition or disorder, or other. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective" is intended to qualify the combined amount of active ingredients in the combination therapy. This combined amount will achieve the goal of reducing or eliminating the hyperlipidemic condition.

In one embodiment, the present invention provides a compound or a salt thereof, the compound having a structure corresponding to Formula 1:

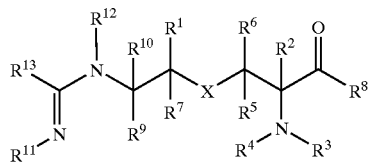

1

In the structure of Formula 1, X is selected from the group consisting of —S—, —S(O)—, and —S(O)$_2$—. Preferably, X is —S—. $R^2$ is selected from the group consisting of $C_1$–$C_6$ alkyl, $C_2$–$C_6$ alkenyl, $C_2$–$C_6$ alkynyl, $C_1$–$C_5$ alkoxy-$C_1$ alkyl, and $C_1$–$C_5$ alkylthio-$C_1$ alkyl wherein each of these groups is optionally substituted by one or more substituent selected from the group consisting of —OH, alkoxy, and halogen. Preferably, $R^2$ is $C_1$–$C_6$ alkyl optionally substituted with a substituent selected from the group consisting of —OH, alkoxy, and halogen. With respect to $R^3$ and $R^8$, $R^8$ is selected from the group consisting of —OR$^{14}$ and —N(R$^{15}$)(R$^{16}$), and $R^3$ is selected from the group consisting of —H, —OH, —C(O)—R$^{17}$, —C(O)—O—R$^{18}$, and —C(O)—S—R$^{19}$; or R$^{19}$ is —N(R$^{20}$)—, and R$^3$ is —C(O)—, wherein $R^8$ and $R^3$ together with the atoms to which they are attached form a ring; or $R^8$ is —O—, and $R^3$ is —C(R$^{21}$)(R$^{22}$)—, wherein $R^8$ and $R^3$ together with the atoms to which they are attached form a ring. If $R^3$ is —C(R$^{21}$)(R$^{22}$)—, then $R^4$ is —C(O)—O—R$^{23}$; otherwise $R^4$ is —H. $R^1$, $R^5$, $R^6$, and $R^7$ independently are selected from the group consisting of —H, halogen, $C_1$–$C_6$ alkyl, $C_2$–$C_6$ alkenyl, $C_2$–$C_6$ alkynyl, and $C_1$–$C_5$ alkoxy-$C_1$alkyl. $R^9$ and $R^{10}$ independently are selected from the group consisting of —H, $C_1$–$C_6$ alkyl, $C_2$–$C_6$ alkenyl, $C_2$–$C_6$ alkynyl, and $C_1$–$C_5$ alkoxy-$C_1$ alkyl. With respect to $R^{11}$ and $R^{12}$, $R^{11}$ is selected from the group consisting of —H, —OH, —C(O)—O—R$^{24}$, and —C(O)—S—R$^{25}$, and $R^{12}$ is selected from the group consisting of —H, —OH, —C(O)—O—R$^{26}$, and —C(O)—S—R$^{27}$; or $R^{11}$ is —O—, and $R^{12}$ is —C(O)—, wherein $R^{11}$ and $R^{12}$ together with the atoms to which they are attached form a ring; or $R^{11}$ is —C(O)—, and $R^{12}$ is —O—, wherein $R^{11}$ and $R^{12}$ together with the atoms to which they are attached form a ring. $R^{13}$ is $C_1$ alkyl. $R^{14}$ is selected from the group consisting of —H and $C_1$–$C_6$ alkyl, wherein when $R^{14}$ is $C_1$–$C_6$ alkyl, $R^{14}$ is optionally substituted by one or more moieties selected from the group consisting of cycloalkyl, heterocyclyl, aryl, and heteroaryl. With respect to $R^{15}$ and $R^{16}$, $R^{15}$ is selected from the group consisting of —H, alkyl, and alkoxy, and $R^{16}$ is selected from the group consisting of —H, —OH, alkyl, alkoxy, —C(O)—R$^{27a}$, —C(O)—O—R$^{28}$, and —C(O)—S—R$^{29}$; wherein when $R^{15}$ and $R^{16}$ independently are alkyl or alkoxy, $R^{15}$ and $R^{16}$ independently are optionally substituted with one or more moieties selected from the group consisting of cycloalkyl, heterocyclyl, aryl, and heteroaryl; or $R^{15}$ is —H; and $R^{16}$ is selected from the group consisting of cycloalkyl, heterocyclyl, aryl, and heteroaryl. $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{27a}$, $R^{28}$, and $R^{29}$ independently are selected from the group consisting of —H and alkyl, wherein alkyl is optionally substituted by one or more moieties selected from the group consisting of cycloalkyl, heterocyclyl, aryl, and heteroaryl. When any of $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, $R^{27a}$, $R^{28}$, and $R^{29}$ independently is a moiety selected from the group consisting of alkyl, alkenyl, alkynyl, alkoxy, alkylthio, cycloalkyl, heterocyclyl, aryl, and heteroaryl, then the moiety is optionally substituted by one or more substituent selected from the group consisting of —OH, alkoxy, and halogen.

In a preferred embodiment, $R^8$ is —OH. When $R^8$ is —OH, preferably X is S. In a further embodiment, $R^1$, $R^5$, $R^6$, $R^7$, $R^9$, and $R^{10}$ independently are selected from the group consisting of —H and $C_1$–$C_3$ alkyl. Preferably $R^5$, $R^6$, $R^7$, $R^9$, $R^{10}$ each are —H. $R^{13}$ can be a variety of groups, for example fluoromethyl or methyl. $R^1$ can be $C_1$–$C_6$ alkyl optionally substituted with a substituent selected from the group consisting of —OH and halogen; preferably $R^1$ is $C_1$ alkyl optionally substituted with halogen; more preferably $R^1$ is selected from the group consisting of fluoromethyl, hydroxymethyl, and methyl. In one important embodiment $R^1$ can be methyl. Alternatively, $R^1$ can be fluoromethyl. In another alternative $R^1$ can be hydroxymethyl. In another embodiment, $R^2$ is $C_1$–$C_6$ alkyl optionally substituted with a substituent selected from the group consisting of —OH, alkoxy, and halogen. In one preferred embodiment $R^2$ is $C_1$ alkyl optionally substituted with halogen. For example, $R^2$ can be methyl. Alternatively, $R^2$ can be fluoromethyl. In yet another example, $R^2$ can be hydroxymethyl. In still another example, $R^2$ can be methoxymethyl.

In the compounds of the present invention, it is preferred that $R^3$, $R^4$, $R^{11}$ and $R^{12}$ each is —H. In this embodiment, it is further preferred that $R^1$, $R^5$, $R^6$, $R^7$, $R^9$, and $R^{10}$ independently are selected from the group consisting of —H and $C_1$–$C_3$ alkyl. Preferably $R^5$, $R^6$, $R^7$, $R^9$, $R^{10}$ each is —H. In this further embodiment, $R^{13}$ can be, for example, fluoromethyl, or in another example $R^{13}$ can be methyl. In preferred compounds of these examples, $R^2$ is $C_1$–$C_6$ alkyl optionally substituted with a substituent selected from the group consisting of —OH, alkoxy, and halogen. Preferably $R^2$ is $C_1$ alkyl optionally substituted with halogen. In one such example $R^2$ is fluoromethyl. In another example $R^2$ is methyl. Alternatively $R^2$ can be hydroxymethyl. In another alternative, $R^2$ can be methoxymethyl.

When $R^{13}$ is methyl, $R^1$ can be, for example, —H or $C_1$–$C_6$ alkyl optionally substituted with a substituent selected from the group consisting of —OH and halogen. In a preferred embodiment $R^1$ is —H. Alternatively, $R^1$ can be $C_1$–$C_6$ alkyl optionally substituted with a substituent selected from the group consisting of —OH and halogen. For example $R^1$ can be methyl, ethyl, n-propyl, i-propyl, n-butyl, sec-butyl, isobutyl, t-butyl, a pentyl isomer, or a hexyl isomer. For example, $R^1$ can be ethyl. Alternatively, $R^1$ can be $C_1$ alkyl optionally substituted with a substituent selected from the group consisting of —OH and halogen; for example $R^1$ can be methyl. Alternatively, $R^1$ can be fluoromethyl. In another alternative, $R^1$ can be hydroxymethyl.

In another embodiment $R^8$ can be —$OR^{14}$. $R^{14}$ can be as defined above. Preferably $R^{14}$ is $C_1$–$C_6$ alkyl optionally substituted by one or more moieties selected from the group consisting of cycloalkyl, heterocyclyl, aryl, and heteroaryl; more preferably $R^{14}$ is $C_1$–$C_3$ alkyl; and more preferably still $R^{14}$ is methyl. In yet another embodiment of compound 1, $R^8$ can be —$N(R^{15})(R^{16})$, wherein $R^{15}$ and $R^{16}$ are as defined above. In still another embodiment $R^8$ can be —$N(R^{20})$—, and $R^3$ can be —C(O)—, wherein $R^8$ and $R^3$ together with the atoms to which they are attached form a ring. In another embodiment still, $R^8$ can be —O—, and $R^3$ can be —$C(R^{21})(R^{22})$—, wherein $R^8$ and $R^3$ together with the atoms to which they are attached form a ring.

In the compound of Formula 1, $R^{11}$ can be selected from the group consisting of —OH, —C(O)—O—$R^{24}$, and —C(O)—S—$R^{25}$. Preferably $R^{11}$ is —OH. In a further embodiment $R^{12}$ is —H when $R^{11}$ is —OH.

However, the present invention also provides useful compounds of Formula 1 in which $R^{11}$ is —O—, and $R^{12}$ is —C(O)—, wherein $R^{11}$ and $R^{12}$ together with the atoms to which they are attached form a ring. In another useful embodiment $R^{11}$ is —C(O)—, and $R^{12}$ is —O—, wherein $R^{11}$ and $R^{12}$ together with the atoms to which they are attached form a ring. Alternatively, $R^{12}$ can be selected from the group consisting of —OH, —C(O)—O—$R^{26}$, and —C(O)—S—$R^{27}$. In this alternative, $R^{11}$ is preferably —H.

The present invention also provides pharmaceutically-acceptable salts of the compounds of Formula 1. For example, such a pharmaceutically acceptable salt can be one in which the present inventive compound is in a cationic form with at least one anionic counterion. Examples of anionic counterions useful in the pharmaceutically-acceptable salts of the present invention include a halide, a carboxylate, a sulfonate, a sulfate, a phosphate, a phosphonate, a resin-bound anion, or a nitrate. When the anionic counterion is a halide, it can be, for example fluoride, chloride, bromide, or iodide. Preferably the halide counterion is chloride. When the anionic counterion is a carboxylate (i.e., the anionic form of a compound containing a carboxylic acid functional group), the carboxylate counterion can vary widely. The carboxylate counterion can be, for example, formate, acetate, propionate, trifluoroacetate, succinate, salicylate, DL-aspartate, D-aspartate, L-aspartate, DL-glutamate, D-glutamate, L-glutamate, glycerate, succinate, steric, DL-tartarate, D-tartarate, L-tartarate, (±)-mandelate, (R)-(–)-mandelate, (S)-(+)-mandelate, citrate, mucate, maleate, malonate, benzoate, DL-malate, D-malate, L-malate, hemi-malate, 1-adamantaneacetate, 1-adamantanecarboxylate, flavianate, sulfonoacetate, (±)-lactate, L-(+)-lactate, D-(–)-lactate, pamoate, D-alpha-galacturonate, glycerate, DL-ascorbate, D-ascorbate, L-ascorbate, DL-cystate, D-cystate, L-cystate, DL-homocystate, D-homocystate, L-homocystate, DL-cysteate, D-cysteate, L-cysteate, (4S)-hydroxy-L-proline, cyclopropane-1,1-dicarboxylate, 2,2-dimethylmalonate, squarate, tyrosine anion, proline anion, fumarate, 1-hydroxy-2-naphthoate, phosphonoacetate, carbonate, bicarbonate, 3-phosphonopropionate, DL-pyroglutamate, D-pyroglutamate, or L-pyroglutamate. Alternatively, the anionic counterion can be a sulfonate. For example the sulfonate counterion can be methanesulfonate, toluenesulfonate, benzenesulfonate, trifluoromethylsulfonate, ethanesulfonate, (±)-camphorsulfonate, naphthalenesulfonate, 1R-(–)-camphorsulfonate, 1S-(+)-camphorsulfonate, 2-mesitylenesulfonate, 1,5-naphthalenedisulfonate, 1,2-ethanedisulfonate, 1,3-propanedisulfonate, 3-(N-morpholino)propane sulfonate, biphenylsulfonate, isethionate, or 1-hydroxy-2-naphthalenesulfonate. In another embodiment the anionic counterion can be a sulfate. Examples of sulfates useful in the present invention include without limitation sulfate, monopotassium sulfate, monosodium sulfate, and hydrogen sulfate. The anionic counterion can be a sulfamate. When the anionic counterion is a phosphate, it can be, for example, phosphate, dihydrogen phosphate, potassium hydrogen phosphate, dipotassium phosphate, potassium phosphate, sodium hydrogen phosphate, disodium phosphate, sodium phosphate, calcium dihydrogen phosphate, calcium phosphate, calcium hydrogen phosphate, calcium phosphate tribasic, or hexafluorophosphate. The anionic counterion can be a phosphonate. For example, the phosphonate counterion can be vinylphosphonate, 2-carboxyethylphosphonate or phenylphosphonate. Alternatively, the anionic counterion can be nitrate. The salt can also result from the addition of the compound with an oxide such as zinc oxide.

The anionic counterion can, if desired, be bound to a polymeric resin. In other words, the anionic counterion can be a resin-bound anion. For example the resin-bound anion can be a polyacrylate resin wherein the resin contains anionic carboxylate groups. An example of a polyacrylate resin useful in the salts of the present invention is Bio-Rex 70 (produced by Bio-Rad). In an alternative example, the resin-bound anion can be a sulfonated poly (styrene divinylbenzene) copolymer resin. Non-limiting examples of sulfonated poly (styrene divinylbenzene) copolymer resins useful as anionic counterions in the present invention include Amberlite IPR-69 (Rohm & Haas) or Dowex 50WX4-400 (Dow). The polyacrylate resin or the sulfonated poly(styrene divinylbenzene) resin can be, if desired, crosslinked with a crosslinking agent such as divinylbenzene.

In another embodiment, the pharmaceutically acceptable salt of the compound of Formula 1 can be one in which the present inventive compound is in an anionic form with at least one cationic counterion. The cationic counterion can be, for example, an ammonium cation, a alkali metal cation, an alkaline earth metal cation, a transition metal cation, or a resin-bound cation. When the cationic counterion is an ammonium cation, it can be substituted or unsubstituted. For example, the ammonium cation can be an alkylammonium cation or a di-, tri-, or tetra-alkylammonium cation. Alternatively the ammonium cation can be an arylammonium or a di-, tri-, or tetra-arylammonium cation. The ammonium cation can contain both alkyl and aryl groups. The ammonium cation can be aromatic, for example a pyridinium cation. Other functional groups can also be present in the ammonium cation. The ammonium cation can be, for example, ammonium, methyl ammonium, dimethylammonium, trimethylammonium, tetramethylammonium, ethanolammonium, dicyclohexylammonium, guanidinium, or ethylenediammonium cation. Alternatively the cationic counterion can be an alkali metal cation such as lithium cation, sodium cation, potassium cation or cesium cation. In another alternative the cationic counterion can be an alkaline earth metal cation such as beryllium cation, magnesium cation, or calcium cation. The cation, if preferred, can be a transition metal cation such as zinc cation.

The cationic counterion can, if desired, be bound to a polymeric resin. In other words, the anionic counterion can be a resin-bound cation. For example, the resin-bound cation can be a cationically functionalized poly(styrene divinylbenzene) resin. An example of a cationically functionalized poly(styrene divinylbenzene) resin useful in the present invention is Bio-Rex-5 (Bio-Rad), an ammonium-functionalized resin. In another alternative, the resin-bound cation can be a cationically functionalized polyacrylic resin such as an aminated polyacrylic resin. An example of an aminated polyacrylic resin useful as the cationic counterion of the present invention is AG-4-XR (Bio-Rad).

In yet another embodiment of the present invention the compound of Formula 1 can be present in a zwitterionic form. In other words, the compound can contain both cationic and anionic sites within the molecule. Such a zwitterionic form can exist without a separate counterion or it can exist with both a cationic counterion and an anionic counterion.

Another embodiment provides a method for the treatment or prevention of an inflammation-related disorder wherein the method comprises treating a subject in need thereof with an inflammation-related disorder-treating or preventing amount of a compound or salt of the present invention.

In yet another embodiment the present invention provides a method for the preparation of a compound of Formula 21:

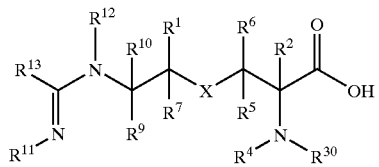

21 or a salt thereof, wherein: X is selected from the group consisting of —S—, —S(O)—, and —S(O)$_2$—; $R^2$ is selected from the group consisting of $C_1$–$C_6$ alkyl, $C_2$–$C_6$ alkenyl, $C_2$–$C_6$ alkynyl, $C_1$–$C_5$ alkoxy-$C_1$ alkyl, and $C_1$–$C_5$ alkylthio-$C_1$ alkyl; $R^{30}$ is selected from the group consisting of —H, —OH, —C(O)—$R^{17}$, —C(O)—O—$R^{18}$, and —C(O)—S—$R^{19}$; $R^1$, $R^5$, $R^6$, and $R^7$ independently are selected from the group consisting of —H, halogen, $C_1$–$C_6$ alkyl, $C_2$–$C_6$ alkenyl, $C_2$–$C_6$ alkynyl, and $C_1$–$C_5$ alkoxy-$C_1$ alkyl; $R^9$ and $R^{10}$ independently are selected from the group consisting of —H, $C_1$–$C_6$ alkyl, $C_2$–$C_6$ alkenyl, $C_2$–$C_6$ alkynyl, and $C_1$–$C_5$ alkoxy-$C_1$ alkyl; with respect to $R^{11}$ and $R^{12}$:

$R^{11}$ is selected from the group consisting of —H, —OH, —C(O)—O—$R^{24}$, and —C(O)—S—$R^{25}$; and $R^{12}$ is selected from the group consisting of —H, —OH, —C(O)—O—$R^{26}$, and —C(O)—S—$R^{27}$; or $R^{11}$ is —O—, and $R^{12}$ is —C(O)—, wherein $R^{11}$ and $R^{12}$ together with the atoms to which they are attached form a ring; or $R^{11}$ is —C(O)—, and $R^{12}$ is —O—, wherein $R^{11}$ and $R^{12}$ together with the atoms to which they are attached form a ring;

$R^{13}$ is $C_1$ alkyl;

$R^{17}$, $R^{18}$, $R^{19}$, $R^{24}$, $R^{25}$, $R^{26}$, $R^{27}$, and $R^{27a}$ independently are selected from the group consisting of —H and alkyl, which is optionally substituted by one or more moieties selected from the group consisting of cycloalkyl, heterocyclyl, aryl, and heteroaryl; and when any of $R^1$, $R^2$, $R^4$, $R^5$, $R^6$, $R^7$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{24}$, $R^{25}$, $R^{26}$, $R^{27}$, and $R^{27a}$ independently is a moiety selected from the group consisting of alkyl, alkenyl, alkynyl, alkoxy, alkylthio, cycloalkyl, heterocyclyl, aryl, and heteroaryl, then the moiety is optionally substituted by one or more substituent selected from the group consisting of —OH, alkoxy, and halogen. The present method of preparing compound 21 comprises treating a diamine compound having a structure corresponding to Formula 22:

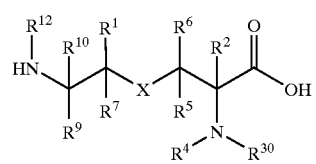

22

(or a salt thereof) with an alkyl acetimidate having a structure corresponding to Formula 23:

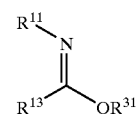

23

(or a salt thereof) wherein $R^{31}$ is $C_1$–$C_6$ alkyl. Preferably $R^{11}$ is selected from the group consisting of —H and —OH. $R^{11}$ can, for example be —H. Alternatively, $R^{11}$ can be —OH. When $R^{11}$ is —H or —OH, preferably $R^{13}$ is methyl or halomethyl. More preferably $R^{13}$ is methyl. Also when $R^{11}$ is —H or —OH, preferably $R^{31}$ is $C_1$–$C_3$ alkyl, and more preferably ethyl. In a preferred embodiment, the treating of the diamine compound with the alkyl acetimidate is performed in the presence of a base. For example, the base can be a hydrazine, a metal sulfide, a metal hydroxide, a metal alkoxide, an amine, a hydroxylamine, a metal hydride, a metal amide complex, or a basic resin. When the base is a basic resin it can be, for example a polymer-bound diazabicyclo[4.4.0]dec-2-ene resin. For example, the basic resin can have a poly(styrene divinylbenzene) copolymer backbone with diazabicyclo[4.4.0]dec-2-ene bonded to the copolymer. When the base is an amine, it can be essentially any substituted or unsubstituted amine. For example, the amine can be 1,5-diazabicyclo[4.3.0]non-5-ene; 1,4-diazabicyclo[2.2.2]octane; or 1,8-diazabicyclo[5.4.0]undec-7-ene. When the base is an alkali metal hydroxide it can be, for example, potassium hydroxide or sodium hydroxide. When the base is a metal hydride it can be, for example, sodium hydride, potassium hydride, or calcium hydride.

In a further embodiment of the present invention provides a method for the preparation of a diamine compound having a structure corresponding to Formula 22 (or a salt thereof), wherein the method comprises treating a protected diamine compound having the structure corresponding to Formula 24:

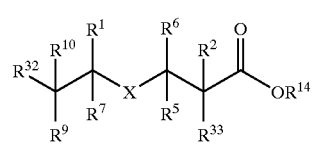

24

(or a salt thereof) wherein $R^{33}$ is selected from the group consisting of —NH$_2$ and a protected amino group; and $R^{32}$ is a protected amino group; and $R^{14}$ is selected from the group consisting of —H and $C_1$–$C_6$ alkyl; wherein when $R^{14}$ is $C_1$–$C_6$ alkyl, $R^{14}$ is optionally substituted by one or more moieties selected from the group consisting of cycloalkyl, heterocyclyl, aryl, and heteroaryl; wherein the treating is performed with a deprotecting reagent, thereby producing the diamine compound. Protected amino groups useful in the present invention vary widely in nature. Numerous protected amino groups useful in the present invention for either $R^{32}$ or $R^{33}$ are described by Theodora W. Greene and Peter G. M. Wuts (*Protective Groups in Organic Synthesis*, 3rd ed., John Wiley & Sons, New York, 1999, pp. 494–653). For example either or both of $R^{32}$ and $R^{33}$ can be a 4-chlorobenzylimino group. When $R^{33}$ is a 4-chlorobenzylimino group, preferably $R^{32}$ is —$NH_2$. In another embodiment, either or both of $R^{32}$ and $R^{33}$ can be a t-butoxycarbonylamino group. When $R^{33}$ is a t-butoxycarbonylamino group, preferably $R^{32}$ is —$NH_2$. In yet another embodiment, either or both of $R^{32}$ and $R^{33}$ can be an N-phthalimido group. When $R^{33}$ is an N-phthalimido group, preferably $R^{32}$ is —$NH_2$. In another embodiment, either or both of $R^{32}$ and $R^{33}$ can be a benzyloxycarbonylamino group. In one preferred embodiment of the present invention, the protected amino group is any such group resulting from the reaction of an aldehyde with the corresponding amino group to form a Schiff base. A large variety of deprotecting reagents can be advantageously used in the present invention to effect the conversion of 24 to 22. Many such deprotecting reagents are described by Greene and Wuts, supra. For example, when the protected amino group is a 4-chlorobenzylimino group or a t-butoxycarbonylamino group, preferably the deprotecting reagent is an acid. Some useful acid deprotecting agents include without limitation hydrochloric acid, hydrobromic acid, sulfuric acid, trifluoroacetic acid, phosphoric acid, phosphorus acid, and acetic acid. In another example, when $R^{32}$ or $R^{33}$ is an N-phthalimido group, the deprotecting reagent can be either an acid or a base. When the deprotecting reagent for the N-phthalimido group is a base, the base can be, for example, a hydrazine, a metal sulfide, a metal hydroxide, a metal alkoxide, an amine, a hydroxylamine, and a metal amide complex. When the deprotecting reagent for the N-phthalimido group is an acid, the acid can be, for example, hydrochloric acid, hydrobromic acid, hydroiodic acid, sulfuric acid, methanesulfonic acid, trifluoromethanesulfonic acid, toluenesulfonic acid, benzenesulfonic acid, trifluoroacetic acid, phosphoric acid, phosphorus acid, or acetic acid. Preferably the treating of compound 24 with the deprotecting reagent is performed in the presence of water.

In the present reaction, $R^{14}$ is preferably —H. $R^{33}$ preferably is —$NH_2$, or a salt thereof. $R^2$ is preferably methyl. In another preferred embodiment $R^1$, $R^5$, $R^6$, $R^7$, $R^8$, and $R^{10}$ each is —H. A further preferred embodiment is one in which $R^{33}$ is a t-butoxycarbonylamino group. In a particularly preferred embodiment, compound 24 has the structure corresponding to Formula 25:

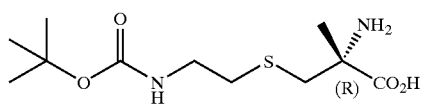

25

(or a salt thereof) wherein the parenthetical R means that the carbon alpha to the carboxylic acid function is in the Rabsolute configuration. In other words, compound 25 is the R-enantiomer or a salt thereof.

The present invention also provides a method for the preparation of the protected diamine compound 24 (or a salt thereof) wherein the method comprises treating a sulfhydryl compound having the structure of Formula 26:

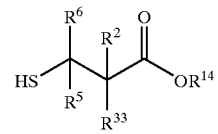

26 with a protected amino ethyl alkylating compound having the structure of Formula 27:

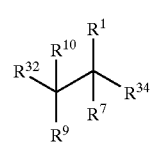

27 wherein $R^{34}$ is a nucleophilic substitution leaving group; thereby forming the protected diamine compound. Preferably, this reaction is performed in the presence of a base. The base can be, for example, a hydrazine, a metal sulfide, a metal hydroxide, a metal alkoxide, an amine, a hydroxylamine, and a metal amide complex. Preferably the base is an alkali metal hydroxide and more preferably the base is potassium hydroxide or sodium hydroxide. $R^{34}$ in the structure of Formula 27 can vary widely and can represent essentially any nucleophilic leaving group which produces either a pharmaceutically acceptable anion or an anion which can be exchanged for a pharmaceutically acceptable anion. In other words, $(R^{34})^-$ is a pharmaceutically acceptable anion or an anion which can be exchanged for a pharmaceutically acceptable anion. For example, $R^{34}$ can be chloro, bromo, iodo, methanesulfonato, toluenesulfonato, benzenesulfonato, or trifluoromethanesulfonato. Preferably $R^{34}$ is chloro, bromo, or iodo and more preferably $R^{34}$ is bromo. In the present reaction it is preferred for $R^{33}$ to be —$NH_2$. In the present reaction $R^2$ can be $C_1$–$C_6$ alkyl optionally substituted by one or more substituent selected from the group consisting of —OH, alkoxy and halogen. Preferably $R^2$ is $C_1$–$C_3$ alkyl optionally substituted by one or more substituent selected from the group consisting of —OH, alkoxy and halogen, and more preferably $R^2$ is $C_1$–$C_3$ alkyl. For example, $R^2$ advantageously can be methyl. In a further embodiment $R^5$ and $R^6$ each can be —H. In yet another embodiment $R^1$ and $R^7$ independently can be selected from the group consisting of H and $C_1$–$C_6$ alkyl optionally substituted by one or more halogen; preferably $R^1$ and $R^7$ each is —H. In the present reaction, $R^{32}$ preferably can be selected from the group consisting of a 4-chlorobenzylimino group, a t-butoxycarbonylamino group, and an N-phthalimido group, and more preferably $R^{32}$ is a t-butoxycarbonylamino group.

The present invention also provides a method for the preparation of a sulflhydryl compound having the structure of Formula 28:

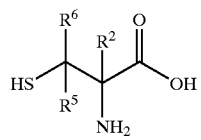

wherein $R^2$, $R^5$, and $R^6$ are as defined above, and wherein the method comprises treating under hydrolysis conditions a thiazolidine compound having the structure of Formula 29:

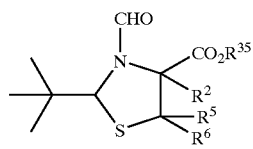

or a salt thereof, wherein $R^{35}$ is a moiety selected from the group consisting of —H and $C_1$–$C_6$ alkyl; thereby forming the sulthydryl compound. The hydrolysis conditions preferably comprise contacting the thiazolidine compound with an acid in the presence of water. Preferably the acid is selected from the group consisting of hydrochloric acid, hydrobromic acid, hydroiodic acid, sulfuric acid, methanesulfonic acid, trifluoromethanesulfonic acid, toluenesulfonic acid, benzenesulfonic acid, trifluoroacetic acid, phosphoric acid, phosphorus acid, and acetic acid. In one embodiment of the present reaction $R^5$ and $R^6$ each is —H. In another embodiment $R^2$ of compound 29 is $C_1$–$C_6$ alkyl optionally substituted by one or more substituent selected from the group consisting of —OH, alkoxy, and halogen. Preferably $R^2$ is $C_1$–$C_3$ alkyl optionally substituted by one or more substituent selected from the group consisting of alkoxy and halogen, and more preferably $R^2$ is $C_1$–$C_3$ alkyl. For example, $R^2$ can be methyl. In another embodiment of the present invention $R^{35}$ of compound 29 is methyl.

The present invention also provides a method for the preparation of a methyl thiazolidine compound having the structure of Formula 30:

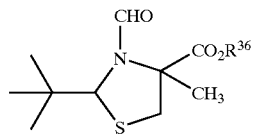

(or a pharmaceutically-acceptable salt thereof) wherein $R^{36}$ is $C_1$–$C_6$ alkyl; wherein the method comprises treating under methylation conditions a deprotonatable thiazolidine compound having the structure of Formula 31:

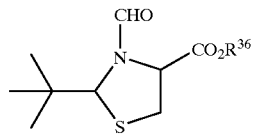

thereby forming the methyl thiazolidine compound. Preferably the methylation conditions comprise treating the deprotonatable thiazolidine compound with a base and a methylating agent. The nature of the base can vary widely. The base can be, for example, a metal hydroxide, a metal alkoxide, a metal hydride, a metal alkyl, and a metal amide complex. Preferably the base is a metal amide complex. Some metal amide complexes useful as a base in the present invention include without limitation lithium hexamethyldisilazide, sodium hexamethyldisilazide, potassium hexamethyldisilazide, lithium diisopropyl amide, sodium diisopropyl amide, potassium diisopropyl amide, sodium amide, lithium amide, potassium amide, sodium diethylamide, lithium diethylamide, potassium diethylamide, methyl lithium, t-butyl lithium, sec-butyl lithium, methyl sodium, t-butyl sodium, sec-butyl sodium, and methyl magnesium bromide. In the present methylation reaction $R^{36}$ can be $C_1$–$C_3$ alkyl; for example $R^{36}$ can be methyl.

The present invention further provides a method for the preparation of the deprotonatable thiazolidine compound 31 wherein the method comprises contacting under condensing conditions a cysteine $C_1$–$C_6$ alkyl ester with pivalaldehyde, thereby forming the deprotonatable thiazolidine compound. Preferably condensing conditions comprise performing the contacting in the presence of a base. The base can vary widely. For example the base can be, without limitation, a hydrazine, a metal sulfide, a metal hydroxide, a metal alkyl base, a metal alkoxide, an amine, a hydroxylamine, and a metal amide complex. When the base is a metal amide complex, it can be, for example, lithium bis(trimethylsilyl) amide. In the present condensation reaction it is preferred that $R^{36}$ is $C_1$–$C_3$ alkyl, and more preferably $R^{36}$ is methyl.

In another embodiment the present invention provides a method for the preparation of an alpha-amino acid compound having the structure of Formula 32:

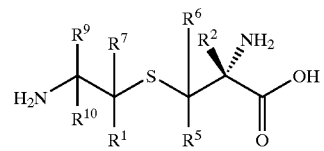

(or a salt, an enantiomer, or a racemate thereof) wherein: $R^2$ is selected from the group consisting of $C_1$–$C_6$ alkyl, $C_2$–$C_6$ alkenyl, $C_2$–$C_6$ alkynyl, $C_1$–$C_5$ alkoxy-$C_1$ alkyl, and $C_1$–$C_5$ alkylthio-$C_1$ alkyl; $R^1$, $R^5$, $R^6$, and $R^7$ independently are selected from the group consisting of —H, halogen, $C_1$–$C_6$ alkyl, $C_2$–$C_6$ alkenyl, $C_2$–$C_6$ alkynyl, and $C_1$–$C_5$ alkoxy-$C_1$ alkyl; $R^9$ and $R^{10}$ independently are selected from the group consisting of —H, $C_1$–$C_6$ alkyl, $C_2$–$C_6$ alkenyl, $C_2$–$C_6$ alkynyl, and $C_1$–$C_5$ alkoxy-$C_1$ alkyl; and when any of $R^1$, $R^2$, $R^5$, $R^6$, $R^7$, $R^9$, and $R^{10}$ independently is a moiety selected from the group consisting of alkyl, alkenyl, and alkynyl, then the moiety is optionally substituted by one or more substituent selected from the group consisting of —OH, alkoxy, and halogen; wherein the method comprises treating under hydrolyzing conditions a hydantoin compound having the structure of Formula 33:

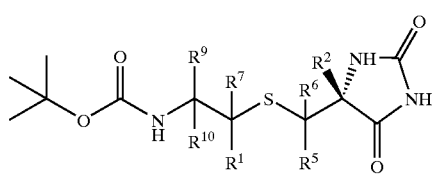

(or a salt, an enantiomer, or a racemate thereof), thereby forming the alpha-amino acid compound. The hydrolyzing conditions can comprise, for example, contacting the hydantoin compound with an acid to produce an acid hydrolyzate. Acids useful in the present hydrolysis reaction include, for example, hydrochloric acid, hydrobromic acid, hydroiodic acid, sulfuric acid, trifluoroacetic acid, or phosphoric acid. The method for the preparation of alpha-amino acid compound 32 can further comprise treating the acid hydrolyzate with an ion exchange resin. Alternatively, the hydrolyzing conditions can comprise contacting the hydantoin compound with a base to produce a base hydrolyzate. Bases useful in the present base hydrolysis include without limitation a hydrazine, a metal sulfide, a metal hydroxide, or a metal alkoxide. Whether the hydrolysis is base-mediated or acid-mediated, it is preferred that $R^1$, $R^5$, $R^6$, and $R^7$ each is —H in the structure of compound 33. It is also preferred that $R^9$ and $R^{10}$ each is —H. In a particularly preferred embodiment, the alpha-amino acid compound has the structure of Formula 34:

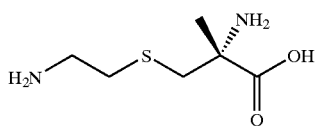

34

(or a salt, an enantiomer, or a racemate thereof).

The present invention further provides a method for the preparation of a hydantoin compound having the structure of Formula 35:

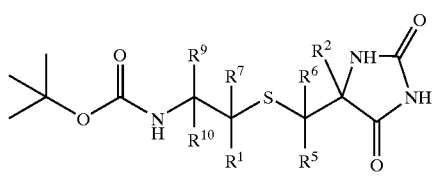

35

(or a salt, an enantiomer, or a racemate thereof) wherein $R^1$, $R^2$, $R^5$, $R^6$, $R^7$, $R^9$, and $R^{10}$ are as defined above, wherein the method comprises contacting an alpha-sulfo ketone compound having the structure of Formula 36:

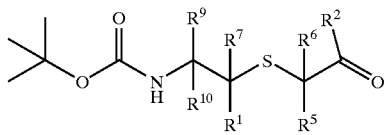

36 with a source of cyanide in the presence of a source of ammonium carbonate and water, thereby producing the hydantoin compound. The source of cyanide can be, for example, hydrogen cyanide or a metal cyanide salt. When the source of cyanide is a metal cyanide salt, preferably the salt is sodium cyanide, potassium cyanide, or lithium cyanide. More preferably the metal cyanide salt is sodium cyanide. For compound 36 in the present hydantoin-forming reaction, $R^{11}$, $R^5$, $R^6$, and $R^7$ each is preferably —H. It is further preferred that $R^9$ and $R^{10}$ each is —H. The method of preparing compound 35 can further comprise a chiral separation step. When the method of preparing compound 35 further comprises a chiral separation step, then the hydantoin compound product preferably has the structure of compound 33 (or a salt or an enantiomer thereof).

Also provided by the present invention is a method for the preparation of an alpha-sulfo ketone compound 36 wherein the method comprises contacting an aminothiol compound having the structure of Formula 37:

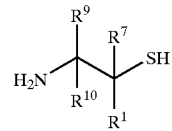

37 with di-t-butyl carbonate in the presence of a base to produce an intermediate mixture; and contacting the intermediate mixture with an alpha-chloro ketone compound having the structure of Formula 38:

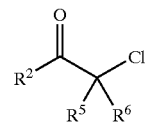

38 thereby producing the alpha-sulfo ketone compound. In the present reaction the base can vary widely. For example, the base can be without limitation a hydrazine, a metal sulfide, a metal hydroxide, a metal alkoxide, an amine, a hydroxylamine, and a metal amide complex. Preferably the base is a metal hydroxide such as sodium hydroxide, potassium hydroxide, or lithium hydroxide. In the present reaction it is preferred that $R^1$, $R^5$, $R^6$, and $R^7$ each is —H. It is further preferred that $R^9$ and $R^{10}$ each is —H.

The term "pharmaceutically-acceptable salts" embraces salts commonly used to form alkali metal salts and to form addition salts of free acids or free bases. The nature of the salt is not critical, provided that it is pharmaceutically acceptable. Pharmaceutically acceptable salts are particularly useful as products of the methods of the present invention because of their greater aqueous solubility relative to a corresponding parent or neutral compound. Such salts must have a pharmaceutically acceptable anion or cation. Suitable pharmaceutically-acceptable acid addition salts of compounds of the present invention may be prepared from inorganic acid or from an organic acid. Examples of such inorganic acids are hydrochloric, hydrobromic, hydroiodic, nitric, carbonic, sulfuric and phosphoric acid. Appropriate organic acids include from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, embonic (pamoic), methanesulfonic, ethylsulfonic, benzenesulfonic, sulfanilic, stearic, cyclohexylaminosulfonic, algenic, galacturonic acid. Suitable pharmaceutically-acceptable base addition salts of compounds of the present invention include metallic salts made from aluminum, calcium, lithium, magnesium, potassium, sodium and zinc or organic salts made from N,N'-dibenzylethylenediamine, choline, chloroprocaine, diethanolamine, ethylenediamine, meglumine (N-methylglucamine) and procain. Suitable pharmaceutically acceptable acid addition salts of the compounds of the present invention when possible include those derived from inorganic acids, such as hydrochloric, hydrobromic, boric, fluoroboric, phosphoric, metaphosphoric, nitric, carbonic (including carbonate and hydrogen carbonate anions), sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable pharmaceutically acceptable base salts include ammonium salts, alkali metal salts such as sodium and potassium salts, and alkaline earth salts such as magnesium and calcium salts. All of these salts may be prepared by conventional means from the corresponding conjugate base or conjugate acid of the compounds of the present invention by reacting, respectively, the appropriate acid or base with the conjugate base or conjugate acid of the compound. Another pharmaceutically acceptable salt is a resin-bound salt.

While it may be possible for the compounds of the present invention to be administered as the raw chemical, it is preferable to present them as a pharmaceutical composition. According to a further aspect, the present invention provides a pharmaceutical composition comprising a compound of the present invention or a pharmaceutically acceptable salt or solvate thereof, together with one or more pharmaceutically acceptable carriers thereof and optionally one or more other therapeutic ingredients. The carrier(s) must be acceptable in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. All methods include the step of bringing into association a compound of The present invention or a pharmaceutically acceptable salt or solvate thereof with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Formulations for rectal administration may be presented as a suppository with the usual carriers such as cocoa butter or polyethylene glycol.

Formulations for topical administration in the mouth, for example buccally or sublingually, include lozenges comprising the active ingredient in a flavored basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The compounds of the invention may be administered orally or via injection at a dose of from 0.001 to 2500 mg/kg per day. The dose range for adult humans is generally from 0.005 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of Formula 1 are preferably administered orally or by injection (intravenous or subcutaneous). The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

Compounds of the present invention can exist in tautomeric, geometric or stereoisomeric forms. The present invention contemplates all such compounds, including cis- and trans-geometric isomers, E- and Z-geometric isomers, R- and S-enantiomers, diastereomers, d-isomers, l-isomers, the racemic mixtures thereof and other mixtures thereof, as falling within the scope of the invention. Pharmaceutically acceptable sales of such tautomeric, geometric or stereoisomeric forms are also included within the invention.

The terms "cis" and "trans" denote a form of geometric isomerism in which two carbon atoms connected by a double bond will each have two highest ranking groups on the same side of the double bond ("cis") or on opposite sides of the double bond ("trans"). Some of the compounds described contain alkenyl groups, and are meant to include both cis and trans or "E" and "Z" geometric forms.

Some of the compounds described contain one or more stereocenters and are meant to include R, S, and mixtures of R and S forms for each stereocenter present.

The following general synthetic sequences are useful in making the present invention.

Scheme 1a

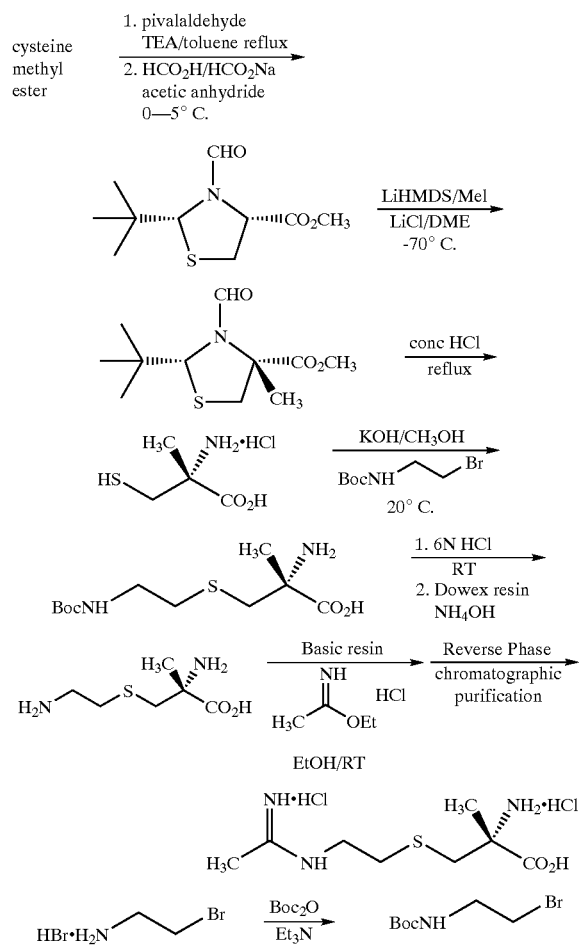

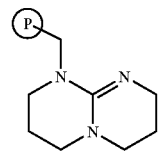

Boc = t-butoxy carbonyl
RT = room temperature
Et = ethyl
Me = methyl
Basic resin =
polymer bound triazabicyclo[4.4.0] dec-5-ene Scheme 1b

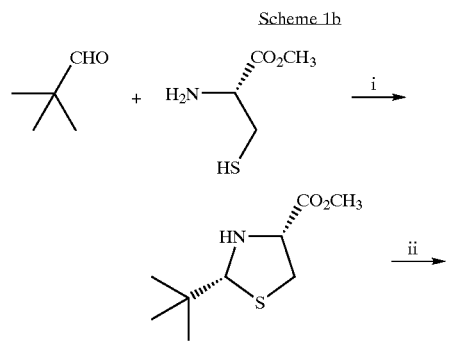

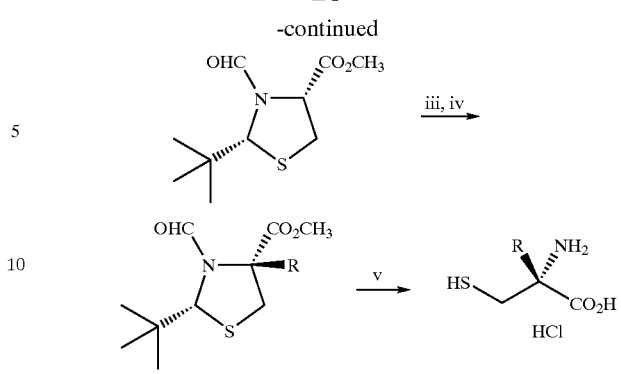

R = alkyl or alkoxyalkyl
(i) pentane with Dean-Stark trap;
(ii) HCO$_2$Na, Ac$_2$O, HCO$_2$H;
(iii) LiN[(CH$_3$)$_3$Si]$_2$, DMPU, THF -78° C.;
(iv) RI or R—SO$_3$CF$_3$;
(v) 6N HCl, reflux 2d.

Scheme 1c

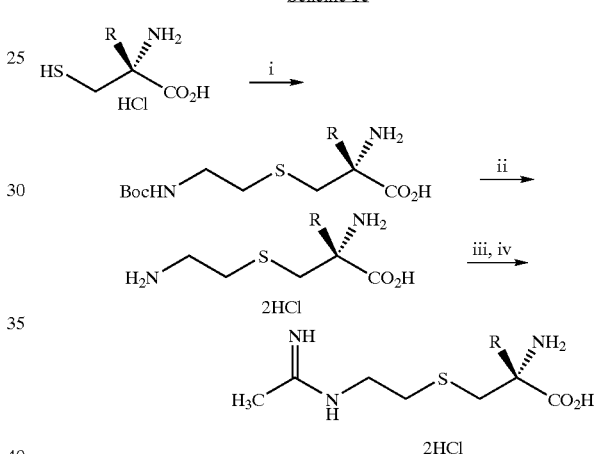

R = alkyl or alkoxyalkyl
(i) NaH, NMP, Boc—NHCH$_2$CH$_2$Br;
(ii) 1NHCl;
(iii) ethylacetimidate, NaOH;
(iv) ion exchange Scheme 2

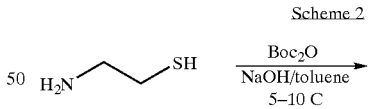

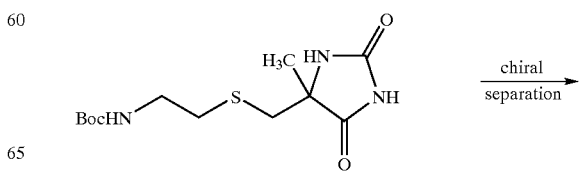

29
-continued

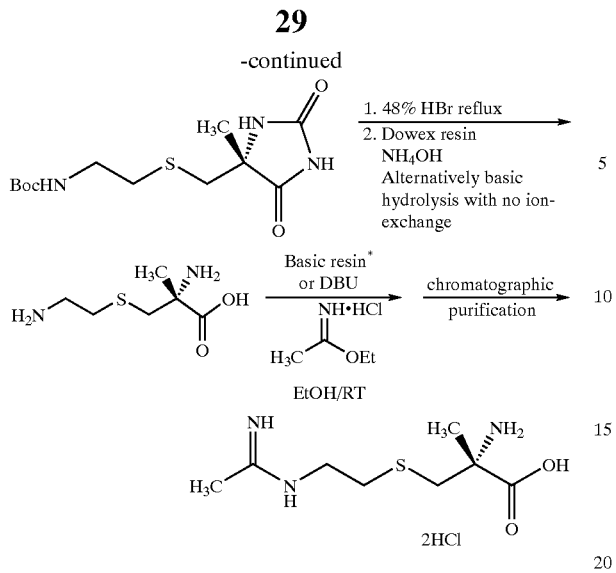

30
-continued

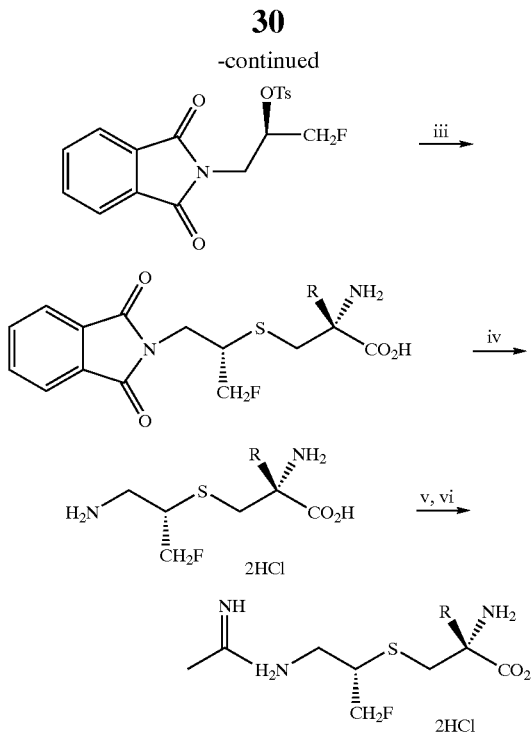

R = alkyl
(i) KHF$_2$, nBu$_4$NH$_2$F$_3$;
(ii) Toluene sulfonyl chloride, triethylamine;
(iii) 2-methyl-L-cysteine-HCl, NaH, NMP;
(iv) 6NHCl, reflux;
(v) ethylacetimidate, NaOH;
(vi) ion exchange.

Scheme 3

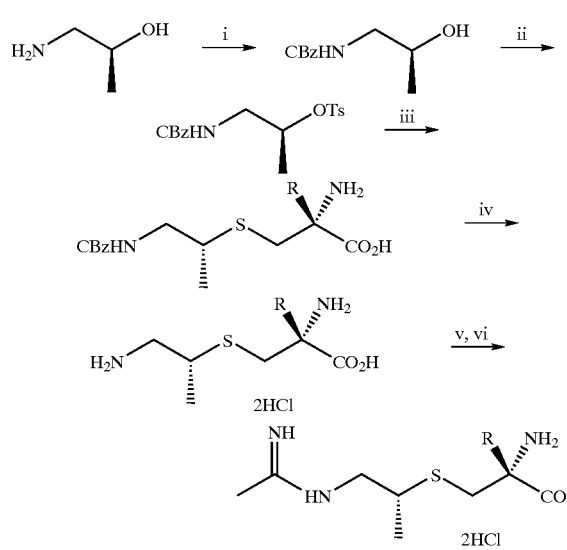

R = alkyl
(i) Benzylchloroformate, benzene;
(ii) Toluene sulfonyl chloride, triethylamine;
(iii) 2-methyl-L-cysteine-HCl, NaH, NMP;
(iv) 6NHCl, reflux;
(v) ethylacetimidate, NaOH;
(vi) ion exchange.

Scheme 5

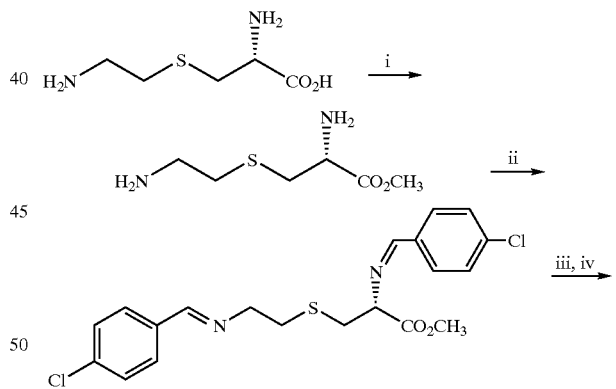

Scheme 4

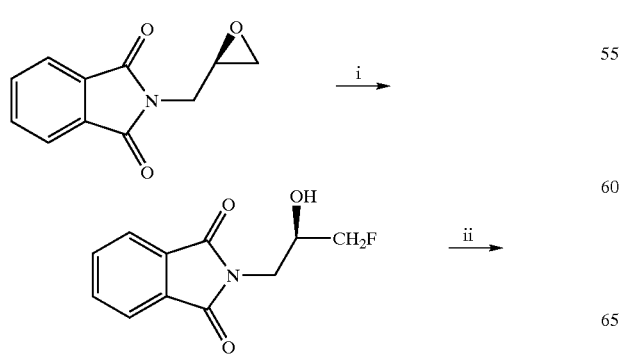

R = alkyl or alkoxyalkyl
(i) CH$_3$OH, HCl;
(ii) 4-chlorobenzaldehyde, (CH$_3$CH$_2$)$_3$N, CH$_3$CN, MgSO$_4$;
(iii) NaN[(CH$_3$)$_3$Si]$_2$, -78 C;
(iv) RI;
(v) HCl;
(vi) ethyl acetimidate, base;
(vii) ion exchange.

Scheme 6

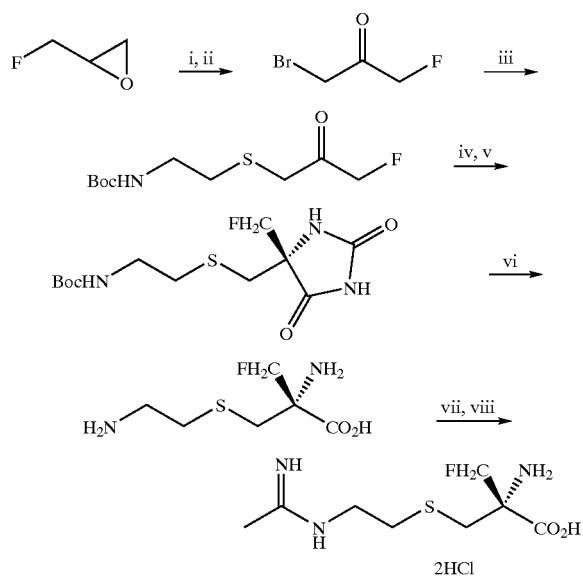

(i) HBr (Synthesis 1971 646-7, J Chem Soc 1961 3448-52);
(ii) K$_2$Cr$_2$O$_7$;
(iii) Boc-NHCH$_2$CH$_2$SH, NaOH, toluene;
(iv) NaCN, (NH$_4$)$_2$CO$_3$, EtOH;
(v) Chiral Separation;
(vi) 48% HBr;
(vii) ethyl acetimidate, base;
(viii) HCl.

Scheme 7

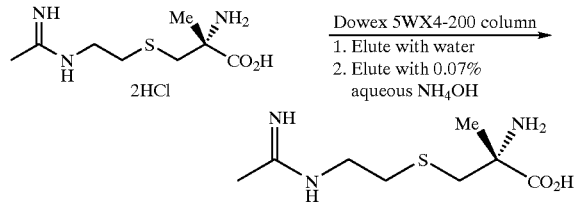

Scheme 8

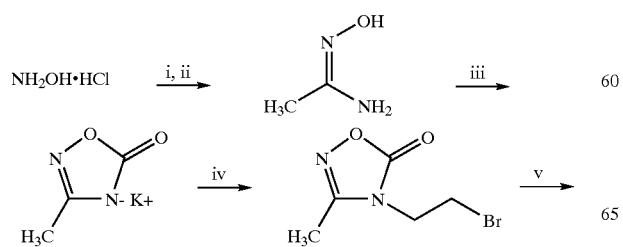

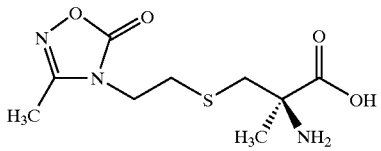

i) NaOH;
ii) acetonitrile, reflux overnight;
iii) diethyl carbonate, potassium t-butoxide;
iv) 1,2-dibromoethane, DMF;
v) NaOH, α-methyl cysteine The following structures are illustrative of the many compounds provided by the present invention. The examples provided here are not intended to be limiting and one of skill in the art, given the present disclosure, will recognize that many alternative structures are embraced by the present invention.

2
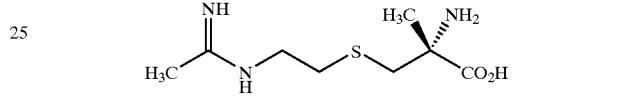

3
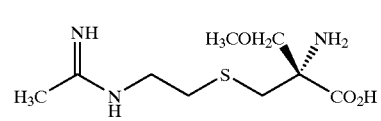

4
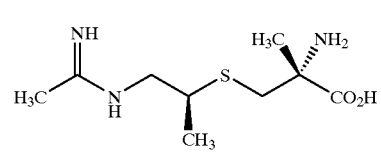

5
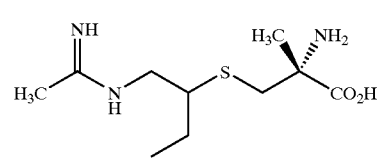

6
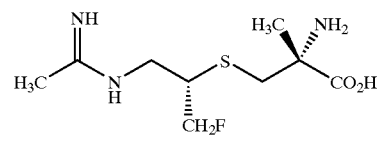

7
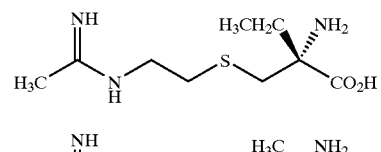

8
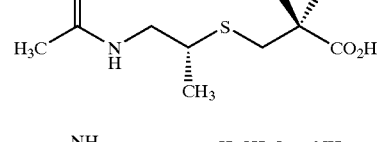

9
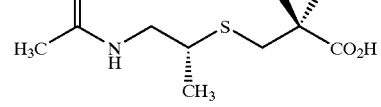

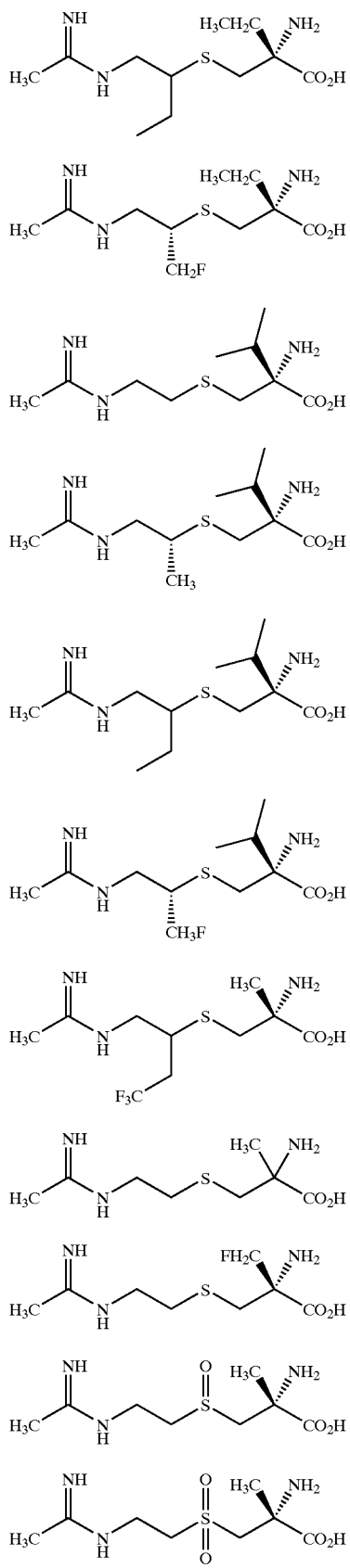

The following compounds are further examples of compounds embraced by the present invention or useful in the preparation of compounds of the present invention.

(2R,4R)-Methyl-2-tert-butyl-1,3-thiazoline-3-formyl-4-carboxylate.

(2R,4R)-Methyl-2-tert-butyl-1,3-thiazoline-3-formyl-4-methyl-4-carboxylate.

S-[2-[[(1,1-Dimethylethoxy)carbonyl]amino]ethyl]-2-methyl-L-cysteine trifluoroacetate.

(S)-1-[(Benzyloxycarbonyl)amino]-2-propanol.

(S)-1-[(Benzyloxycarbonyl)amino]-2-propanol tosylate.

S-[(1R)-2-(Benzyloxycarbonylamino)-1-methylethyl]-2-methyl-L-cysteine trifluoroacetate.

S-[(1R)-2-Amino-1-methylethyl]-2-methyl-L-cysteine hydrochloride.

S-(2-Aminoethyl)-L-cysteine, methyl ester.

N-{4-Chlorophenyl)methylene]-S-[2-[[(4-chlorophenyl)methylene]amino]ethyl]-L-cysteine, methyl ester.

N-[4-Chlorophenyl)methylene]-S-[2-[[(4-chlorophenyl)methylene]amino]ethyl]-2-methyl-D/L-cysteine, methyl ester.

The following examples are provided to illustrate the present invention and are not intended to limit the scope thereof. Those skilled in the art will readily understand that known variations of the conditions and processes of the following preparative procedures can be used to prepare these compounds.

EXAMPLE 1

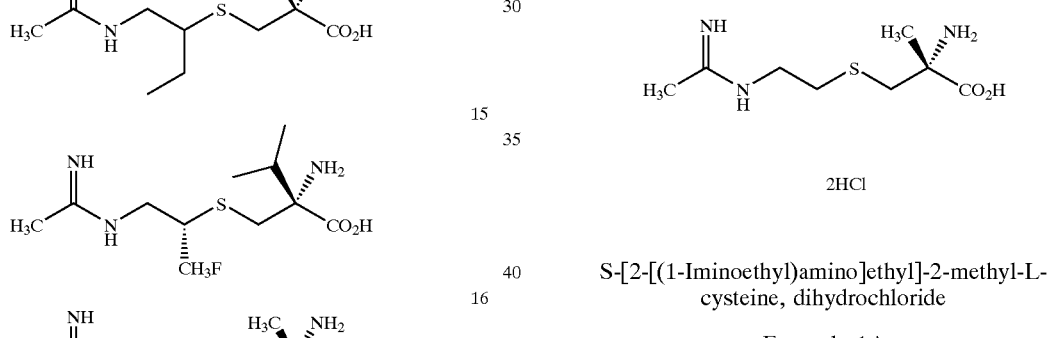

2HCl

S-[2-[(1-Iminoethyl)amino]ethyl]-2-methyl-L-cysteine, dihydrochloride

Example-1A (2R,4R)-Methyl-2-tert-butyl-1,3-thiazoline-3-formyl-4-carboxylate

See Jeanguenat and Seebach, *J. Chem. Soc. Perkin Trans. 1*, 2291 (1991) and Pattenden et al. *Tetrahedron*, 49, 2131 (1993): (R)-cysteine methyl ester hydrochloride (8.58 g, 50 mmol), pivalaldehyde (8.61 g, 100 mmol), and triethylamine (5.57 g, 55 mmol) were refluxed in pentane (800 ml) with continuous removal of water using a Dean-Stark trap. The mixture was filtered and evaporated. The resultant thiazolidine (9.15 g, 45 mmol) and sodium formate (3.37 g, 49.5 mmol) were stirred in formic acid (68 ml) and treated with acetic anhydride (13 mL, 138 mmol), dropwise over 1 hour at 0–5° C. The solution was allowed to warm to RT and stir overnight. The solvents were evaporated and the residue was neutralized with aqueous 5% NaHCO$_3$ and extracted with ether (3×). The combined organic layers were dried (anhy. MgSO$_4$), filtered, and evaporated to give the title compound which was crystallized from hexane-ether as white crystals (8.65 g) (80% overall, 8:1 mixture of conformers). $^1$H NMR (CDCl$_3$) δ major conformer: 1.04 (s, 9H), 3.29 (d, 1H), 3.31 (d, 1H), 3.78 (s, 3H), 4.75 (s, 1H), 4.90 (t, 1H), 8.36 (s, 1H). MS m/z (electrospray) 232 (M+H)$^+$ (100%), 204 (10) 164 (24).

Example-1B (2R,4R)-Methyl-2-tert-butyl-1,3-thiazoline-3-formyl-4-methyl-4-carboxylate To a solution of the product of Example-1A, (2R,4R)-Methyl-2-tert-butyl-1,3-thiazoline-3-formyl-4-carboxylate (8.65 g, 37.4 mmol), in anhydrous tetrahydrofuran (130 mL) under $N_2$ at −78° C. was added DMPU (25 mL) and the mixture stirred for 5 min. Lithium bis(trimethylsilyl)amide, 1 M in tetrahydrofuran, (37.5 mL), was added, and the mixture stirred for 30 min. After methyl iodide (5.84 g, 41.1 mmol) was added, the mixture was held at −78° C. for 4 hr and then warmed to room temperature with continuous stirring. The solvents were evaporated in vacuo and brine and ethyl acetate was added. The aqueous phase was extracted 3×EtOAc, and the combined organic layers were washed with 10% $KHSO_4$, water, and brine. They were then dried (anhy. $MgSO_4$), filtered, and stripped of all solvent under reduced pressure. Chromatography of the residual oil on silica with 1–10% EtOAc/hexane yielded the title compound (5.78 g, 63%, 2.4:1 mixture of conformers). $^1$H NMR ($CDCl_3$) δ major conformer, 1.08 (s, 9H), 1.77 (s, 3H), 2.72 (d, 1H), 3.31 (d, 1H), 377 (s, 3H), 4.63 (s, 1H), 8.27 (s, 1H); minor conformer, 0.97 (s, 9H), 1.79 (s, 3H), 2.84 (d, 1H), 3.63 (d, 1H), 3.81 (s, 3H), 5.29 (s, 1H), 8.40 (s, 1H); MS m/z (electrospray) 246 (M+H)+ (100%), 188 (55) 160 (95). Retention time of 16.5 min on a Daicel Chemical Industries Chiracel OAS column, 10–40% IPA/hexane 0–25 min, >95% ee.

Example-1C (2R) 2-Methyl-L-cysteine hydrochloride

The product of Example-1B, (2R,4R)-Methyl-2-tert-butyl-1,3-thiazoline-3-formyl-4-methyl-4-carboxylate, (5.7 g, 23.2 mmol) was stirred with 6N HCl (100 mL) under $N_2$ and held at vigorous reflux for 2 days. The solution was cooled, washed with EtOAc and evaporated to yield the product (2R) 2-methyl-cysteine hydrochloride (3.79 g, 95%) as a light yellow powder. $^1$H NMR (DMSO-$d_6$) δ 1.48 (s, 3H) 2.82 (t, 1H), 2.96 (bs, 2H), 8.48 (s, 3H). MS m/z (electrospray) 136 [M+H+].

Example-1D

S-[2-[[(1,1-dimethylethoxy)carbonyl]amino]ethyl]-2-methyl-L-cysteine trifluoroacetate Sodium hydride (2.6 g, 60% in mineral oil, 65 mmol) was added to an oven-dried, vacuum-cooled RB flask, containing oxygen-free 1-methyl-2-pyrrolidinone (5 mL). The mixture was cooled to −10° C. and stirred under $N_2$. The product of Example-1C, 2-Methyl-L-cysteine hydrochloride, (3.6 g, 21.0 mmol) dissolved in oxygen-free 1-methyl-2-pyrrolidinone (25 ml), was added in portions. After all $H_2$ evolution ceased, 2-[(1,1-dimethylethoxycarbonyl)-amino] ethyl bromide (4.94 g, 21 mmol) in oxygen-free 1-methyl-2-pyrrolidinone (15 mL) was added at −10° C. The reaction was then stirred for 4 hr allowing warming to room temperature. The solution was neutralized with 1 N HCl and the 1-methyl-2-pyrrolidinone was removed by evaporation in vacuo. Reverse-phase chromatography with 1–20% acetonitrile in 0.05% aqueous trifluoro acetic acid solution yielded the title compound (5.9 g), recovered by freeze-drying appropriate fractions. $^1$H NMR (DMSO-$d_6$/$D_2$O) δ 1.31 (s, 9H), 1.39 (s, 3H), 2.55 (m, 2H), 2.78 (d, 1H), 3.04 (d, 1H), 3.06 (t, 2H). HRMS calc. for $C_{11}H_{22}N_2O_4S$: 279.1375 (M+H+), found 279.1379.

Example-1E

S-(2-aminoethyl)-2-methyl-L-cysteine hydrochloride

The product of Example-1D, S-[2-[[(1,1-dimethylethoxy)carbonyl]amino]ethyl]-2-methyl-L-cysteine trifluoroacetate, (5.5 g, 14.0 mmol) was dissolved in 1 N HCl (100 mL) and stirred at room temperature under nitrogen overnight. The solution was removed by freeze-drying to give the title S-(2-aminoethyl)-2-methyl-L-cysteine hydrochloride, $^1$H NMR (DMSO-$d_6$/$D_2$O) δ 1.43 (s, 3H), 2.72 (m, 2H), 2.85 (d, 1H), 2.95 (t, 2H), 3.07 (d, 1H). m/z [M+H+] 179.

The product of Example-1E, was dissolved in $H_2O$, the pH adjusted to 10 with 1 N NaOH, and ethyl acetimidate hydrochloride (1.73 g, 14.0 mmol) was added. The reaction was stirred 15–30 min, the pH was raised to 10, and this process repeated 3 times. The pH was adjusted to 3 with HCl and the solution loaded onto a washed DOWEX 50WX4-200 column. The column was washed with $H_2O$ and 0.25 M $NH_4OH$, followed by 0.5 M $NH_4OH$. Fractions from the 0.5 M $NH_4OH$ wash were immediately frozen, combined and freeze-dried to give an oil that was dissolved in 1N HCl and evaporated to give the title compound as a white solid (2.7 g). $^1$H NMR (DMSO-$d_6$/$D_2$O) δ 1.17 (s, 3H), 2.08 (s, 3H), 2.52 (d, 1H), 2.68 (m, 2H), 2.94 (d, 1H), 3.23 (t, 2H). HRMS calc. for $C_8H_{18}N_3O_2S$: 220.1120 [M+H+], found 220.1133.

EXAMPLE 2

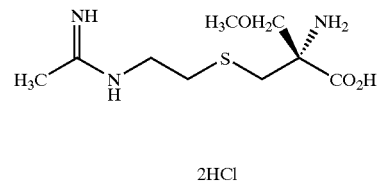

2HCl

2-[[[2-[(1-Iminoethyl)amino]ethyl]thio]methyl]-O-methyl-D-serine, dihydrochloride The procedures and methods utilized in this example were identical to those of Example 1 except that in step Example-1B methoxymethyl iodide was used instead of methyl iodide. These procedures yielded the title product as a white solid (2.7 g). $^1$H NMR ($D_2O$) δ 2.06 (s, 3H), 2.70 (m, 3H), 3.05 (d, 1H), 3.23 (s, 3H), 3.32 (t, 2H), 3.46 (d, 1H), 3.62 (d, 1H). HRMS calc. for $C_9H_{20}N_3O_3S$: 250.1225 [M+H+], found 250.1228.

EXAMPLE 3

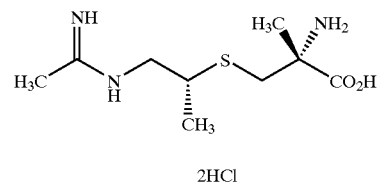

2HCl

S-[(1R)-2-[(1-Iminoethyl)amino]-1-methylethyl]-2-methyl-L-cysteine, dihydrochloride

Example-3A (S)-1-[(benzyloxycarbonyl)amino]-2-propanol

To a solution of (S)-1-amino-2-propanol (9.76 g, 130 mmol) in anhydrous benzene (60 mL) at 0° C. was added benzyl chloroformate (10.23 g, 60 mmol) in anhydrous benzene (120 mL) slowly, in portions, over a period of 20 min while vigorously stirring under an atmosphere of nitrogen. The mixture was stirred for 1 hour at 0° C., then allowed to warm to room temperature and stirred for a further 2 hours. The mixture was washed with water (2x) and brine (2x) before the organic layer was dried over anhydrous $MgSO_4$. Evaporation of all solvent gave the title product as an oil. $^1H$ NMR ($CDCl_3$) δ 1.22 (d, 3H,) 2.40 (bs, 1H), 3.07 (m, 1H), 3.37 (m, 1H)), 3.94 (m, 1H), 5.16 (s, 2H), 5.27 (m, 1H), 7.38 (m, 5H). MS m/z (electrospray) 232 $[M+23]^+$ (100%), 166 (96).

Example-3B (S)-1-[(benzyloxycarbonyl)amino]-2-propanol tosylate

To a solution of the product of Example-3A, (S)-1-[(benzyloxycarbonyl)amino]-2-propanol, (9.74 g, 46.7 mmol) and triethylamine 7.27 g, 72 mmol) in methylene chloride (60 mL) at 0° C. was added toluene sulfonyl chloride (9.15 g, 48 mmol) in methylene chloride (18 mL) slowly, in portions, over a period of 20 min while vigorously stirring under nitrogen. The mixture allowed to warm to room temperature and stirred for a further 36 hours under nitrogen. The organic layer was washed with 1N HCl, water, 5% $NaHCO_3$ solution, water and brine before it was dried over anhydrous $MgSO_4$. Evaporation of all solvent gave a white solid which was passed though a silica plug with ethyl acetate/hexane (1:4) to remove excess toluene sulfonyl chloride and then with ethyl acetate/hexane (1:3) to give the title product as white crystals. This material was recrystallized from ethyl acetate/hexane to give white needles (10.8 g). $^1H$ NMR ($CDCl_3$) δ 1.22 (d, 3H,) 2.39 (s, 3H), 3.20 (m, 1H), 3.43 (dd, 1H)), 4.66 (m, 1H), 5.02 (m, 1H), 5.04 (ABq, 2H), 7.34 (m, 7H), 7.77 (d, 2H). MS m/z (electrospray) 386 $[M+23]^+$ (100%), 320 (66). The product was examined on a Regis Technologies Inc. Perkle Covalent (R,R) β-GEM1 HPLC column using mobile phase of isopropanol/hexane and a gradient of 10% isopropanol for 5 min, then 10 to 40% isopropanol over a period of 25 min, and using both UV and Laser Polarimetry detectors. Retention time major peak: 22.2 min, >98% ee.

Example-3C

S-[(1R)-2-(Benzyloxycarbonylamino)-1-methylethyl]-2-methyl-L-cysteine trifluoroacetate The product of Example-1C, 2-methyl-L-cysteine hydrochloride, (1 g, 6.5 mmol) was added to an oven dried, $N_2$ flushed RB flask, dissolved in oxygen-free 1-methyl-2-pyrrolidinone (5 mL), and the system was cooled to 0° C. Sodium hydride (0.86 g, 60% in mineral oil, 20.1 mmol) was added and the mixture was stirred at 0° C. for 15 min. A solution of the product of Example-3B, (2S)-1-[(N-benzyloxycarbonyl)amino]-2-propanol tosylate (2.5 g, 7 mmol) dissolved in oxygen-free 1-methyl-2-pyrrolidinone (10 mL) was added over 10 min. After 15 min at 0° C., the reaction mixture was stirred at room temperature for 4.5 hours. The solution was then acidified to pH 4 with 1N HCl and 1-methyl-2-pyrrolidinone was removed by evaporation in vacuo. Reverse phase chromatography with 20–40% acetonitrile in 0.05% aqueous trifluoro acetic acid solution yielded the title compound in (0.57 g), recovered by freeze-drying. $^1H$ NMR ($H_2O$, 400 MHz) δ 1.0 (d, 3H), 1.4 (s, 3H), 2.6 (m, 2H), 2.8 (m, 1H), 3.1 (m, 2H), 3.6 (s, 1H), 5.0 (ABq, 2H), 7.3 (m, 5H). MS m/z (electrospray): 327 $[M+H^+]$ (100%), 238 (20), 224 (10), and 100 (25).

Example-3D

S-[(1R)-2-Amino-1-methylethyl]-2-methyl-L-cysteine hydrochloride

The product of Example-3C, S-[(1R)-2-(Benzyloxycarbonylamino)-1-methylethyl]-2-methyl-L-cysteine trifluoroacetate, (0.5 g, 1.14 mmol) was dissolved in 6N HCl and refluxed for 1.5 hour. The mixture was then cooled to room temperature and extracted with EtOAc. The aqueous layer was concentrated in vacuo to give the title product, (2R, 5R)-S-(1-amino-2-propyl)-2-methyl-cysteine hydrochloride (0.29 g), which was used without further purification. $^1H$ NMR ($H_2O$, 400 MHz) δ 1.2 (m, 3H), 1.4 (m, 3H), 2.7 (m, 1H), 2.8–3.2 (m, 2H), 3.4 (m, 1H). (some doubling of peaks due to rotameric forms). MS m/z (electrospray): 193 $[M+H^+]$ (61%), 176 (53), 142 (34), 134 (100), and 102 (10).

The product of Example-3D, S-[(1R)-2-Amino-1-methylethyl]-2-methyl-L-cysteine hydrochloride, (0.2 g, 0.76 mmol) was dissolved in 2 mL of $H_2O$, the pH was adjusted to 10.0 with 1N NaOH, and ethyl acetimidate hydrochloride (0.38 g, 3 mmol) was added in four portions over 10 minutes, adjusting the pH to 10.0 with 1N NaOH as necessary. After 1 h, the pH was adjusted to 3 with 1N HCl. The solution was loaded onto a water-washed DOWEX 50WX4-200 column. The column was washed with $H_2O$ and 0.5N $NH_4OH$. The basic fractions were pooled and concentrated to dryness in vacuo. The residue was acidified with 1N HCl and concentrated to the Example 3 title product, (49 mg). $^1H$ NMR ($H_2O$, 400 MHz) δ 1.3–1.0 (m, 3H), 1.5 (m, 3H), 2.1–1.8 (m, 3H), 3.4–2.6 (m, 5H), 3.6 (m, 1H) (rotamers observed). MS m/z (electrospray): 234 $[M+H^+]$ (100%), 176 (10), and 134 (10).

EXAMPLE 4

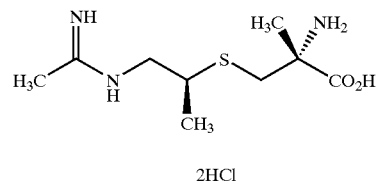

2HCl

S-[(1S)-2-[(1-Iminoethyl)amino]-1-methylethyl]-2-methyl-L-cysteine, dihydrochloride The procedures and methods employed here were identical to those of Example 3, except that in step Example-3A (R)-1-amino-2-propanol was used instead of (S)-1-amino-2-propanol to give the title material, S-[(1S)-2-[(1-Iminoethyl)amino]-1-methylethyl]-2-methyl-L-cysteine hydrochloride. $^1H$ NMR ($H_2O$, 400 MHz) δ 3.6 (m, 1H), 3.4–2.6 (m, 5H), 2.1–1.8 (m, 3H), 1.5 (m, 3H), and 1.3–1.0 (m, 3H). HRMS calc for $C_9H_{19}N_3O_2S$ $[M+H^+]$: 234.1276. Found: 234.1286.

EXAMPLE 5

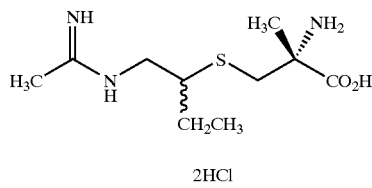

2HCl

S-[(1R/S)-2-[(1-Iminoethyl)amino]-1-ethylethyl]-2-methyl-L-cysteine, dihydrochloride The procedures and methods utilized in this synthesis are identical to those of Example 3, except that in step Example-3A (R/S)-1-amino-2-butanol is used instead of (S)-1-amino-2-propanol.

EXAMPLE 6

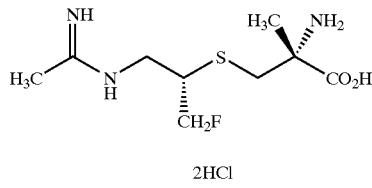

2HCl

S-[(1S)-2-[(1-iminoethyl)amino]-1-(fluoromethyl)ethyl]-2-methyl-L-cysteine, dihydrochloride A sample of 2-[(2R)-Oxiranylmethyl]-1H-isoindole-1,3-dione (G. Alexander et al. Tetrahedron Asymmetry, 7, 1641–8, 1996) is treated with potassium hydrogen difluoride to give 2-[(2R)-3-fluoro-2-hydroxypropyl]-1H-isoindole-1,3-dione in the presence of catalyst nBu$_4$NH$_2$F$_3$. The procedures and methods used in this synthesis are identical to those of Example 3, except that in step Example-3B 2-[(2R)-3-fluoro-2-hydroxypropyl]-1H-isoindole-1,3-dione is used instead of (S)-1-[(benzyloxycarbonyl)amino]-2-propanol to produce the title product.

EXAMPLE 7

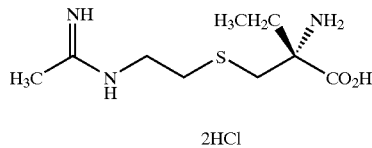

2HCl

S-[2-[(1-Iminoethyl)amino]ethyl]-2-ethyl-L-cysteine, dihydrochloride

The procedures and methods used in this synthesis were the same as those used in Example 1 except that ethyl triflate was used in Example-1B instead of methyl iodide. Reverse phase chromatography, using a gradient of 10–40% acetonitrile in water, was used to purify the title product (20% yield). $^1$H NMR (D$_2$O) δ 0.83 (t, 3H), 1.80 (m, 2H), 2.08 (s, 3H), 2.68 (m, 1H), 2.78 (m, 1H), 2.83 (m, 1H), 3.11 (m, 1H), 3.36 (t, 2H). HRMS calc. for C$_9$H$_{20}$N$_3$O$_2$S: 234.1276 [M+H$^+$], found 234.1284.

EXAMPLE 8

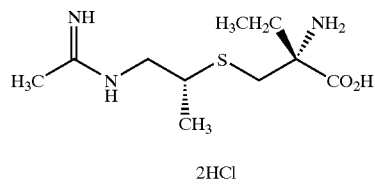

2HCl

S-[(1R)-2-[(1-Iminoethyl)amino]-1-methylethyl]-2-ethyl-L-cysteine, dihydrochloride The procedures and methods employed in this synthesis are the same as those used in Example 1 except that ethyl triflate is used in Example-1B instead of methyl iodide. The 2-ethyl-L-cysteine hydrochloride thus prepared is treated as described in the procedures and methods of Examples 3C-3E to give the title compound.

EXAMPLE 9

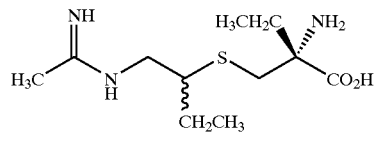

2HCl

S-[(1R/S)-2-[(1-Iminoethyl)amino]-1-ethylethyl]-2-ethyl-L-cysteine, dihydrochloride The procedures and methods utilized in this synthesis are the same as those used in Example 5 except that 2-ethyl-L-cysteine hydrochloride (prepared in Example 7) is used instead of 2-methyl-L-cysteine hydrochloride to give the title compound.

EXAMPLE 10

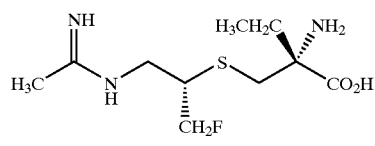

2HCl

S-[(1S)-2-[(1-iminoethyl)amino]-1-fluoromethylethyl]-2-ethyl-L-cysteine, dihydrochloride The procedures and methods utilized in this synthesis are the same as those used in Example 6, except that (2R)-2-ethyl cysteine hydrochloride (prepared in Example 7) is used instead of (2R)-2-methyl cysteine hydrochloride, to give the title compound.

EXAMPLE 11

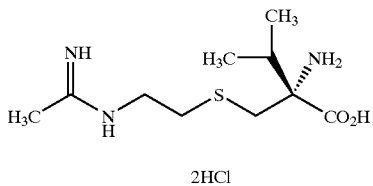

2HCl

2-[[[[2-(1-Iminoethyl)amino]ethyl]thio]methyl]-D-valine, dihydrochloride

Example-11a

Isopropyl Triflate

Silver triflate (25.25 g, 98.3 mmol) stirred in diethyl ether (300 mL) under nitrogen was treated with isopropyl iodide (16.54 g, 98.5 mmol) in ether (200 mL) over 15 minutes. The mixture was stirred for 10 minutes and then filtered. The filtrate was distilled at reduced pressure. The distillate was redistilled at atmospheric pressure to remove the majority of the diethyl ether, leaving a mixture of the title isopropyl triflate-diethyl ether (84:16 by weight) (15.64 g, 70% corrected) as a colorless liquid. $^1$H NMR (CDCl$_3$, 400 MHz) δ 1.52 (d, 6H), 5.21 (septet, 1H).

The procedures and methods utilized here were the same as those used in Example 1 except that isopropyl triflate replaced methyl iodide in Example-1B. The crude title product was purified by reversed phase chromatography using a gradient elution of 10–40% acetonitrile in water. $^1$H NMR (H$_2$O, 400 MHz) δ 0.94 (dd, 6H), 2.04 (septet, 1H), 2.10 (s, 3H), 2.65, 2.80 (d m, 2H), 2.85, 3.10 (dd, 2H), 3.37 (t, 2H). HRMS calc. for C$_{10}$H$_{22}$N$_3$O$_2$S: 248.1433 [M+H$^+$], found 248.1450.

EXAMPLE 12

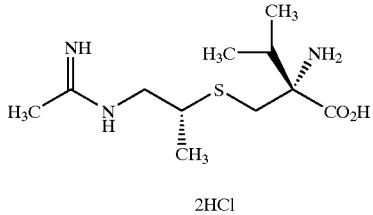

2HCl

2-[[[(1R)-2-[(1-Iminoethyl)amino]-1-methylethyl]thio]methyl]-D-valine, dihydrochloride The procedures and methods used in this synthesis are the same as those used in Example 3 except that isopropyl triflate (prepared in Example-11A) is used instead of methyl iodide to give the title compound.

EXAMPLE 13

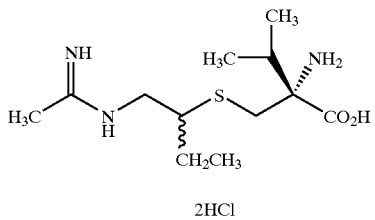

2HCl

2-[[[(1R/S)-2-(1-iminoethyl)amino)-1-ethylethyl]-thio]methyl]-D-valine, dihydrochloride The procedures and methods used in this synthesis are the same as those used in Example 5, except that (2R)-2-isopropyl triflate (prepared in Example-11A) is used instead of methyl iodide, to give the title compound.

EXAMPLE 14

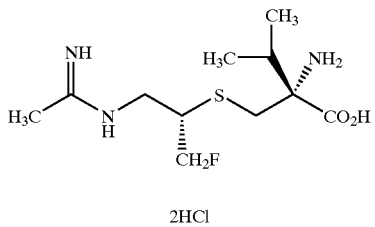

2HCl

2-[[[(1S)-2-[(1-Iminoethyl)amino]-1-fluoromethylethyl]thio]methyl]-D-valine, dihydrochloride The procedures and methods used in this synthesis are the same as those used in Example 6, except that (2R)-2-isopropyl triflate (prepared in Example-11A) is used instead of methyl iodide, to give the title compound.

EXAMPLE 15

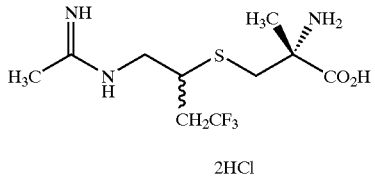

2HCl

S-[(R/S)-2-[(1-iminoethyl)amino]-1-(trifluoromethyl)ethyl]-2-methyl-L-cysteine, dihydrochloride t-Butyl-N-(2-oxoethyl)carbamate is treated with 1,1,1-trifluoroethyl magnesium bromide to give (R/S)-1-[(1,1-dimethylethoxycarbonyl)]amino-4,4,4-trifluoro-2-butanol. The procedures and methods used in this synthesis are the same as those listed in Example 3, except that (R/S)-1-[(1, 1-dimethylethoxy)carbonyl]amino-4,4,4-trifluoro-2-butanol is used instead of (S)-1-[(benzyloxycarbonyl)amino]-2-propanol, to give the title compound.

EXAMPLE 16

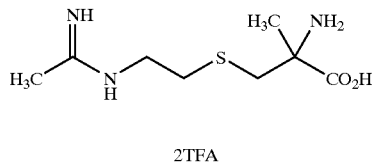

2TFA

S-[2-(1-Iminoethylamino)ethyl]-2-methyl-(D/L)-cysteine, bistrifluoroacetate

Example-16A

S-(2-aminoethyl)-L-cysteine, methyl ester

A 10 g (50 mmol) sample of S-(2-aminoethyl)-L-cysteine was dissolved in 400 mL of methanol. Into this cooled solution was bubbled in anhydrous HCl for 30 minutes. After stirring at room temperature overnight, the solution was concentrated to afford 12.7 g of the title compound.

Example-16B

N-{4-chlorophenyl)methylene]-S-[2-[[(4-chlorophenyl)methylene]amino]ethyl]-L-cysteine, methyl ester A 12.7 g (50 mmol) sample of the product of Example-16A, S-(2-aminoethyl)-L-cysteine methyl ester, was dissolved in acetonitrile. To this solution was added 12.2 g (100 mmol) of anhydrous $MgSO_4$, 14 g (100 mmol) of 4-chlorobenzaldehyde and 100 mmol of triethylamine. This mixture was stirred for 12 hours, concentrated to a small volume and diluted with 500 mL of ethyl acetate. The organic solution was washed successively with (0.1%) $NaHCO_3$, (2N) NaOH, and brine solution. The organic was dried (anhy. $MgSO_4$), filtered and concentrated to afford 7.5 g of the title compound. [M+H$^+$]=179.

Example-16C

N-[4-chlorophenyl)methylene]-S-[2-[[(4-chlorophenyl)methylene]amino]ethyl]-2-methyl-D/L-cysteine methyl ester A sample of the product of Example-16B, N-{4-chlorophenyl)methylene]-S-[2-[[(4-chlorophenyl) methylene]amino]ethyl]-L-cysteine methyl ester (7.5 g, 17 mmol), in anhydrous THF was treated with 17 mmol of sodium bis(trimethylsilyl)amide at −78° C. under nitrogen, followed by 2.4 g (17 mmol) of methyl iodide. The solution was held at −78° C. for 4 hr and then warmed to room temperature with continuous stirring. The solvents were evaporated in vacuo and brine and ethyl acetate was added. The aqueous phase was extracted 3×EtOAc, and the combined organic layers were washed with 10% $KHSO_4$, water, and brine before it was dried (anhy. $MgSO_4$), filtered, and evaporated to afford the title compound.

Example-16D

S-(2-aminoethyl)-2-methyl-D/L-cysteine, hydrochloride

A sample of the product of Example-16C, N-[4-chlorophenyl)methylene]-S-[2-[[(4-chlorophenyl) methylene]amino]ethyl]-2-methyl-D/L-cysteine methyl ester (4.37 g, 10 mmol), was stirred and heated (60° C.) with 2N HCl overnight and the solution washed (3×) with ethyl acetate. The aqueous solution was freeze-dried to give the title compound.

A sample of the product of Example-16D, S-(2-aminoethyl)-2-methyl-D/L-cysteine dihydrochloride (2.5 g (10 mmol), was dissolved in $H_2O$ and the pH was adjusted to 10 with 1 N NaOH. Ethyl acetimidate hydrochloride (1.24 g, 10.0 mmol) was then added to the reaction mixture. The reaction was stirred 15–30 min, the pH was raised to 10, and this process repeated 3 times. The pH was reduced to 4 with HCl solution and the solution evaporated. The residue was purified on reverse phase HPLC with $H_2O$ containing 0.05% trifluoroacetic acid as the mobile phase to afford the Example 16 title product. M+H=220.

EXAMPLE 17

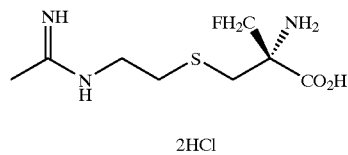

2HCl

S-[2-[(1-Iminoethyl)amino]ethyl]-2-fluoromethyl-L-cysteine, dihydrochloride

Epibromohydrin is treated with HF-pyridine to give the dihalogenated alcohol, which is oxidized with $K_2Cr_2O_7$ to give the 1-bromo-3-fluoroacetone. This product is treated with (1,1-dimethylethoxy)-N-(2-sulfanylethyl)carboxamide in the presence of NaOH to give (1,1-dimethylethoxy)-N-[2-(3-fluoro-2-oxopropylthio)ethyl]carboxamide. This is cyclized to the racemic hydantoin by NaCN and $(NH_4)_2CO_3$ in refluxing ethanol and the enantiomers separated by chiral chromatography. The S-enantiomer is treated with hot 48% HBr solution to afford S-(2-aminoethyl)-2-fluoromethyl-L-cysteine dihydrochloride, which is converted to the title compound by treatment with ethyl acetimidate in the presence of base.

EXAMPLE 18

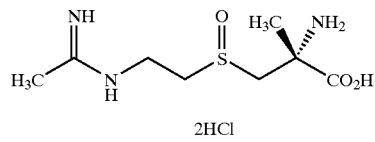

2HCl (2R)-2-Amino-3[[2-[(1-iminoethyl)amino]ethyl] sulfinyl]-2-methylpropanoic acid, dihydrochloride A solution of S-[2-[(1-iminoethyl)amino]ethyl]-2-methyl-L-cysteine, dihydrochloride (Example 1, 0.2 g, 0.73 mmol) in 3 mL of water was stirred and cooled to 0° C. and a solution of 3% $H_2O_2$ (0.8 mL, 0.73 mmol) in formic acid (0.4 mL, 0.73 mmol) was added in 0.3 mL portions. The cold bath was removed and the reaction mixture was stirred at room temperature for 48 hours. The solution was concentrated in vacuo, diluted with of water (10 mL) and concentrated again to give the crude sulfone. This residue was chromatographed (C-18 reverse phase, with mobile phase $H_2O$ containing 0.05% trifluoroacetic acid) to give the pure sulfone. The sulfone was treated with 1M HCl (10 mL) and concentrated in vacuo to give 140 mg of a mixture of 2 diastereomers of the title compound as a colorless oil of the HCl salts. $^1$H NMR (300 MHz, D$_2$O) δ 1.5 (s, 2H), 1.6 (s, 1H), 2.0 (s, 3H), 3.1 (m, 2H), 3.3 (m, 2H) 3.6 (m, 2H). HRMS calc. for C$_8$H$_{18}$N$_3$O$_3$S: 236.1069 [M+H$^+$], found: 236.1024.

EXAMPLE 19

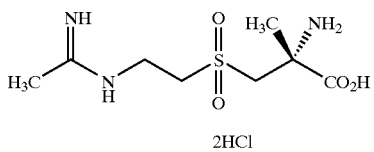

2HCl (2R)-2-Amino-3[[2-[(1-iminoethyl)amino]ethyl]sulfonyl]-2-methylpropanoic acid dihydrochloride A solution of S-[2-[(1-Iminoethyl)amino]ethyl]-2-methyl-L-cysteine dihydrochloride, the product of Example 1, (0.15 g, 0.54 mmol) in 2 mL of water was cooled to 0° C. and a solution of 3% H$_2$O$_2$ (1.6 mL, 1.46 mmol) in formic acid (0.8 mL, 14.6 mmol) was added. The cold bath was removed and the reaction mixture was stirred at room temperature for 18 hours. The solution was concentrated in vacuo, diluted with 10 mL of water and concentrated again to give the crude sulfoxide. The residue was diluted with 4 mL of water and was adjusted to pH 9 with 2.5 N NaOH. Acetone (5 mL) was added, followed by Boc$_2$O (0.2 g), and the reaction was stirred for 48 h at room temperature. The reaction mixture was adjusted to pH 6 with 1M HCl and was concentrated in vacuo. This residue was chromatographed (C-18 reverse phase; 40 to 50% ACN: H$_2$O, 0.05% TFA) to give the pure Boc protected material. The fractions were concentrated in vacuo and the residue was treated with 1N HCl (3 mL) for 1 h. The solution was concentrated to give 30 mg of the title compound as colorless oil. $^1$H NMR (400 MHz, D$_2$O) δ 4.0 (d, 1H), 3.7 (d, 1H), 3.6 (t, 2H), 3.5 (t, 2H), 2.1 (s, 3H), and 1.5 (s, 3H) ppm. HRMS calc. for C$_8$H$_{18}$N$_3$O$_4$S: 252.1018 [M+H$^+$], found: 252. 0992.

EXAMPLE 20

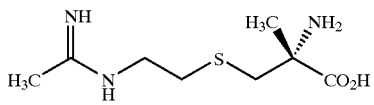

S-[2-[(1-Iminoethyl)amino]ethyl]-2-methyl-L-cysteine

DOWEX 50WX4–200 (250 g) in a glass chromatography column (38×560 mm) was washed with water until the eluent was at pH 6. An solution of the product of Example 1, S-[2-[(1-Iminoethyl)amino]ethyl]-2-methyl-L-cysteine dihydrochloride (6 g) dissolved in water was placed on the column, which was washed with water until the pH returned to 6. The column was then washed with 0.07 M NH$_4$OH (flow rate 15 mL/min) and the basic fractions were immediately placed in a dry ice/acetone bath. The fractions were pooled and concentrated to dryness by lyophilization to give the title compound. $^1$H NMR (400 MHz, DMSO-d$_6$) δ 3.4 (m, 1H), 3.3 (m, 1H), 3.0 (d, 1H), 2.7 (m, 11H), 2.4 (m, 1H), 2.1 (s, 3H), and 1.1 (s, 3H).

Analysis calculated for C$_8$H$_{17}$N$_3$O$_2$S+0.6H$_2$O: C, 41.76; H, 7.97; N, 18.26; found C, 41.43; H, 7.47; N, 17.96; Cl, trace.

EXAMPLE 21

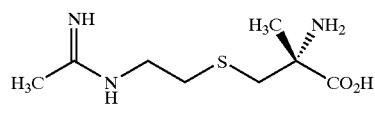

2HCl

S-[2-[(1-Iminoethyl)amino]ethyl]-2-methyl-L-cysteine, dihydrochloride

Example-21A (2R,4R)-Methyl-2-tert-butyl-1,3-thiazoline-3-formyl-4-carboxylate

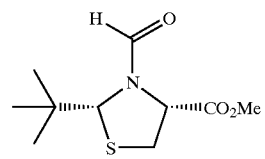

The title material was prepared according to J. Chem. Soc. Perkin Trans. 1991 p 2291 and Tetrahedron 1993 p 2131. To a 2 L RB flask fitted with a reflux condenser, a Dean-Stark trap, an overhead stirrer and a thermocouple was added pivalaldehyde (23.7 g, 0.275 mole) dissolved in 700 mL of toluene. Agitation was started and L-cysteine hydrochloride methyl ester (45 g, 0.262 mole) was added to the stirring solution. Triethylamine (29.2 g, 0.288 moles) was then added to the batch in a stream over a few minutes. The reaction mixture was heated to reflux and water was removed. The batch was heated for a total of 3h, cooled and filtered. The salt cake was washed with 250 mL of fresh toluene and the wash was combined. Formic acid (24.1 g, 0.524 moles) and solid sodium formate (19.6 g, 0.288 moles) were then added and the resulting suspension was cooled to –5° C. Acetic anhydride (53.5 g, 0.524 moles) was carefully added to the mixture keeping the batch temperature below 5° C. After the addition, the reaction was allowed to warm to room temperature and stirring continued for 18h during which time the product precipitated. The crude product was filtered and redissolved in 400 mL of EtOAc and filtered to remove insoluble sodium salts. The organic solution was then neutralized with 200 mL of saturated sodium bicarbonate solution and the final aqueous layer was near pH 7. The organic layer was separated and the aqueous layer was extracted with ethyl acetate. The organic layers were combined and concentrated to give the crude product (60.2 g) as a viscous oil which slowly crystallized to a white solid. The solid was washed with cyclohexane containing 4% of 2-propanol to give 41.01 g of the title product in >99.5% purity and 67.8% yield as determined by GC. The desired title product cis isomer was present in over 98%.

Example-21B (2R,4R)-Methyl-2-tert-butyl-1,3-thiazoline-3-formyl-4-methyl-4-carboxylate

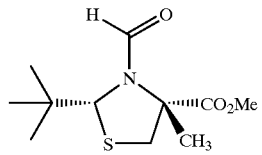

Anhydrous lithium chloride (43.0 g, 0.102 moles) was mixed with 300 mL of dimethoxyethane and 500 mL of THF until a clear solution was obtained. A THF solution of the product of Example-21A (50.0 g, 0.216 moles) was added and cooled to −65° C. under a nitrogen atmosphere. Iodomethane (45.0 g, 0.316 moles) diluted with 45 mL of THF was added followed by 230 mL of 1.0M THF solution of lithium bis-trimethylsilylamide. The reaction was stirred at −65° C. for 10 h. The batch was quenched with 30 g of acetic acid in 600 mL water and extracted with 500 mL of ethyl acetate. The organic layer was washed with saturated sodium bicarbonate and concentrated to give 51.22 g (96%) of the title product as a light brown solid.

Example-21C (2R) 2-Methyl-L-cysteine hydrochloride

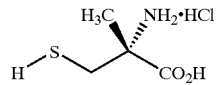

A sample of the product of Example-21B (20 g, 83 mmoles) was placed in a round bottom flask equipped with an overhead stirrer and reflux condenser. To this solid was added 100 mL of concentrated hydrochloric acid. The reaction was slowly heated to 95° C. for 7 days. The reaction was then treated with 250 mL of toluene to remove non-polar organic impurities. The aqueous solution was then concentrated. The crude title product was obtained as an orange resin weighing 14 g. The resin was powdered up under ethylether/methylene chloride and filtered to give 13 g of the title material as a pale brown hygroscopic powder. $^1$H NMR (D$_2$O) δ 4.70 (s, HDO exchange), 3.08 (d, 1H), 2.80 (d, 1H), 1.48 (s, 3H).

Example-21D

2-[(1,1-dimethylethoxycarbonyl)-amino]ethyl bromide

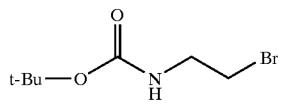

A 5L RB flask equipped with overhead stirrer, thermocouple and nitrogen inlet was charged with 3 liters of ethyl acetate and agitation started. To this was added di-tert-butyldicarbonate (545 g, 2.50 moles) and 2-bromoethylamine hydrobromide (553.7 g, 2.70 moles) under a nitrogen blanket. The batch was cooled to 5° C. in an ice bath and N-methylmorpholine, (273 g, 2.70 moles) was added dropwise over ca. 0.5 h. After the addition was complete, the batch was allowed to stir overnight and warm to ambient temperature. After 16h, the batch was quenched by adding 1.5L of DI water. The organic layer was washed with dilute HCl, sodium bicarbonate solution followed by brine. The dried organic solution had solvents removed to give an oil that froze to a light yellow solid. A total of 496 g (88% yield) of the title product was obtained in approx. 96% purity.

Example-21E

S-[2-[[(1,1-dimethylethoxy)carbonyl]amino]ethyl]-2-methyl-L-cysteine acetate

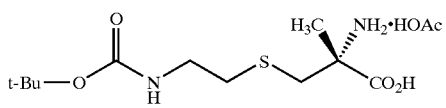

A 3 L flask, charged with 435 g of methanol, was equipped with an overhead stirrer, a thermocouple, and maintained under a N$_2$ purge. To the reaction flask was added 150.0 g (0.804 moles) of the product of Example-21C carefully with stirring to dissolve. A solution of KOH prepared by dissolving 154.7 g of solid KOH in 840 mL of degassed methanol was added to the reaction solution dropwise keeping the temperature between 20–30° C. The product of Example-21C (180.2 g, 0.804 moles) was dissolved in 375 mL of methanol and this solution was added dropwise to the cold reaction mixture over 1 hour at 10–12° C. When the reaction was complete, the batch had its pH adjusted to pH 5. The reaction mixture was then filtered through a pad of Celite and the filtrate was concentrated to yield 454 g of a tan solid product. This title product was slurried with ethyl acetate to give an off-white solid weighing 299 g. The crude title product solid was carried on to the next step without further purification. $^1$H NMR as acetate (D$_2$O) δ 4.68 (s, D$_2$O exchange), 3.12 (m, 3H), 2.68 (m, 3H), 1.83 (s, 3H), 1.42 (s, 3H), 1.32 (s, 9H).

Example-21F

S-(2-aminoethyl)-2-methyl-L-cysteine

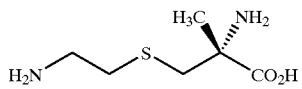

To a round bottom flask equipped with an overhead stirrer and nitrogen purge was added 150 mL of 37% hydrochloric acid. The agitator was started and 150 mL of water was added to the vessel followed by 173 g of crude product of Example-21E. The reaction was stirred for two hours and the clear brown solution batch was concentrated to give the crude di-HCl salt of the title product as a brown syrup (ca.157 g). This was redissolved in 200 mL of water and decolorized with charcoal. The solution was passed through a Dowex resin column and the neutral title product was eluted with aqueous ammonium hydroxide to yield 64% of this material with approx. 94% purity. $^1$H NMR (D$_2$O, 300 MHz) δ 4.68 (s, D$_2$O exchange), 2.9 (m, 3H), 2.6 (m, 3H), 1.20 (s, 3H).

Polymer bound triazabicyclo[4.4.0] dec-5-ene resin (Fluka), 38 g, was suspended in 160 mL of ethanol in a round bottom flask. The amino acid product of Example-21F (7.5 g) in 40 mL of ethanol was added to the stirring resin slurry. Ethyl acetimidate, 6.5 g (53 mmoles) was added portion-wise to the reaction. The reaction was stirred under nitrogen for 16h. The resin was filtered and washed on the filter with 100 mL of ethanol containing 10 mL of conc. HCl. The combined filtrate was concentrated to give 12 g of crude title product as a pale brown viscous semisolid. The yield was approximately 60–70% and the title product showed 90% purity. The title product was further purified by reverse phase chromatography. $^1$H NMR (D$_2$O) δ 4.74 (s, D$_2$O exchange), 3.37 (t, 2H), 3.08 (d, 1H), 2.93 (d, 1H), 2.74 (m, 2H), 2.06 (s, 3H), 1.48 (s, 3H).

EXAMPLE 22

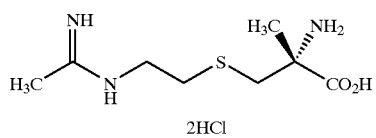

2HCl

S-[2-[(1-Iminoethyl)amino]ethyl]-2-methyl-L-cysteine, dihydrochloride

Example-22A

N-Boc-cysteamine

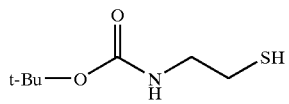

A 3L 4-neck RB flask was purged with nitrogen for 20 min and then charged sequentially with 2-aminoethanethiol hydrochloride (113.6 g, 1 mol), di-tert-butyl-dicarbonate (218.3 g, 1 mol) and 500 mL of toluene. The mixture was cooled with an ice-water bath and purged with nitrogen for 10 min. Sodium hydroxide (2.5N, 880 mL, 2.2 mol) was added to the stirring mixture in about 1.5 h at between 0 and 11° C. After the addition of sodium hydroxide was complete, the cooling bath was removed and the resulting reaction mixture was allowed to warm up to room temperature and stirred at ambient temperature overnight. This provided a solution of the title product.

Example-22B

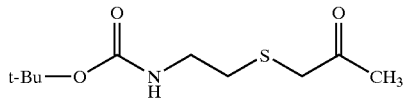

The product solution of Example-22A was cooled with an ice-water bath. A sample of chloroacetone (101.8 g, 1.1 mol) was added to the vigorously stirred reaction mixture over about 50 min at between 8 and 11° C. After the addition of chloroacetone was completed, the cooling bath was removed and the resulting reaction mixture was allowed to stir at room temperature overnight. The toluene layer was separated, washed with water (250 mL) and concentrated on a rotary evaporator at 85° C. under house vacuum followed by high vacuum to give the crude titled compound (225.7 g, 96.7%). $^1$H NMR (CDCl$_3$, 400 MHz) δ 4.95 (bs, 1H), 3.20 (m, 4H), 2.54 (t, 2H), 2.20 (s, 3H), 1.35 (s, 9H).

Example-22C

[2-[[(4-Methyl-2,5-dioxo-4-imidazolidinyl)methyl]thio]ethyl]carbamic acid, 1,1-dimethylethyl ester

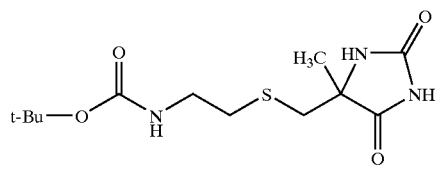

To a 3L 4-neck RB flask equipped with an overhead stirrer, a thermocouple and a condenser connected to an empty flask and a caustic trap, was added the product of Example-22B (70 g, 0.3 mol), absolute ethanol (80 mL), sodium cyanide (19.1 g, 0.39 mol), ammonium carbonate (43.3 g, 0.45 mol) and water (720 mL) in this order. The 4$^{th}$ neck was closed with a stopper. The resulting reaction mixture was heated at between 67 and 68° C. for 6 h. Subsequently, the almost clear brown solution was cooled to room temperature. Upon cooling, solid began to form and the heterogeneous mixture was stirred at room temperature overnight. The reaction mixture was then acidified with 12% hydrochloric acid to pH 2 in about 1 h at between −2 and 2° C. The cold reaction mixture was stirred at pH2 for additional 30 min and then filtered. The flask was rinsed with distilled water (2×250 mL) and each rinse was used to wash the solid cake. The solid was again washed with distilled water (2×250 mL) and then air-dried for 4 days. The dry solid was triturated with 200 mL of toluene for 0.5 h. The slurry was filtered. The solid was rinsed sequentially with toluene (50 mL) and 1:4 ratio of toluene/hexane (100 mL) and then air-dried at room temperature overnight to give 83.1% yield of the titled compound, m.p. 134–136° C. $^1$H NMR (DMSO$_{d6}$, 400 MHz) δ 10.62 (s, 1H), 7.85 (s, 1H), 6.83 (m, 0.9H), 6.48 (bs, 0.1H), 3.29 (s, 2H), 2.99 (m, 2H), 2.71 (s, 2H), 2.95 (m, 2H), 1.32 (s, 9H), 1.24 (s 3H); $^{13}$C NMR (DMSO$_{d6}$, 400 MHz), δ 178.1, 157.1, 156.1, 78.4, 63.7, 40.7, 39.4, 33.2, 28.9, 23.8. Analysis Calcd for C$_{12}$H$_{21}$N$_3$O$_4$S: C, 47.51; H, 6.98; N, 13.85; S, 10.57. Found: C, 47.76; H, 6.88; N, 13.77; S, 10.75.

Example-22D

R and S-[2-[[(4-Methyl-2,5-dioxo-4-imidazolidinyl)methyl]thio]ethyl]carbamic acid, 1,1-dimethylethyl ester

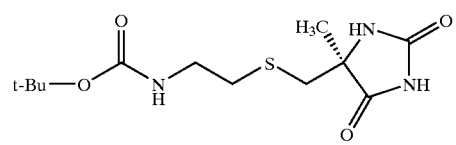

S enantiomer

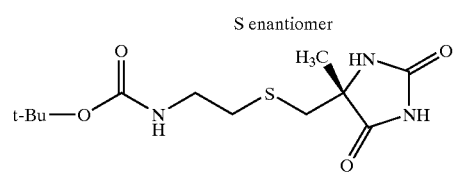

R enantiomer

The reaction product of Example-22C was separated into its R and S enantiomers on a Chiralpak® AD column eluting with methanol. The S isomer was the first eluting isomer followed by its R enantiomer. Both isomers were used in subsequent transformations.

S Enantiomer:

[α]in MeOH at 25° C.=+43.0 (365 nm). $^1$HNMR: (400 mHz, CD$_3$OD) δ 1.49 (s, 9H), 2.05 (s, 3H), 2.65 (t, 2H), 2.9 (q, 2H, d), 3.20 (m, 2H). IR: λcm$^{-1}$=1772, 1709.

Analysis calculated for $C_{12}H_{21}N_3O_4S$ (formula weight=303.38): C, 47.51; H, 6.98; N, 13.85. Found: C, 47.39; H, 6.62; N, 13.83. M+H=304.

R Enantiomer:

[α]in MeOH at 25° C.=−46.3 (365 nm). $^1$HNMR: (400 mHz, CD$_3$OD) δ 1.48 (s, 9H), 2.05 (s, 3H), 2.65 (t, 2H), 2.85 (q, 2H, d), 3.18 (m, 2H). IR: ?cm$^{-1}$=1770, 1711.

Analysis calculated for $C_{12}H_{21}N_3O_4S$ (formula weight=303.38): C, 47.51; H, 6.98; N, 13.85. Found: C, 48.15; H, 7.04; N, 14.37. M+H=304.

Example-22E

S-(2-aminoethyl)-2-methyl-L-cysteine

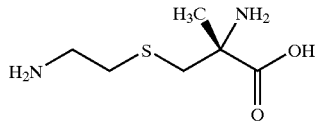

Acid Hydrolysis Method:

A 500 mL three-necked round bottom flask equipped with a distillation condenser was charged with the R-isomer product of Example-22D (45.8 g, 150.9 mmol) and treated portion wise with 48% aq. HBr (160 mL) at room temperature with stirring. After the gas evolution ceased, the mixture was heated with a heating mantle until the pot temperature reached to 126° C. while the volatile t-butyl bromide (bp 72–74° C.) followed by a small amount of aq. HBr (approx. 15 mL) were distilled off. The distillation condenser was replaced with a reflux condenser and the mixture was heated at reflux for 30 hours. The solution was concentrated and the residue was dissolved in water (250 mL) and loaded on to a Dowex® 50WX4-200 ion-exchange resin (8.5×11 cm) and eluted with water (2L) followed by dilute aqueous ammonium hydroxide (30 mL of 28–30% ammonium hydroxide diluted to 1000 mL with water, 3L). Fractions containing the desired product were combined, concentrated, and dried under vacuum at 75–80° C. for two hours to give 22.1 g (82%) of the title product, S-(2-aminoethyl)-2-methyl-L-cysteine, as a white solid. Proton and C-13 NMR spectra are consistent with the title product. Mp 157° C. $^1$H NMR (400 MHz, D$_2$O) δ 1.19 (3H, s), 2.53 (1H, d, J=13.6 Hz), 2.57–2.72 (2H, nm), 2.92 (1H, d, J=13.6 Hz), 2.92 (2H, t, J=6.8 Hz); $^{13}$C NMR (100 MHz, D$_2$O) δ 24.7, 31.3, 38.9, 40.9, 59.6, 180.7.

Analysis Cald for $C_6H_{14}N_2O_2S+0.1H_2O$: C, 40.02; H, 7.95; N, 15.56; S, 17.81. Found: C, 39.93; H, 7.98; N, 15.38; S, 17.70.

Base Hydrolysis Method:

To a stainless steel autoclave equipped with agitation was added 24.2 g (0.08 moles) of the R-isomer product of Example-22D. After purging the apparatus with nitrogen, 128 g (0.32 moles) of 10% caustic was added generating a solution. The autoclave was sealed and heated to 120° C. for 30 hours. After cooling to room temperature, the autoclave was vented to give 142 ml (151 g) of an aqueous solution of the sodium salt of the title product. H$^1$NMR (sample acidified with HCl and diluted with D$_2$O, 400 MHz): δ 1.47 (s,3H), 2.75 (m, 2H), 2.90 (d,1H, J=14.8 Hz), 3.06 (t, 2H, J=6.4 Hz), 3.14 (d, 1H, J=14.8 Hz). C$^{13}$NMR (sample acidified with HCl and diluted with D$_2$O, 100 MHz): δ 172.9, 60.8, 39.1, 39.0, 30.4, 22.2. MS (MS/CI-LC) M+1179.

DBU (218 μL; 1.46 mmol) and ethyl acetimidate hydrochloride (171 mg; 1.34 mmol) were dissolved in ethanol (6 mL) in a 25 mL, one-necked, round-bottomed flask at room temperature (~20° C.). The title product of Example-22E (200 mg; 1.12 mmol) was added in one portion to this solution. The mixture was stirred until the title product of Example-22E was consumed (1–2 hours). The mixture was chilled with an ice-bath and then treated with 6 M HCl (830 μL). $^1$HNMR analysis indicated a chemical yield of 95 mole % or better. The solvent was evaporated and the title product of Example-22 was purified by reverse-phase or ion-exchange chromatography.

A 210 gm solution (containing ~20 g of the title product of Example-22E of the base hydrolysis reaction product was put into a 500 mL, three-necked, round-bottomed flask. The apparatus was equipped with a mechanical stirrer, a Dean-Stark apparatus (20 mL with a stopcock), a condenser, and a temperature controller. Water (140 mL) was distilled off from the mixture. 1-butanol (150 mL) was added to the pot and the remaining water (37 mL) was distilled azeotropically. Additional 1-butanol (13 mL) was removed by distillation until the pot temperature reached 117° C. The butanol slurry was cooled to room temperature and filtered through a pad of celite. The salts were washed with l-butanol (2×20 mL). DBU (21.8 μL; 146 mmol) and ethyl acetimidate hydrochloride (17.1 mg; 134 mmol) were dissolved in 1-butanol (40 mL) in a 500 mL, three-necked, round-bottomed flask at room temperature. The apparatus was equipped with a mechanical stirrer, an addition funnel, and a temperature probe. The title product of Example-22E/1-butanol solution was put into the addition funnel and added to the ethyl acetimidate/DBU solution while maintaining the pot temperature below 25° C. The mixture was stirred until the starting material was consumed (2–3 hours). A solution of conc. HCl (94 mL) and water (100 mL) was put into a 1 L, three-necked, round-bottomed flask and chilled to 0° C. The apparatus was equipped with a mechanical stirrer, an addition funnel, and a temperature probe. The reaction mixture was put into the addition funnel. The reaction mixture was added to the aqueous HCl solution while maintaining the temperature below 25° C. Ethyl acetate (100 mL) was added to the solution and the layers were separated. The aqueous layer was washed once more with ethyl acetate (100 mL). $^1$HNMR analysis indicated a chemical yield of 95 mole % or better. This title product of Example-22 was purified by reverse-phase or ion-exchange chromatography.

$^1$HNMR (400 MHz, D$_2$O) δ 1.49 (3H, s), 2.08 (3H, s), 2.74 (2H, m), 2.91 (1H, d), 3.17 (1H, d), 3.35 (2H, t).

EXAMPLE 23

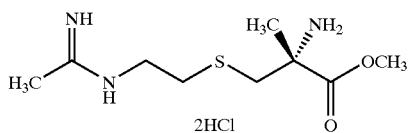

S-[2-[(1-Iminoethyl)amino]ethyl]-2-methyl-L-cysteine methyl ester, dihydrochloride The product of Example 22 (1.0 g, 3.42 mmol) dissolved in anhydrous methanol (40 ml) was added to a 500 ml 3 neck round bottom flask equipped with a magnetic stirrer and a thermocouple. This reaction under nitrogen was cooled to 0° C. HCl gas was bubbled into the reaction solution for 1 minute. The reaction mixture was allowed to warm to room temperature and continued to stir overnight. A sample was taken from the reaction mixture and concentrated. NMR and Mass Spectrometry indicated starting material and product. The solvent was stripped and the oily residue was re-dissolved in anhydrous methanol (40 ml), cooled to 0° C., and HCl gas was bubbled into the solution for 1 minute. The reaction mixture was allowed to warm to room temperature and stir overnight. A sample was taken from the reaction mixture and concentrated. NMR and Mass Spectrometry indicated minimal starting material and majority product. The solvent was stripped and the oily residue was re-dissolved in anhydrous methanol (40 ml), cooled to 0° C., and HCl gas was again bubbled into the solution for 1 minute. The reaction mixture was allowed to warm to room temperature and stir overnight. A sample was taken from the reaction mixture and concentrated. NMR and Mass Spectrometry indicated only the desired title product. The reaction mixture was concentrated to provide 1.01 g of a light yellow oil, 97% yield. The reaction mixture was stirred in acetonitrile (50 ml) for 3 hours and the title product as a white fine powder was recovered, 484 mg. Mass Spectrometry: (ZMD Waters Micromass, Electrospray), M+H at 234.2

$^1$HNMR: (400 mHz, $D_2O$) δ 1.51 (s, 3H), 2.09 (s, 3H), 2.72 (t, 2H), 2.97 (d, 1H), 3.19 (d, 1H), 3.36 (t, 2H), 3.73 (s, 3H). $^{13}$CNMR: δ 18.58, 21.69, 30.79, 37.79, 41.58, 54.24, 60.75, 165.41, 171.35.

Analysis calculated for $C_9H_{19}N_3O_2S+2$ HCl+0.3$H_2O$ (311.66): C, 34.68; H, 6.98; N, 13.48; Cl, 22.75; S, 10.29. Found: C, 34.51; H, 6.99; N, 13.75, Cl, 22.75, S, 10.43.

EXAMPLE 24

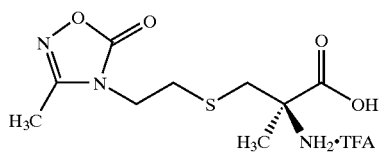

2-methyl-S-[2-(3-methyl-5-oxo-1,2,4-oxadiazol-4 (5H)-yl)ethyl]-L-cysteine, monotrifluoroacetate Example-24A N'-hydroxyethanimidamide

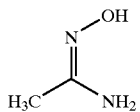

To a 3L round bottom flask was added hydroxylamine hydrochloride (138.98 g, 2.0 mol) in ethanol (1.2L) followed by a slow addition of sodium ethoxide (136.1 g, 2.0 mol). The temperature was maintained between 25° C. and 30° C. The reaction was then stirred for 30 minutes at room temperature. The precipitated NaCl was filtered off and washed with ethanol (100 mL). The hydroxylamine free base in the filtrate was added to a 3L flask and acetonitrile (112.75 g, 2.75 mol). This mixture was then subjected to reflux over night. After cooling, the solvent was carefully removed in vacuo to 50% of its original volume. The reaction then sat in an ice bath for one hour were upon crystals formed and were filtered off. The filtrate was carefully concentrated to 50% of its volume again. The reaction was placed into ice and the resulting crystals were again isolated by filtration to afford 52 g (35%) of the title product.

Example-24B

Potassium 3-methyl-1,2,4-oxadiazolin-5-onate

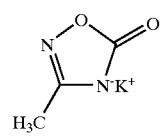

To a 25 mL round bottom flask was added the product of Example-24A (1 g, 0.013 mol), potassium t-butoxide (1.59 g, 0.013 mol) and diethyl carbonate (8.18 mL. 0.067 mol). The reaction was then refluxed for 5 hours. The solvent was removed and the resulting solid was triturated with methylene chloride and diethyl ether. The solid title product was then dried under high vacuum to afford 1.57 g (87%). $^1$H NMR ($d_6$-DMSO, 300 MHz) δ 1.69 (bs, 3H). $^3$C NMR ($d_6$-DMSO, 99 MHz) δ 13.26, 166.54, 173.99.

Example-24C 3-methyl-1-(1-bromoethyl)-2,4-oxadiazolin-5-one

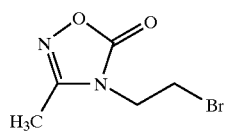

To a 250 mL Round Bottom Flask was added the title product of Example-24B, potassium 3-methyl-1,2,4-oxadiazolin-5-onate, (10.13 g, 0.0734 mol) in DMF (100 mL). To the slurry was added 1,2-dibromo ethane (31.54 mL, 0.366 mol). The reaction was heated in an oil bath for 2 hours at 130° C. The oil bath was removed and the reaction cooled after which water (200 mL) and ethyl acetate (50 mL) were added. The organics were collected and washed 3×100 mL brine. The organics were dried over $MgSO_4$ and then concentrated in vacuo to afford 9.1 g (60%) of the title compound. $^1$H NMR ($CDCl_3$, 300 MHz) δ 2.21 (s, 3H), 3.12 (t, 2H), 3.91 (t, 2H).

The 75 mL of methanol in a 100 mL round bottom flask was deoxygenated by bubbling nitrogen through it for 5 minutes. To 50 mL of this methanol was added NaOH (1.6 g, 0.040 mol). The suspension was stirred in an oil bath at 45° C. for 30 minutes after which the NaOH had dissolved. The resulting solution was cooled to room temperature and alpha-methyl cysteine (1.72 g, 0.010 mol) was added in 10 mL of deoxygenated methanol. The reaction stirred for 45 minutes at room temperature. To this reaction was added the product of Example-24C (2.07 g, 0.010 mol) in 10 mL of deoxygenated methanol. The reaction was complete as indicated by mass spectral analysis after it had been stirred over night. The reaction mixture was diluted with water (100 mL) and purified using reverse phase chromatography to afford 3.0 g (93%) of the title product of Example 24 as its trifluoroacetate salt. M.S. M+H$^+$(262.0), M+Na$^+$(282.0). $^1$H NMR ($CD_3OD$, 300 MHz) δ 1.39 (s, 3H), 2.23 (s, 3H), 2.74 (m, 2H), 2.84 (m, 2H), 3.72 (t, 2H).

EXAMPLE 25

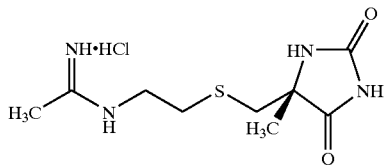

[2-[[[(4R)-4-methyl-2,5-dioxo-4-imidazolidinyl]methyl]thio]ethyl](1-N-iminoethyl)amine The [2-[[[(4R)-4-methyl-1-2,5-dioxo-4-imidazolidinyl]methyl]thio]ethyl]carbamic acid, 1,1-dimethylethyl ester isomer product of Example-22D (2.05 g, 6.5 mmol) was dissolved in 25 mL 4.0 N HCl in Dioxane and stirred for 10 min. After the addition of 2N HCl (5 mL) the reaction was stirred for additional 2 h. The reaction mixture was then concentrated under reduced pressure to give 1.68 g of a red brown gummy solid. This material was taken up in 25 mL of deionized water and the pH was adjusted to 8.4 with 2N NaOH. Ethylacetimidate hydrochloride (2.39 g, 0.019 mol) was then added while maintaining the pH at 8.4. The reaction mixture was then stirred at room temperature for one hour at pH 8.4. The pH of the reaction mixture was then adjusted to 3.5 by adding an appropriate amount of 1 N HCl and stirred for another 16 h. The reaction mixture was then concentrated on a rotary evaporator to obtain the crude product that was purified on a Gilson preparative HPLC to give the desired product as a white hygroscopic solid in 70% yield.

Mass $M^{+1}$=245. [α]in $H_2O$ at 25° C.=−37.6 (365 nm).

Analysis calculated for $C_9H_{16}N_4O_2S$+1.0 HCl+1.3$H_2O$ (formula weight=304.20): C, 35.54; H, 6.49; N, 18.42; Cl, 11.65; S, 10.54. Found: C, 35.83; H, 6.08; N, 18.55; Cl, 11.19, S 10.63.

EXAMPLE 26

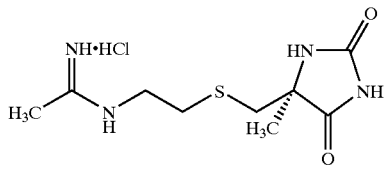

[2-[[[(4S)-4-methyl-2,5-dioxo-4-imidazolidinyl]methyl]thio]ethyl](1-N-iminoethyl)amine hydrochloride

Example-26A (5S)-5-[[(2-aminoethyl)thio]methyl]-5-methyl-2,4-imidazolidinedione, monohydrochloride

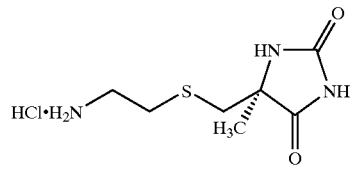

The [2-[[[(4S)-4-methyl-2,5-dioxo-4-imidazolidinyl]methyl]thio]ethyl]carbamic acid, 1,1-dimethylethyl ester isomer product of Example 22D was purified by chromatography using 66% Ethyl Acetate in Toluene, Biotage Flash 75 silica gel. A sample of this material (5.9 g, 16.5 mmol, [α]in MeOH at 25° C.=+45.7, 365 nm) was then dissolved in 165 mL THF and treated with 4.125 mL 4.0 N HCl in Dioxane. The reaction was allowed to stir for two hours at room temperature and monitored by TLC. The free amine product was then purified by chromatography using reverse phase media (YMC-ODS-AQ) to yield 4.8 g of the title material.

A 3.5 g (17.2 mmol) sample of the product of Example-26A was treated with 10% NaOH solution to pH 9–10. To this solution was added 4.26 g of ethyl acetimidate hydrochloride while adjusting pH to 9 by adding a solution of 10% NaOH. After stirring at pH 9 for 2 hours, the pH was adjusted to 7.5 by adding an appropriate amount of 0.1 N HCl. This solution was stirred for another 2 hours before the pH was further adjusted to 4.5 by adding 0.1 N HCl. After stirring this solution for 10 hours the water was removed under reduced pressure (11 mbar) and 47° C. water bath. The crude title product was chromatographed using reverse phase media (YMC-ODS-AQ) to give 156 mg of the title material. [α]in $H_2O$ at 25° C.=+54.8 (365 nm).

Analysis calculated for $C_9H_{16}N_4O_2S$+1.0 HCl+0.85$H_2O$ (formula weight=296.09): C, 36.51; H, 6.37; N, 18.92; Cl, 11.97; S, 10.83. Found: C, 36.69; H, 6.32; N, 18.85, Cl, 11.46, S 11.12.

EXAMPLE 27

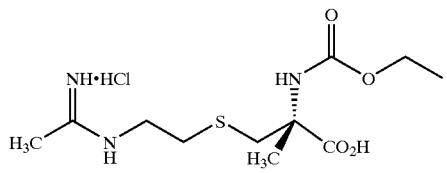

N-(ethoxycarbonyl)-S-[2-[(1-iminoethyl)amino]ethyl]-2-methyl-L-cysteine, monohydrochloride A sample of the product of Example 1 (3.22 g, 0.01 mol) was taken up in 50 mL of deionized water and to this $K_2CO_3$ (2.76 g) was added followed by the addition of ethychloroformate (1.08 g, 0.01 mol). The reaction mixture was stirred at 25° C. for 1 hour and then concentrated on rotary evaporator to give a white solid. This solid was purified by HPLC to give the desired product.

Mass $M^{+1}$=292

EXAMPLE 28

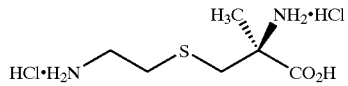

S-(2-aminoethyl)-2-methyl-D-cysteine dihydrochloride

A sample of the [2-[[[(4S)-4-methyl-2,5-dioxo-4-imidazolidinyl]methyl]thio]ethyl]carbamic acid, 1,1-dimethylethyl ester product of Example 22D (1.025 g, 3.25 mmol) was dissolved in 35 mL conc. HCl and stirred for 46 h at reflux temperature. The reaction mixture was then concentrated under reduced pressure to give 900 mg of a red brown gummy solid. This crude product was purified by reverse phase HPLC to give pure S-(2-aminoethyl)-2-methyl-D-cysteine dihydrochloride (800 mg, 98% yield). Mass $M^{+1}$=179. [α]in $H_2O$ at 25° C.=−85.6 (365 nm).

Analysis calculated for $C_6H_{14}N_2O_2S+2$ HCl+1$H_2O$+1.6 $NH_4Cl$ (formula weight 356.39; exact mass 178.07): C, 20.22; H, 7.35; N, 14.15, Cl, 35.81, S, 9.00. Found: C, 20.09, H, 6.95, N, 14.55, Cl, 36.15, S, 9.56.

EXAMPLE 29

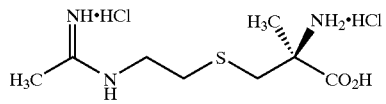

[2-(1-Iminoethylamino)ethyl]-2-methyl-D-cysteine hydrochloride

A sample of the product of Example 28 (1.25 g, 0.005 mol) was taken up in 20 mL of de-ionized water and the pH was adjusted to between 8.5 and 9 with 0.1N NaOH. Ethylacetimidate hydrochloride (2.39 g, 0.019 mol) was then added to the stirred reaction while maintaining the pH at 8.5. The reaction mixture was then stirred at 25° C. and 8.5 pH for 2 hours. The pH of the reaction mixture was then adjusted to 4.0 by adding an appropriate amount of 0.1 N HCl. The reaction mixture was then concentrated on a rotary evaporator and the crude product residue was purified on a Gilson HPLC system using YMC AQ column with 0.1% AcOH/$CH_3CN$/$H_2O$ to give the desired product in quantitative yield. Mass $M^{+1}$=220. [α]in $H_2O$ at 25° C.=−134.5 (365 nm).

Analysis calculated for $C_8H_{17}N_3O_2S+1.2$ HCl+2$H_2O$ (formula weight 299.09; exact mas 219.10): C, 32.13; H, 7.48; N, 14.05, Cl, 14.22, S, 10.72. Found: C, 32.39; H, 7.26; N, 14.05; Cl, 14.33; S, 10.42.

EXAMPLE 30

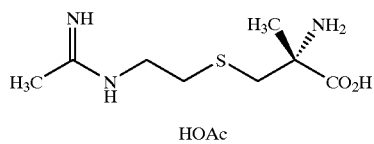

S-[2-[(1-Iminoethyl)amino]ethyl]-2-methyl-L-cysteine, acetate

Bio-Rad AG 1×8 resin, 200–400 mesh in the acetate form (300 g, 960 meqv.) was slurried in HPLC grade water and loaded onto a column 8 cm in diameter. The water was drained to the top of the column before 37 g (116 mmol) of the product of Example 1, dissolved in 10 mL of water, was loaded onto the column. The material was then eluted with 1 L of water. The first 200 mL fraction contained no product but the subsequent 500 mL yielded 30 g of the desired title product as a white glassy solid after removal of the water under reduced pressure.

Analysis calculated for $C_8H_{17}N_3O_2S+CH_3COOH+$ 1.3$H_2O$: C, 39.67; H, 7.86; N, 13.88. Found: C, 39.96; H, 7.87; N, 13.69.

EXAMPLE 31

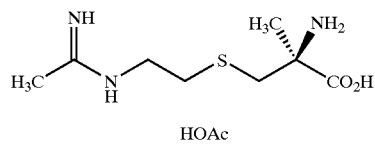

S-[2-[(1-Iminoethyl)amino]ethyl]-2-methyl-D-cysteine, acetate

A sample of the product of Example 29 as its mono hydrochloride salt (101 mg, 0.33 mmol) was converted to the title mono acetate by the method of Example 30.

Analysis calculated for $C_8H_{17}N_3O_2S.CH_3COOH+0.05$ HCl+2.2$H_2O$: C, 37.41, H, 8.01; N, 13.2, Cl, 0.56. Found: C, 37.30; H, 7.92; N, 13.17, Cl, 0.41.

EXAMPLE 32

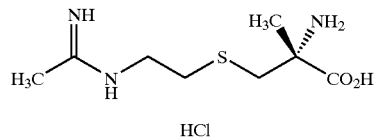

S-[2-[(1-Iminoethyl)amino]ethyl]-2-methyl-L-cysteine, monohydrochloride

This material was prepared by passing the product of Example 1 through a reverse phase column using the conditions described in Example 28.

Analysis calculated for $C_8H_{17}N_3O_2S+1.05$ HCl+0.8$H_2O$: C, 35.35; H, 7.36; N, 15.44; Cl, 13.65. Found: C, 35.33; H, 7.28; N, 15.45, Cl, 13.68.

EXAMPLE 33

D-galacturonic acid salt of S-[2-[(1-Iminoethyl) aminolethyl]-2-methyl-L-cysteine To a stirred 10 mL 0.001 M solution of acetate salt product of Example 30 was added D-galacturonic acid monohydrate (0.21 g, 0.001 mole). After stirring for 2 hours, the solution was concentrated under vacuum. The title galacturonic acid salt was dissolved in 10 mL of water and lyophilized.

EXAMPLE 34

Succinic acid salt of S-[2-[(1-Iminoethyl)amino] ethyl]-2-methyl-D-cysteine

The title material was prepared by the method of Example 33 from succinic acid and the product of Example 31.

Analysis calculated for $C_8H_{17}N_3O_2S+C_4H_6O_4+1.5H_2O$: C, 39.55; H, 7.19; N, 11.53. Found: C, 39.24; H, 6.04; N, 11.41.

EXAMPLE 35

Succinic acid salt of S-[2-[(1-Iminoethyl)amino] ethyl]-2-methyl-L-cysteine

The title material was prepared by the method of Example 33 from succinic acid and the product of Example 30.

Analysis calculated for $C_8H_{17}N_3O_2S+C_4H_6O_4+1.1H_2O$: C, 39.99; H, 7.40; N, 12.33. Found: C, 40.35; H, 7.11; N, 11.76.

EXAMPLE 36

Ethanolamine salt of S-[2-[(1-Iminoethyl)amino] ethyl]-2-methyl-L-cysteine

The title material was prepared by the method of Example 33 from ethanolamine and the product of Example 30.

Analysis calculated for $C_8H_{17}N_3O_2S+C_2H_7NO+2HCl+1.3H_2O$: C, 31.73, H, 7.67; N, 14.80; Cl, 18.73. Found: C, 31.41; H, 7.60; N, 15.00, Cl, 19.12.

EXAMPLE 37

Ethylene diamine salt of S-[2-[(1-Iminoethyl) amino]ethyl]-2-methyl-L-cysteine The title material was prepared by the method of Example 33 from ethylene diamine and the product of Example 30.

Analysis calculated for $C_8H_{17}N_3O_2S+2HCl+C_2H_8N_2+1.2H_2O$: C, 32.12; H, 7.92; N, 18.73, Cl, 18.96. Found: C, 31.90; H, 9.19; N, 18.08, Cl, 19.11.

EXAMPLE 38

DL-Aspartatic acid salt of S-[2-[(1-Iminoethyl) amino]ethyl]-2-methyl-L-cysteine The title material was prepared by the method of Example 33 from DL-aspartatic acid and the product of Example 30.

Analysis calculated for $C_{12}H_{24}N_4O_6S+1.8H_2O+0.4$ HOAc (formula weight=408.86): C, 37.60; H, 7.20; N, 13.70. Found: C, 37.59; H, 7.66; N, 13.73.

EXAMPLE 39

D-Glutamic acid salt of S-[2-[(1-Iminoethyl)amino] ethyl]-2-methyl-L-cysteine The title material was prepared by the method of Example 33 from D-glutamic acid and the product of Example 30.

Analysis calculated for $C_{13}H_{26}N_4O_6S+1.8H_2O+0.3$ HOAc (formula weight=416.88): C, 39.18; H, 7.45; N, 13.44. Found: C, 39.47; H, 7.52; N, 13.29.

EXAMPLE 40

Citric acid salt of S-[2-[(1-Iminoethyl)amino]ethyl]-2-methyl-L-cysteine

The title material was prepared by the method of Example 33 from citric acid and the product of Example 30.

Analysis calculated for $C_{14}H_{25}N_3O_9S+0.5H_2O+0.1$ HOAc+0.15 EtOH (formula weight=416.88): C, 433.36): C, 40.19; H, 6.35; N, 9.70. Found: C, 40.32; H, 5.74, N, 9.58.

EXAMPLE 41

DOWEX 50WX4-400 ion-exchange resin salt of S-[2-[(1-Iminoethyl)amino]ethyl]-2-methyl-L-cysteine DOWEX® 50WX4-400 (3 g, 1.6 meq/mL, 4.8 meq/g) was washed with deionized water (all water used in this experiment was deionized) to pH 6 of the wash. The resin was dried for one hour at room temperature. The product of Example 30 (0.6 g) in 30 mL of water was added to DOWEX resin (0.2 g). The suspension was shaken for three hours at ambient temperature using an ORBIT™ shaker, then stripped to dryness. This procedure was repeated three times with fresh 30 mL of water added after each concentration of the reaction mixture. With the final portion of fresh water, the slurry was shaken overnight at ambient temperature After stripping the reaction to dryness, 15 mL of water were added. The resin was filtered and washed three times with additional 15 mL of water. The filtrate was concentrated (several drops of acetic acid were added) and dried under vacuum giving 0.4 g of starting SC-84250 which was confirmed by $^1H$ NMR ($D_2O$). The loaded resin was dried at ambient temperature on the bench, followed by 1 hour under vacuum giving 0.3 g of loaded resin. A sample of this resin and a sample of unreacted washed DOWEX 50WX4-400 were submitted for nitrogen combustion analysis: The results for the untreated resin were % of N is 0%; for the loaded resin % of N is 9.72%.

EXAMPLE 42

Potassium hydrogen sulfate acid salt of S-[2-[(1-Iminoethyl)amino]ethyl]-2-methyl-L-cysteine The title material was prepared by the method of Example 33 from 0.001 mole of $KHSO_4$ and the product of Example 30.

Analysis calculated for $C_8H_{17}N_3O_2S+KHSO_4+2H_2O$: C, 24.75; H, 5.68; N, 10.90; S, 16.00. Found: C, 24.54; H, 5.66; N, 10.73, S, 16.38.

EXAMPLE 43

Potassium hydrogen sulfate acid salt of S-[2-[(1-Iminoethyl)amino]ethyl]-2-methyl-L-cysteine The title material was prepared by the method of Example 33 from 0.001 mole of $KHSO_4$ and the product of Example 30.

EXAMPLE 44

Hydrogen sulfate acid salt of S-[2-[(1-Iminoethyl) amino]ethyl]-2-methyl-L-cysteine To a stirred 10 mL solution of the product of Example 30 was added 2 mL 0.505 N $H_2SO_4$. After stirring for 2 hours, the solution was concentrated under vacuum. The resulting salt was dissolved in 10 mL of water and lyophilized.

Analysis calculated for $C_8H_{17}N_3O_2S+0.5H_2SO_4+1.5H_2O$: C, 32.58; H, 7.23; N, 14.75; S, 16.42. Found: C, 32.53; H, 7.17; N, 14.23, S, 16.28.

EXAMPLE 45

Glycerate salt of S-[2-[(1-Iminoethyl)amino]ethyl]-2-methyl-L-cysteine

S-Glyceric acid was prepared from its calcium salt by stirring for 4 hours with Dowex® 50W resin in its acid form. The resin was filtered and washed with $H_2O$. The resulting filtrate was concentrated and dried under vacuum.

Analysis calculated for $C_3H_6O_4$: C, 31.31, H, 6.13. Found: C, 31.29, H, 6.19.

The method described in Example 33 was used to prepare the S-glyceric acid salt from the product of Example 30 starting with 0.001 mole of S-glyceric acid.

Analysis calculated for $C_{11}H_{23}N_3O_6S+1.5H_2O$: C, 37.49; H, 7.44; N, 11.92; S, 9.10. Found: C, 37.49; H, 7.31; N, 11.73; S, 9.22.

EXAMPLE 46

Malate salt of S-[2-[(1-Iminoethyl)amino]ethyl]-2-methyl-L-cysteine

The method described in Example 33 was used to prepare the malic acid salt from the product of Example 30 starting with 0.001 mole of malic acid.

Analysis calculated for $C_8H_{17}N_3O_2S+1.33H_2O+C_4H_6O_5$: C, 38.20; H, 6.85; N, 11.15. Found: C, 38.37; H, 6.51; N, 11.09.

EXAMPLE 47

Hemi-malate salt of S-[2-[(1-Iminoethyl)amino]ethyl]-2-methyl-L-cysteine

The method described in Example 33 was used to prepare the malic acid salt from the product of Example 30 starting with 0.0005 mole of malic acid.

Analysis calculated for $C_8H_{17}N_3O_2S+1.75H_2O+0.5 C_4H_6O_5$: C, 37.92; N, 13.22. Found: C, 37.92; H, 7.88; N, 13.03.

EXAMPLE 48

Potassium dihydrogen phosphate salt of S-[2-[(1-Iminoethyl)amino]ethyl]-2-methyl-L-cysteine The method described in Example 33 was used to prepare the title salt from the product of Example 30.

Analysis calculated for $C_8H_{17}N_3O_2S+KH_2PO_4+2.5H_2O+0.66$ HOAc: C, 25.44; H, 6.10; N, 9.55. Found: C, 25.27; H, 5.95; N, 9.80.

EXAMPLE 49

Sodium dihydrogen phosphate salt of S-[2-[(1-Iminoethyl)amino]ethyl]-2-methyl-L-cysteine The method described in Example 33 was used to prepare the title salt from the product of Example 30.

Analysis calculated for $C_8H_{17}N_3O_2S+NaH_2PO_4+2H_2O+0.3$ HOAc: C, 26.26; H, 6.20; N, 10.68. Found: C, 26.57; H, 6.25; N, 10.72.

EXAMPLE 50

Calcium dihydrogen phosphate salt of S-[2-[(1-Iminoethyl)amino]ethyl]-2-methyl-L-cysteine The method described in Example 33 was used to prepare the title salt from the product of Example 30.

Analysis calculated for $C_8H_{17}N_3O_2S+2 NaH_2PO_4+2H_2O$: C, 19.40; H, 5.09; N, 8.48. Found: C, 19.34; H, 5.10; N, 8.56.

EXAMPLE 51

Calcium phosphate salt of S-[2-[(1-Iminoethyl)amino]ethyl]-2-methyl-L-cysteine

The method described in Example 33 was used to prepare the title salt from the product of Example 30.

Analysis calculated for $C_8H_{17}N_3O_2S+Ca(H_2PO_4)_2+0.2$ HOAc: C, 19.96, H, 4.35; N,8.31. Found: C, 20.14; H, 5.73; N, 8.80.

EXAMPLE 52

Calcium hydrogen phosphate salt of S-[2-[(1-Iminoethyl)amino]ethyl]-2-methyl-L-cysteine The method described in Example 33 was used to prepare the title salt from the product of Example 30.

Analysis calculated for $C_8H_{17}N_3O_2S+CaHPO_4+2.2$ HCl+$H_2O$: C, 21.18; H, 4.93; N, 9.26. Found: C, 21.20; H, 5.28; N, 9.37.

EXAMPLE 53

Calcium phosphate, tribasic salt of S-[2-[(1-Iminoethyl)amino]ethyl]-2-methyl-L-cysteine (1.62:1)

The method described in Example 33 was used to prepare the title salt from the product of Example 30.

Analysis calculated for $C_8H_{17}N_3O_2S+Ca_3 (PO_4)_2+$HOAc+$3H_2O$: C, 14.37; H, 2.77; N, 5.03. Found: C, 14.13; H, 3.01; N, 4.71.

EXAMPLE 54

Calcium phosphate, tribasic salt of S-[2-[(1-Iminoethyl)amino]ethyl]-2-methyl-L-cysteine (1:1)

The method described in Example 33 was used to prepare the title salt from the product of Example 30.

Analysis calculated for $C_8H_{17}N_3O_2S.Ca_3 (PO_4)_2+2.2$ HCl+$2H_2O$: C, 14.88; H, 3.62; N, 6.51. Found: C, 15.09; H, 3.85; N, 6.23.

EXAMPLE 55

Bio-Rex® 70 salt of S-[2-[(1-Iminoethyl)amino]ethyl]-2-methyl-L-cysteine

The method described in Example 41 was used to prepare the Bio-Rex® 70 salt of the neutral form of the product of Example 1. The results for the untreated resin were % of N is 0%; for the loaded resin % of N is 7.93%.

EXAMPLE 56

IPR (amberlite)-69 salt of S-[2-[(1-Iminoethyl)amino]ethyl]-2-methyl-L-cysteine

The IPR-69 salt of the neutral form of the product of Example 1 was prepared in the same manner as described in Example 41 except the resin was treated first with 1 N HCl to convert it to H+form. This resin is a polystyrenedivinylbenzene sulfonic acid resin as is the Dowex-50. However, it is GMP quality but covers a broader mesh size. It is less colored than the Dowex. After the washings and prior to loading the compound, the resin was slurried in $H_2O$ and the fine particles that rose to the top were decanted. From this reaction was recovered 4.9 g of salt. 7.69% N (or 0.401 g of SC-84250/g of resin).

EXAMPLE 57

IPR (amberlite)-69 salt of S-[2-[(1-Iminoethyl)amino]ethyl]-2-methyl-L-cysteine

The IPR-64 salt the neutral form of the product of Example 1 was prepared in the same manner as described in Example 41 with the decanting of fines as described in Example 56. This resin is the same as the Bio-Rex 70 with the exception that is GMP quality. The only variation was after shaking overnight the resin was shaken an additional two times with strips in between. From this reaction was recovered 4.3 g. 6.20% N (0.346 g of compound/g of resin

EXAMPLE 58

Preparation of monohydrochloride from the dihydrochloride salt of S-[2-[(1-Iminoethyl)amino]ethyl]-2-methyl-L-cysteine

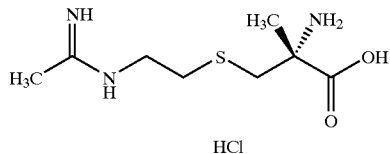

HCl

Dissolve ~120 mg of the product of Example 1 in 3 ml of DMF. Add 1 ml of propylene oxide and stir. The product will precipitate. Wash with ether. Dissolve product in water and freeze dry. Table 1 shows the elemental analysis.

EXAMPLE 59

Preparation of monosubstituted salts of S-12-[(1-Iminoethyl)amino]ethyl]-2-methyl-L-cysteine salts by AgCl precipitation

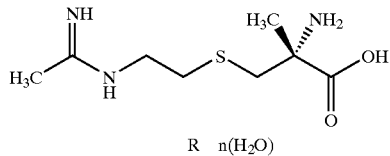

R   n(H₂O)

Dissolve the product of Example 58 in water. Add a stoichiometric amount of a silver salt. Filter the solids. Freeze dry the remaining solution. Table 2 shows the elemental analyses where n represents the moles of water.

EXAMPLE 60

Preparation of phosphate salts of S-[2-[(1-Iminoethyl)amino]ethyl]-2-methyl-L-cysteine salts by AgCl precipitation

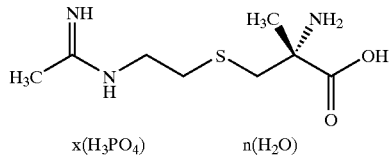

x(H₃PO₄)   n(H₂O)

Dissolve the product of Example 1 in water. Add two moles of Ag₃PO₄ per mole of product of Example 1 and mix. Filter out the solids and freeze dry the resulting solution. Analyze the resulting material, and adjust the phosphate content with H₃PO₄. Table 3 shows the elemental analyses where x represents the moles of phosphoric acid.

EXAMPLE 61

Preparation of mixed salts from S-[2-[(1-Iminoethyl)amino]ethyl]-2-methyl-L-cysteine monohydrochloride

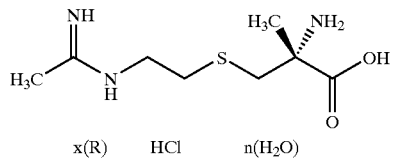

x(R)   HCl   n(H₂O)

Dissolve the product of Example 58 in water. Add a stoichiometric amount of reagent (R). Table 4 shows the elemental analyses where x represents the moles of R.

EXAMPLE 62

Preparation of mixed salts from S-[2-[(1-Iminoethyl)amino]ethyl]-2-methyl-L-cysteine dihydrochloride

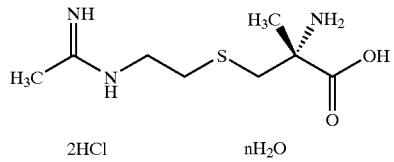

2HCl   nH₂O

Dissolve the product of Example 1 in water. Add base until the pH is 6. Table 5 shows the elemental analyses.

EXAMPLE 63

Preparation of zinc salts from S-[2-[(1-Iminoethyl)amino]ethyl]-2-methyl-L-cysteine dihydrochloride

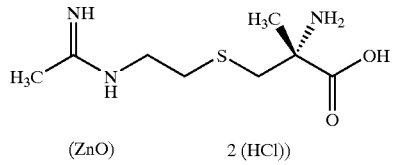

(ZnO)   2 (HCl))

Dissolve the product of Example 1 in water. Mix with excess zinc oxide. Filter and freeze dry the resulting solution. Table 6 shows the elemental analysis.

EXAMPLE 64

Preparation of mixed salts from S-[2-[(1-Iminoethyl)amino]ethyl]-2-methyl-L-cysteine neutral compound

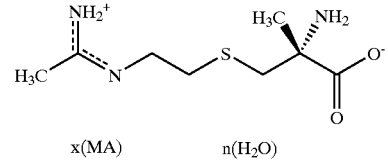

x(MA)   n(H₂O)

Dissolve the neutral form of the product of Example 20 in water. Mix with desired reagent and freeze dry. Table 7 shows the elemental analyses where x represents the moles of MA, metal cation and counter anion.

EXAMPLE 65

Preparation of salts from S-[2-[(1-Iminoethyl)amino]ethyl]-2-methyl-L-cysteine neutral compound The following Table 8 lists salts and their elemental analyses prepared from the product of Example 1 by one of the variety of methods described in this application. Table 8 illustrates the elemental analysis of these salts where D represents S-[2-[(1-Iminoethyl)amino]ethyl]-2-methyl-L-cysteine with the formula of $C_8H_{17}N_3O_2S$ and A the empirical formula of the indicated acid and or counter ion source.

TABLE 1

| Formula | Calculated | | | | Found | | | |
| --- | --- | --- | --- | --- | --- | --- | --- | --- |
| | C | H | N | Cl | C | H | N | Cl |
| $C_8H_{17}N_3O_2S(HCl)(H_2O)$ | 35.10 | 7.36 | 15.35 | 12.95 | 35.06 | 7.53 | 14.90 | 13.07 |

TABLE 2

| Acid(R) | Formula | Calculated | | | | Found | | | |
| --- | --- | --- | --- | --- | --- | --- | --- | --- | --- |
| | | C | H | N | S | C | H | N | S |
| Methane Sulfonic | $C_8H_{17}N_3O_2S$ $(CH_4SO_3)$ $(H_2O)$ | 32.42 | 6.95 | 12.60 | 19.23 | 32.09 | 7.06 | 12.36 | 19.67 |
| Toluene Sulfonic | $C_8H_{17}N_3O_2S$ $C_7H_8O_3S$ $(H_2O)$ | 43.99 | 6.65 | 10.26 | 15.66 | 43.83 | 6.75 | 9.91 | 14.5 |
| Lactic | $C_8H_{17}N_3O_2S$ $C_3H_6O_3$ $(H_2O)$ | 40.36 | 7.70 | 12.83 | 9.79 | 40.79 | 7.84 | 12.6 | 9.68 |
| $HNO_3$ Nitric | $C_8H_{17}N_3O_2S$ $HNO_3$ $(H_2O)$ | 31.99 | 6.71 | 18.66 | 10.67 | 32.32 | 5.79 | 18.32 | — |
| Acetic | $C_8H_{17}N_3O_2S$ $C_2H_4O_2$ $1.5(H_2O)$ | 39.20 | 7.90 | 13.72 | 10.46 | 39.19 | 7.15 | 13.53 | — |
| Benzoic | $C_8H_{17}N_3O_2S$ $C_7H_6O_2$ $1.5(H_2O)$ | 48.90 | 7.11 | 11.40 | 8.70 | 48.93 | 7.45 | 11.74 | — |

TABLE 2-continued

| Acid(R) | Formula | Calculated | | | | Found | | | |
|---|---|---|---|---|---|---|---|---|---|
| | | C | H | N | S | C | H | N | S |
| 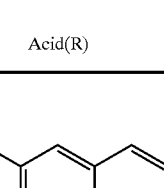 Pamoic | $C_8H_{17}N_3O_2S$ .5($C_{23}H_{16}O_6$) 1.5($H_2O$) | 53.17 | 6.41 | 9.54 | 7.28 | 53.65 | 6.38 | 9.92 | 6.92 |

TABLE 3

| Formula | Calculated | | | | Found | | | |
|---|---|---|---|---|---|---|---|---|
| | C | H | N | P | C | H | N | P |
| $C_8H_{17}N_3O_2S(H_3PO_4)1.5(H_2O)$ | 27.91 | 6.73 | 12.20 | 9.00 | 27.74 | 6.03 | 12.12 | 8.73 |
| $C_8H_{17}N_3O_2S2(H_3PO_4)2(H_2O)$ | 21.29 | 6.03 | 9.31 | 13.73 | 20.89 | 5.64 | 9.3 | 13.67 |

TABLE 4

| Formula (R) | | Calculated | | | | Found | | | |
|---|---|---|---|---|---|---|---|---|---|
| | | C | H | N | Cl | C | H | N | Cl |
| $CaCl_2$ | $C_8H_{17}N_3O_2S$ .5($CaCl_2$) 1.5($H_2O$) (HCl) | 28.41 | 6.26 | 12.42 | 20.96 | 28.42 | 6.3 | 12.26 | 19.6 |
| Lactic Acid | $C_8H_{17}N_3O_2S$ $C_3H_6O_3$ HCl | 38.2 | 6.99 | 12.15 | 10.25 | 38.32 | 7.16 | 12.23 | 10.81 |
| Succinic Acid | $C_8H_{17}N_3O_2S$ .5($C_4H_6O_4$) HCl .5($H_2O$) | 37.09 | 6.85 | 12.98 | 10.95 | 37.22 | 6.68 | 13.08 | 11.45 |

TABLE 5

| Formula | Calculated | | | | | Found | | | | |
|---|---|---|---|---|---|---|---|---|---|---|
| | C | H | N | M | Cl | C | H | N | M | Cl |
| $C_8H_{16}N_3O_2SLi2(HCl)2(H_2O)$ | 28.75 | 6.64 | 12.57 | 2.08 | 21.22 | 28.05 | 6.58 | 12.34 | 2.14 | 21.59 |
| $C_8H_{16}N_3O_2SNa2(HCl)1.5(H_2O)$ | 28.16 | 6.20 | 12.31 | — | 20.78 | 27.71 | 6.10 | 12.47 | — | 22.20 |
| $C_8H_{16}N_3O_2SK2(HCl)2(H_2O)$ | 26.23 | 6.05 | 11.47 | — | 19.36 | 25.75 | 5.60 | 11.50 | — | 21.13 |

TABLE 6

| Formula/ | Calculated | | | | | Found | | | | |
|---|---|---|---|---|---|---|---|---|---|---|
| References | C | H | N | Cl | Zn | C | H | N | Cl | Zn |
| $C_8H_{17}N_3O_2S2(HCl)ZnO$ | 25.72 | 5.13 | 11.25 | 18.98 | 17.50 | 25.98 | 4.52 | 11.57 | 20.54 | 17.13 |

TABLE 7

| | Measured | | | Found | | |
|---|---|---|---|---|---|---|
| Formula | C | H | N | C | H | N |
| $C_8H_{17}N_3O_2S(NaCl)2(H_2O)$ | 30.62 | 6.75 | 13.39 | 30.93 | 6.39 | 13.27 |
| $C_8H_{17}N_3O_2S0.5(CaCl_2)1.5(H_2O)$ | 31.84 | 6.68 | 13.92 | 31.59 | 6.57 | 13.73 |
| $C_8H_{17}N_3O_2S(NaCH_3SO_3)2(H_2O)$ | 28.95 | 6.48 | 11.25 | 28.91 | 6.06 | 10.99 |

TABLE 8

| | Calculated | | | | Found | | | |
|---|---|---|---|---|---|---|---|---|
| Acid/Formula | C | H | N | | C | H | N | |
| L-Tartaric Acid | | | | | | | | |
| D *0.6 A *0.75 $H_2O$ | 38.59 | 6.91 | 12.98 | | 38.67 | 6.94 | 12.65 | |
| D *1.0 A *0.5 $H_2O$ | 38.09 | 6.39 | 11.10 | | 38.04 | 6.43 | 11.38 | |
| D *1.2 A *2.0 $H_2O$ | 32.48 | 5.75 | 8.88 | | 32.76 | 5.50 | 8.96 | |
| D *1.1 A *1.5 $H_2O$ | 34.37 | 5.93 | 9.70 | | 34.51 | 5.81 | 9.69 | |
| D-Tartaric Acid | | | | | | | | |
| D *0.5 A *0.5 $H_2O$ | 39.59 | 6.98 | 13.85 | | 39.27 | 7.09 | 13.34 | |
| D *1.0 A *1.0 $H_2O$ | 37.20 | 6.50 | 10.85 | | 37.85 | 6.45 | 10.43 | |
| (R)-(−)-Mandelic Acid | | | | | | | | |
| D *1.0 A *2.5 $H_2O$ | 49.99 | 7.87 | 10.93 | | 49.90 | 6.92 | 10.83 | |
| (S)-(+)-Mandelic Acid | | | | | | | | |
| D *1.0 A *2.75 $H_2O$ | 49.41 | 7.90 | 10.86 | | 49.38 | 8.23 | 10.78 | |
| Citric Acid | | | | | | | | |
| D *0.4 A *0.8 $H_2O$ | 40.22 | 7.08 | 14.23 | | 40.96 | 6.87 | 13.26 | |
| D *1.0 A *0.5 $H_2O$ *0.1 HOAc *.015 EtOH | 40.19 | 6.35 | 9.70 | | 40.32 | 5.74 | 9.58 | |
| | | | | S | | | | S |
| Mucic Acid | | | | | | | | |
| D *0.5 A *2.0 $H_2O$ | 36.66 | 7.27 | 11.66 | | 36.46 | 7.12 | 11.24 | |
| D *0.6 A *1.0 $H_2O$ | 40.73 | 6.84 | 12.95 | 9.89 | 38.09 | 7.13 | 12.03 | 9.30 |
| Maleic Acid | | | | | | | | |
| D *0.5 A *1.5 $H_2O$ | 39.46 | 7.29 | 13.81 | | 39.64 | 6.98 | 13.01 | |
| Malonic Acid | | | | | | | | |
| D *0.5 A *1.5 $H_2O$ | 38.24 | 7.34 | 14.08 | | 38.03 | 7.37 | 13.89 | |
| Benzoic Acid | | | | | | | | |
| D *1.1 A *2.75 $H_2O$ | 50.81 | 7.90 | 11.32 | | 50.54 | 6.39 | 11.12 | |
| D *1.0 A *1.5 $H_2O$ | 48.90 | 7.11 | 11.40 | | 48.93 | 7.45 | 11.74 | |
| D *2.4 A *1.4 $H_2O$ | 55.41 | 6.41 | 7.82 | | 55.75 | 6.51 | 7.52 | |
| | | | | Cl M | | | | Cl M |
| Hydrochloric Acid | | | | | | | | |
| D *1.15 A *2.75 $H_2O$ *0.33 n-PrOH | 36.17 | 8.49 | 14.22 | 13.79 | 36.24 | 8.10 | 13.98 | 13.51 |
| D *1.0 A *1.0 $H_2O$ | 35.10 | 7.36 | 15.35 | 12.95 | 35.06 | 7.53 | 14.90 | 13.07 |
| D *1.05 A *0.8 $H_2O$ | 35.35 | 7.36 | 15.44 | 13.65 | 35.33 | 7.28 | 15.45 | 13.68 |
| D *1.0 A *1.5 $H_2O$ *0.5 CaCl2 | 28.41 | 6.26 | 12.42 | 20.96 | 28.42 | 6.30 | 12.26 | 19.60 |

TABLE 8-continued

| Acid/Formula | Calculated | | | | | Found | | | | |
|---|---|---|---|---|---|---|---|---|---|---|
| | C | H | N | | | C | H | N | | |
| | | | | | Li | | | | | Li |
| D *2.0 A *2.0 H₂O *1.0 Li+ | 28.75 | 6.64 | 12.57 | 21.22 | 2.08 | 28.05 | 6.58 | 12.34 | 21.59 | 2.14 |
| D *2.0 A *1.5 H₂O *1.0 Na+ | 28.16 | 6.20 | 12.31 | 20.78 | | 27.71 | 6.10 | 12.47 | 22.20 | |
| D *2.0 A *2.0 H₂O *1.0 K+ | 26.23 | 6.05 | 11.47 | 19.36 | | 25.75 | 5.60 | 11.50 | 21.13 | |
| | | | | | Zn | | | | | Zn |
| D *2.0 A *0.5 ZnO | 25.72 | 5.13 | 11.25 | 18.98 | 17.50 | 25.98 | 4.52 | 11.57 | 20.54 | 17.13 |
| D *1.20 A *1.25 H₂O *1.0 Me4N+ Cl- | 36.47 | 8.34 | 14.18 | 19.74 | 8.11 | 36.44 | 8.66 | 14.18 | 19.84 | 6.92 |
| | | | | Cl | S | | | | Cl | S |
| Methanesulfonic Acid | | | | | | | | | | |
| D *1.0 A *1.25 HCl *0.8 H₂O | 28.80 | 6.40 | 11.19 | 11.80 | 17.08 | 28.29 | 6.38 | 11.16 | 12.01 | 17.17 |
| D *2.0 A *0.75 HCl *5.0 H₂O | 23.10 | 6.74 | 8.08 | 5.11 | 18.50 | 23.03 | 6.58 | 8.16 | 5.18 | 18.58 |
| D *1.0 A *1.0 H₂O | 32.42 | 6.95 | 12.60 | | 19.23 | 32.09 | 7.06 | 12.36 | | 19.67 |
| D *1.0A- *2.0 H₂O *1.0 Na+ | 28.95 | 6.48 | 11.25 | | | 28.91 | 6.06 | 10.99 | | |
| D *1.0 A *1.0 Me₄N+ *1.75 H₂O | 37.17 | 8.52 | 13.34 | | 15.72 | 37.45 | 7.92 | 12.81 | | 14.95 |
| Tosic Acid | | | | | | | | | | |
| D *1.0 A *1.5 H₂O | 45.07 | 6.82 | 9.35 | | | 45.60 | 6.55 | 9.21 | | |
| D *2.2 A *2.4 H₂O | 46.36 | 6.55 | 6.93 | | | 46.76 | 6.01 | 6.65 | | |
| D *1.0 A *1.5 HCl *1.0 H₂O | 38.81 | 6.19 | 9.05 | 11.46 | 13.18 | 38.90 | 6.37 | 8.93 | 11.57 | 13.80 |
| D *1.0 *1.0 H₂O | 43.99 | 6.65 | 10.26 | | 15.66 | 43.83 | 6.75 | 9.91 | | 14.50 |
| D *1.0 A- *1.0 Me₄N+ *1.0 H₂O | 47.28 | 7.94 | 11.61 | | 13.29 | 47.39 | 7.90 | 10.40 | | 12.91 |
| D *1.0 A *10A- *1.0 Me4N+ *1.0 H₂O | 47.83 | 6.79 | 8.58 | | 14.73 | 47.95 | 7.25 | 8.49 | | 14.77 |
| D *1.2 A *1.0 H₂O | 42.74 | 6.18 | 9.84 | | | 42.94 | 5.83 | 9.34 | | |
| D *2.1 A *5.0 H₂O | 38.57 | 6.22 | 6.55 | | | 38.87 | 5.75 | 6.50 | | |
| | | | | Br | | | | | Br | |
| Hydrobromic Acid | | | | | | | | | | |
| D *1.1 A *2.25 H₂O 0.3 HOAc | 30.85 | 7.17 | 12.55 | 26.25 | | 30.66 | 6.95 | 12.20 | 26.77 | |
| D *0.61 A *1.0 H₂O | 32.01 | 6.04 | 14.00 | 26.62 | 10.68 | 31.51 | 6.33 | 13.82 | 25.71 | 10.16 |
| Ethanesulfonic Acid | | | | | | | | | | |
| D *1.2 A | 35.45 | 6.94 | 11.96 | | | 35.58 | 6.98 | 11.53 | | |
| D *2.1 A *1.0 H₂O | 31.27 | 6.80 | 8.97 | | | 31.85 | 6.62 | 8.45 | | |
| D-(+)-Malic Acid | | | | | | | | | | |
| D *0.55 A *0.4 H₂O | 40.80 | 7.08 | 13.99 | | | 40.66 | 6.95 | 13.40 | | |
| 1-Adamantaneacetic Acid | | | | | | | | | | |
| D *0.91 A *3.5 H₂O | 53.11 | 9.53 | 9.88 | | | 53.44 | 8.85 | 10.00 | | |
| 1-Adamantane-carboxylic Acid | | | | | | | | | | |
| D *0.95 A *3.25 H₂O | 52.57 | 9.37 | 9.97 | | | 52.61 | 7.73 | 9.92 | | |
| Flavianic Acid | | | | | | | | | | |
| D *1.0 A *1.0 H₂O | 39.20 | 4.57 | 12.70 | | 11.63 | 38.80 | 3.94 | 12.35 | | 11.84 |
| 1R-(-)-Camphorsulfonic Acid | | | | | | | | | | |
| D *1.0 A *0.75 H₂O | 46.04 | 7.51 | 8.95 | | 13.66 | 46.12 | 7.44 | 8.72 | | 13.66 |
| 1S-(+)-Camphorsulfonic Acid | | | | | | | | | | |
| D *1.0 A *2.0 H₂O | 46.48 | 7.48 | 9.03 | | 13.79 | 46.41 | 7.85 | 8.74 | | 14.13 |
| 2-Mesitylenesulfonic Acid | | | | | | | | | | |
| D *1.0 A *1.25 H₂O | 46.19 | 7.18 | 9.50 | | 14.51 | 45.96 | 8.54 | 7.33 | | 14.91 |

TABLE 8-continued

| Acid/Formula | Calculated | | | | Found | | | |
|---|---|---|---|---|---|---|---|---|
| | C | H | N | | C | H | N | |
| 1,5-Naphthalenedisulfonic Acid | | | | | | | | |
| D *1.0 A *2.0 H$_2$O | 39.86 | 5.25 | 7.35 | 17.92 | 39.65 | 4.25 | 7.33 | 18.77 |
| D *0.6 A *1.250 H$_2$O | 40.54 | 5.90 | 10.13 | 17.01 | 40.03 | 4.60 | 10.14 | 17.44 |
| 1,2-Ethanedisulfonic Acid | | | | | | | | |
| D *0.5 A *0.5 H$_2$O | 33.42 | 6.54 | 12.99 | 19.83 | 33.01 | 6.29 | 12.75 | 18.96 |
| D *0.5 A *1.5 HCl *1.0 H$_2$O | 27.92 | 6.12 | 10.85 13.75 | 16.57 | 27.84 | 5.96 | 11.05 13.76 | 16.03 |
| D *1.0 A *0.8 HCl *1.5 H$_2$O | 25.79 | 5.80 | 9.02 6.09 | 20.66 | 26.07 | 5.76 | 9.58 6.08 | 19.97 |
| Sulfonacetic Acid | | | | | | | | |
| D *1.1 A *1.1 H$_2$O | 33.42 | 5.89 | 11.69 | 17.84 | 31.61 | 6.04 | 10.92 | 17.35 |
| 1,3-Propanedisulfonic Acid | | | | | | | | |
| D *0.67 A *1.0 HCl *1.25 H$_2$O | 28.96 | 6.28 | 10.12 8.54 | 18.08 | 28.72 | 6.32 | 10.10 8.96 | 18.12 |
| D *0.3 A *1.6 HCl *1.25 H$_2$O | 29.34 | 6.56 | 11.40 15.39 | 14.53 | 29.17 | 6.71 | 11.50 15.48 | 14.51 |
| L-(+)-Lactic Acid | | | | | | | | |
| D *1.0 A *1.0 H$_2$O | 40.36 | 7.70 | 12.83 | 9.79 | 40.79 | 7.84 | 12.60 | 9.68 |
| D *1.0 A *1.0 H$_2$O *1.0 HCl | 38.20 | 6.99 | 12.15 10.25 | | 38.32 | 7.16 | 12.23 10.81 | |
| Nitric Acid | | | | | | | | |
| D *1.0 A *1.0 H$_2$O | 31.99 | 6.71 | 18.66 | | 32.32 | 5.79 | 18.32 | |
| Acetic Acid | | | | | | | | |
| D *1.0 A *1.0 H$_2$O | 39.20 | 7.90 | 13.72 | | 39.19 | 7.15 | 13.53 | |
| D *1.0 A *1.3 H$_2$O | 39.67 | 7.86 | 13.88 | | 39.96 | 7.87 | 13.69 | |
| D *1.0 A *0.05 HCl *2.2 H$_2$O (S-Enantiomer) | 37.41 | 8.01 | 13.20 | 0.56 | 37.30 | 7.92 | 13.17 | 0.41 |
| Pamoic Acid | | | | | | | | |
| D *0.5 A *1.5 H$_2$O | 53.17 | 6.41 | 9.54 | 7.28 P | 53.65 | 6.38 | 9.92 | 6.92 P |
| Phosphoric Acid | | | | | | | | |
| D *1.0 A *1.5 H$_2$O | 27.21 | 6.73 | 12.20 | 9.00 | 27.74 | 6.03 | 12.12 | 8.73 |
| D *2.0 A *2.0 H$_2$O | 21.29 | 6.03 | 9.31 | 13.73 | 20.89 | 5.64 | 9.30 | 13.67 |
| D *1.0 A- *2.5 H$_2$O *0.66 HOAc *1.0 K+ | 25.44 | 6.10 | 9.55 | | 25.27 | 5.95 | 9.80 | |
| D *1.0 A- *2.0 H$_2$O *0.33 HOAc *1.0 Na+ | 26.26 | 6.20 | 10.68 | | 26.57 | 6.25 | 10.72 | |
| D *2.0 A- *0.2 H OAc *1.0 Ca++ | 19.96 | 4.35 | 8.31 | | 20.14 | 5.73 | 8.80 | |
| D *1.0 A- *2.2 HCl *1.0 H$_2$O *0.66 HOAc *1.0 Ca++ | 21.18 | 4.93 | 9.26 | | 21.20 | 5.28 | 9.37 | |
| D *2.0 A--- *3.0 H$_2$O *1.0 HOAc *2.0 Ca++ | 14.37 | 2.77 | 5.03 | | 14.13 | 3.01 | 4.71 | |
| D *2.0 A--- *2.2 HCl *2.0 H$_2$O *0.66 HOAc *3.0 Ca++ | 14.88 | 3.62 | 6.51 | | 15.09 | 3.85 | 6.23 | |
| Succinic Acid | | | | | | | | |
| D *0.5 A *0.5 H$_2$O *1.0 HCl | 37.09 | 6.85 | 12.98 | 10.95 | 37.22 | 6.68 | 13.08 | 11.45 |
| D *0.5 A *0.5 H$_2$O *1.0 HCl | 39.99 | 7.40 | 12.33 | | 40.35 | 7.11 | 11.76 | |
| D *1.0 A *1.5 H$_2$O (S-Enantiomer) | 39.55 | 7.19 | 11.53 | | 39.24 | 6.04 | 11.41 | |
| Sodium Chloride | | | | | | | | |
| D *1.0 A *2.0 H$_2$O | 30.62 | 6.75 | 13.39 | | 30.93 | 6.39 | 13.27 | |
| Calcium Chloride | | | | | | | | |
| D *0.5 A *1.5 H$_2$O | 31.84 | 6.68 | 13.92 | | 31.59 | 6.57 | 13.73 | |
| D *0.5 A *2.5 H$_2$O | 29.09 | 5.19 | 12.72 | | 28.40 | 6.35 | 10.70 | |
| D-a-Glacturonic Acid | | | | | | | | |
| D *1.0 A *1.75 H$_2$O | 37.84 | 7.00 | 9.57 | 7.61 | 37.86 | 7.10 | 9.60 | 7.61 |

TABLE 8-continued

| Acid/Formula | Calculated | | | Found | | | |
|---|---|---|---|---|---|---|---|
| | C | H | N | | C | H | N | |
| Sulfuric Acid | | | | | | | | |
| D *1.0 A- *2.0 H₂O *1.0 K+ | 24.75 | 5.68 | 10.90 | 16.00 | 24.54 | 5.66 | 10.73 | 16.38 |
| D *0.5 A *1.5 H₂O | 32.58 | 7.23 | 14.75 | 16.42 | 32.53 | 7.17 | 14.23 | 16.28 |
| D *1.0 A-- *2.0 CN3H6+ *1.5 H₂O | 25.97 | 6.97 | 27.25 | 13.86 | 26.12 | 6.44 | 27.32 | 13.31 |
| D *1.5 A-- *.0 CN3H6+ *0.75 H₂O | 30.50 | 7.39 | 23.71 | 13.57 | 30.94 | 6.71 | 23.87 | 13.23 |
| (S)-Glyceric Acid | | | | | | | | |
| D *0.5 A *1.5 H₂O | 37.49 | 7.44 | 11.92 | 9.10 | 37.49 | 7.31 | 11.73 | 9.22 |
| L-(−)-Malic Acid | | | | | | | | |
| D *1.0 A *1.33 H₂O | 38.20 | 6.85 | 11.15 | | 38.37 | 6.51 | 11.09 | |
| D *0.5 A *1.75 H₂O | 37.92 | 7.48 | 13.22 | | 37.92 | 7.88 | 13.03 | |
| L-Ascorbic Acid | | | | | | | | |
| D *1.0 A *2.2 H₂O | 38.65 | 6.81 | 9.66 | | 38.91 | 6.80 | 9.43 | |
| 3-(N-morpholino)propane Sulfonate | | | | | | | | |
| D *1.0 A *2.5 H₂O | 38.04 | 7.87 | 11.83 | | 38.41 | 8.12 | 11.64 | |
| L-cysteic Acid | | | | | | | | |
| D *0.5 A *2.3 H₂O | 30.73 | 6.71 | 13.03 | | 30.91 | 7.05 | 12.98 | |
| (4S)-hydroxy-L-proline | | | | | | | | |
| D *1.0 A *0.3 H₂O | 44.89 | 7.53 | 15.74 | | 44.29 | 7.60 | 15.91 | |
| Cyclopropane-1,1-dicarboxylic Acid | | | | | | | | |
| D *1.0 A *1.3 H₂O | 41.88 | 6.92 | 11.27 | | 42.02 | 6.68 | 10.83 | |
| D *0.5 A *1.5 H₂O | 40.50 | 7.45 | 13.48 | | 40.70 | 7.10 | 12.98 | |
| 2,2-dimethylmalonic Acid | | | | | | | | |
| D *1.0 A *2.2 H₂O | 39.93 | 7.58 | 10.75 | | 39.88 | 7.37 | 10.37 | |
| D *0.5 A *1.8 H₂O | 39.68 | 7.80 | 13.22 | | 40.10 | 7.81 | 13.38 | |
| Ethanolamine | | | | | | | | |
| D *0.5 A *1.3 H₂O *2.0 HCl | 31.73 | 7.67 | 14.80 | 18.73 | 31.41 | 7.60 | 15.00 | 19.12 |
| Ethylene diamine | | | | | | | | |
| D *0.5 A *1.2 H₂O *2.0 HCl | 32.12 | 7.92 | 18.73 | 18.96 | 31.90 | 9.19 | 18.08 | 19.11 |
| D,L-Aspartic Acid | | | | | | | | |
| D *1.0 A *1.8 H₂O *0.4 HOAc | 37.60 | 7.20 | 13.70 | | 37.59 | 7.66 | 13.73 | |
| D-Glutamic Acid | | | | | | | | |
| D *1.0 A *1.8 H₂O *0.3 HOAc | 39.18 | 7.45 | 13.44 | | 39.47 | 7.52 | 13.29 | |
| Squaric Acid | | | | | | | | |
| D *1.0 A *0.5 H₂O | 42.10 | 5.89 | 12.27 | 9.37 | 42.29 | 5.72 | 12.73 | 9.42 |
| D *0.5 A *0.75 H₂O | 41.44 | 6.78 | 14.50 | 11.06 | 41.43 | 6.56 | 14.16 | 10.85 |
| Fumaric Acid | | | | | | | | |
| D *1.0 A *2.5 H₂O *2.5 EtOH | 41.20 | 8.34 | 8.48 | | 41.99 | 8.33 | 8.58 | |
| 1-hydroxy-2-naphthoic Acid | | | | | | | | |
| D *1.2 A *1.0 H₂O *1.0 EtOH | 54.72 | 6.85 | 8.25 | | 54.32 | 6.08 | 8.31 | |
| 1-hydroxy-2-naphthlenesulfonoc Acid | | | | | | | | |
| D *0.65 A *2.4 H₂O | 43.42 | 6.58 | 10.48 | | 51.01 | 6.53 | 10.39 | |

TABLE 8-continued

| Acid/Formula | Calculated C | H | N | Found C | H | N |
|---|---|---|---|---|---|---|
| 2-Carboxyethyl phosphonic Acid | | | | | | |
| D *1.1 A *1.25 H$_2$O *1.0 CaCl2 | 29.08 | 5.87 | 9.00 | 29.34 | 5.83 | 8.70 |
| D *1.5 A *1.0 H$_2$O | 33.15 | 6.49 | 9.64 | 33.17 | 6.56 | 9.28 |
| D *1.5 A *0.75 H$_2$O *1.0 LiCl | 29.65 | 5.77 | 8.30 | 29.66 | 5.71 | 8.84 |
| Phosphonoacetic Acid | | | | | | |
| D *0.5 A *2.5 H$_2$O | 32.58 | 6.83 | 12.66 | 32.16 | 6.73 | 13.33 |
| D *2.0 A *1.0 H$_2$O | 27.86 | 6.12 | 8.12 | 27.76 | 5.56 | 8.40 |
| Phenyl phosphonic Acid | | | | | | |
| D *1.0 A *0.5 H$_2$O | 43.52 | 6.52 | 10.87 | 43.90 | 6.78 | 10.12 |
| L-pyroglutamic Acid | | | | | | |
| D *1.0 A *1.2 H$_2$O | 42.20 | 7.19 | 15.15 | 42.35 | 7.10 | 15.01 |
| HPF$_6$ | | | | | | |
| D *1.0 A *0.5 H$_2$O | 26.31 | 4.97 | 11.23 | 26.63 | 5.10 | 10.64 |

BIOLOGICAL DATA

Some or all of the following assays are used to demonstrate the nitric oxide synthase inhibitory activity of the invention's compounds as well as demonstrate the useful pharmacological properties.

Citrulline Assay for Nitric Oxide Synthase

Nitric oxide synthase (NOS) activity can be measured by monitoring the conversion of L-[2,3-$^3$H]-arginine to L-[2,3-$^3$H]-citrulline (Bredt and Snyder, Proc. Natl. Acad. Sci. U.S.A., 87, 682–685, 1990 and Moore et al, J. Med. Chem., 39, 669–672, 1996). Human inducible NOS (hiNOS), human endothelial constitutive NOS (hecNOS) and human neuronal constitutive NOS (hncNOS) are each cloned from RNA extracted from human tissue. The cDNA for human inducible NOS (hiNOS) is isolated from a λcDNA library made from RNA extracted from a colon sample from a patient with ulcerative colitis. The cDNA for human endothelial constitutive NOS (hecNOS) is isolated from a λcDNA library made from RNA extracted from human umbilical vein endothelial cells (HUVEC) and the cDNA for human neuronal constitutive NOS (hncNOS) is isolated from a λcDNA library made from RNA extracted from human cerebellum obtained from a cadaver. The recombinant enzymes are expressed in Sf9 insect cells using a baculovirus vector (Rodi et al, in The Biology of Nitric Oxide, Pt. 4: Enzymology Biochemistry and Immunology; Moncada, S., Feelisch, M., Busse, R., Higgs, E., Eds.; Portland Press Ltd.: London, 1995; pp 447–450). Enzyme activity is isolated from soluble cell extracts and partially purified by DEAE-Sepharose chromatography. To measure NOS activity, 10 μL of enzyme is added to 40 μL of 50 mM Tris (pH 7.6) in the presence or absence of test compounds and the reaction initiated by the addition of 50 μL of a reaction mixture containing 50 mM Tris (pH 7.6), 2.0 mg/mL bovine serum albumin, 2.0 mM DTT, 4.0 mM CaCl$_2$, 20 μM FAD, 100 μM tetrahydrobiopterin, 0.4 mM NADPH and 60 μL-arginine containing 0.9 μCi of L-[2,3-$^3$H]-arginine. The final concentration of L-arginine in the assay is 30 μM. For hecNOS or hncNOS, calmodulin is included at a final concentration of 40–100 nM. Following incubation at 37° C. for 15 minutes, the reaction is terminated by addition of 400 μL of a suspension (1 part resin, 3 parts buffer) of Dowex 50W X-8 cation exchange resin in a stop buffer containing 10 mM EGTA, 100 mM HEPES, pH 5.5 and 1 mM L-citrulline. After mixing the resin is allowed to settle and L-[2,3-$^3$H]-Citrulline formation is determined by counting aliquots of the supernatant with a liquid scintillation counter. Results are reported in Table 1 as the IC$_{50}$ values of compounds for hiNOS, hecNOS and hncNOS.

In Vivo Assay

Rats can be treated with an intraperitoneal injection of 1–12.5 mg/kg of endotoxin (LPS) with or without oral administration of the nitric oxide synthase inhibitors. Plasma nitrite/nitrate levels can be determined 5 hours post-treatment. The results can be used to show that the administration of the nitric oxide synthase inhibitors decreases the rise in plasma nitrite/nitrate levels, a reliable indicator of the production of nitric oxide induced by endotoxin.

Raw Cell Nitrite Assay

RAW 264.7 cells can be plated to confluency on a 96-well tissue culture plate grown overnight (17h) in the presence of LPS to induce NOS. A row of 3–6 wells can be left untreated and served as controls for subtraction of nonspecific background. The media can be removed from each well and the cells washed twice with Kreb-Ringers-Hepes (25 mM, pH 7.4) with 2 mg/ml glucose. The cells are then placed on ice and incubated with 50 μL of buffer containing L-arginine (30 μM)+/−inhibitors for 1 h. The assay can be initiated by warming the plate to 37° C in a water bath for 1 h. Production of nitrite by intracellular iNOS will be linear with time. To terminate the cellular assay, the plate of cells can be placed on ice and the nitrite-containing buffer removed and analyzed for nitrite using a previously published fluorescent determination for nitrite. T. P. Misko et al, Analytical Biochemistry, 214, 11–16 (1993).

Human Cartilage Explant Assay

Bone pieces are rinsed twice with Dulbecco's Phosphate Buffered Saline (GibcoBRL) and once with Dulbecco's Modified Eagles Medium (GibcoBRL) and placed into a petri dish with phenol red free Minimum Essential Medium (MEM) (GibcoBRL). Cartilage was cut into small explants of approximately 15–45 mg in weight and one or two explants per well are placed into either 96 or 48 well culture plates with 200–500 μL of culture media per well. The culture media was either a custom modification of Minimum Essential Medium(Eagle) with Earle's salts (GibcoBRL) prepared without L-Arginine, without L-Glutamine and without phenol red or a custom modification of serumless Neuman and Tytell (GibcoBRL) medium prepared without L-arginine, without insulin, without ascorbic acid, without L-glutamine and without phenol red. Both are supplemented before use with 100 μM L-Arginine (Sigma), 2 mM L-glutamine, 1×HL-1 supplement (BioWhittaker), 50 mg/ml ascorbic acid (Sigma) and 150 pg/ml recombinant human IL-1β (RD Systems) to induce nitric oxide synthase. Compounds are then added in 10 μL aliquots and the explants incubated at 37° C. with 5% $CO_2$ for 18–24 hours. The day old supernatant is then discarded and replaced with fresh culture media containing recombinant human IL-1β and compound and incubated for another 20–24 hours. This supernatant is analyzed for nitrite with a fluorometric assay (Misko et al, *Anal. Biochem.*, 214, 11–16, 1993). All samples are done in quadruplicate. Unstimulated controls are cultured in media in the absence of recombinant human IL-1β. $IC_{50}$ values (Table 1) are determined from plotting the percent inhibition of nitrite production at six different concentrations of inhibitor.

Table 9 shows examples of biological activity for some of the compounds of the present invention.

TABLE 9

Biological Activity. Values represent averages across all experiments and all lots studied.

| Example Number of Compound | hiNOS $IC_{50}$ (μM) | hecNOS $IC_{50}$ (μM) | hncNOS $IC_{50}$ (μM) | Human Cartilage $IC_{50}$ (μM) |
|---|---|---|---|---|
| Example 1 | 3.1 | 77 | 15 | 0.7 |
| Example 2 | 4.4 | 302 | 58 | 8.2 |
| Example 3 | 74 | 266 | 86 | |
| Example 4 | 197 | 1100 | 539 | |
| Example 7 | 3.4 | 78 | 17 | |
| Example 11 | 0.9 | 26 | 6.0 | |
| Example 16 | 7.2 | >100 | 36 | 0.7 |
| Example 18 | 12 | >100 | 181 | |
| Example 19 | 12 | 1080 | 220 | |

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the preparation of a compound or a pharmaceutically acceptable salt thereof, the compound having a structure corresponding to Formula 21:

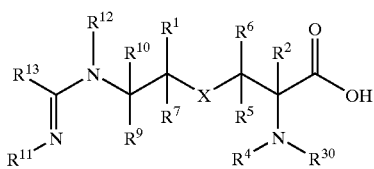

or a salt thereof, wherein:

X is selected from the group consisting of —S—, —S(O)—, and —S(O)$_2$—;

$R^2$ is selected from the group consisting of $C_1$–$C_6$ alkyl, $C_2$–$C_6$ alkenyl, $C_2$–$C_6$ alkynyl, $C_1$–$C_5$ alkoxy-$C_1$ alkyl, and $C_1$–$C_5$ alkylthio-$C_1$ alkyl;

$R^{30}$ is selected from the group consisting of —H, —OH, —C(O)—$R^{17}$, —C(O)—O—$R^{18}$, and —C(O)—S—$R^{19}$;

$R^1$, $R^5$, $R^6$, and $R^7$ independently are selected from the group consisting of —H, halogen, $C_1$–$C_6$ alkyl, $C_2$–$C_6$ alkenyl, $C_2$–$C_6$ alkynyl, and $C_1$–$C_5$ alkoxy-$C_1$ alkyl;

$R^9$ and $R^{10}$ independently are selected from the group consisting of —H, $C_1$–$C_6$ alkyl, $C_2$–$C_6$ alkenyl, $C_2$–$C_6$ alkynyl, and $C_1$–$C_5$ alkoxy-$C_1$ alkyl;

with respect to $R^{11}$ and $R^{12}$:

$R^{11}$ is selected from the group consisting of —H, —OH, —C(O)—O—$R^{24}$, and —C(O)—S—$R^{25}$; and $R^{12}$ is selected from the group consisting of —H, —OH, —C(O)—O—$R^{26}$, and —C(O)—S—$R^{27}$; or $R^{11}$ is —O—, and $R^{12}$ is —C(O)—, wherein $R^{11}$ and $R^{12}$ together with the atoms to which they are attached form a ring; or $R^{11}$ is —C(O)—, and $R^{12}$ is —O—, wherein $R^{11}$ and $R^{12}$ together with the atoms to which they are attached form a ring; and $R^{13}$ is $C_1$ alkyl;

$R^{17}$, $R^{18}$, $R^{19}$, $R^{24}$, $R^{25}$, $R^{26}$, $R^{27}$ and $R^{27a}$ independently are selected from the group consisting of —H and alkyl, which is optionally substituted by one or more moieties selected from the group consisting of cycloalkyl, heterocyclyl, aryl, and heteroaryl; and when any of $R^1$, $R^2$, $R^4$, $R^5$, $R^6$, $R^7$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{24}$, $R^{25}$, $R^{25}$ $R^{26}$, $R^{27}$ and $R^{27a}$ independently is a moiety selected from the group consisting of alkyl, alkenyl, alkynyl, alkoxy, alkylthio, cycloalkyl, heterocyclyl, aryl, and heteroaryl, then the moiety is optionally substituted by one or more substituent selected from the group consisting of —OH, alkoxy, and halogen;

wherein the method comprises treating a diamine compound having a structure corresponding to Formula 22:

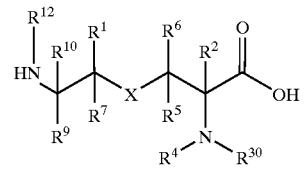

or a pharmaceutically acceptable salt thereof, with an alkyl acetimidate having a structure corresponding to Formula 23:

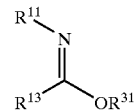

or a salt thereof, wherein $R^{31}$ is $C_1$–$C_6$ alkyl, to produce the compound corresponding to Formula 21.

2. The method of claim 1 wherein $R^{11}$ is selected from the group consisting of —H and —OH.

3. The method of claim 2 wherein $R^{11}$ is —H.

4. The method of claim 2 wherein $R^{11}$ is —OH.

5. The method of claim 2 wherein $R^{13}$ is methyl or halomethyl.

6. The method of claim 5 wherein $R^{13}$ is methyl.

7. The method of claim 2 wherein $R^{31}$ is $C_1$–$C_3$ alkyl.

8. The method of claim 7 wherein $R^{31}$ is ethyl.

9. The method of claim 1 wherein the treating of the diamine compound with the alkyl acetimidate compound is performed in the presence of a base.

10. The method of claim 9 wherein the base is selected from the group consisting of a hydrazine, a metal sulfide, a metal hydroxide, a metal alkoxide, an amine, a hydroxylamine, a metal amide complex, and a basic resin.

11. The method of claim 10 wherein the base is a basic resin.

12. The method of claim 11 wherein the basic resin is a polymer-bound diazabicyclo[4.4.0]dec-2-ene.

13. The method of claim 10 wherein the base is an amine.

14. The method of claim 13 wherein the base is selected from the group consisting of 1,5-diazabicyclo[4.3.0]non-5-ene; 1,4-diazabicyclo[2.2.2]octane; and 1,8-diazabicyclo[5.4.0]undec-7-ene.

* * * * *